(12) United States Patent
Guichard et al.

(10) Patent No.: US 7,186,828 B2
(45) Date of Patent: Mar. 6, 2007

(54) CYCLIC UREA COMPOUNDS AND PREPARATION THEREOF

(75) Inventors: Gilles Guichard, Wolfisheim (FR); Marc Rodriguez, deceased, late of Strasbourg (FR); by Marie-Christine Galas-Rodriguez, legal representative, Strasbourg (FR); by Pierre Rodriguez, legal representative, Strasbourg (FR); by Elisa Rodriguez, legal representative, Strasbourg (FR); by Romain Rodriguez, legal representative, Strasbourg (FR); Serge Plaue, Marienthal (FR); Vincent Semetey, Strasbourg (FR); Arnaud-Pierre Schaffner, Plobsheim (FR); Jean-Paul Briand, Strasbourg (FR)

(73) Assignee: ImmuPharma (France) SA, Mulhouse Cedex (FR)

( * ) Notice: Subject to any disclaimer, the term of this patent is extended or adjusted under 35 U.S.C. 154(b) by 220 days.

(21) Appl. No.: 10/311,178

(22) PCT Filed: Jun. 13, 2001

(86) PCT No.: PCT/FR01/01837

§ 371 (c)(1),
(2), (4) Date: Jun. 24, 2003

(87) PCT Pub. No.: WO01/96318

PCT Pub. Date: Dec. 20, 2001

(65) Prior Publication Data

US 2004/0044199 A1    Mar. 4, 2004

(30) Foreign Application Priority Data

Jun. 13, 2000    (FR) .................................. 00 07507

(51) Int. Cl.
C07D 243/00    (2006.01)
C07D 487/00    (2006.01)
C07D 255/04    (2006.01)
C07D 257/10    (2006.01)
C07D 259/00    (2006.01)

(52) U.S. Cl. ........................ 540/492; 540/496; 540/501
(58) Field of Classification Search ................ 540/492, 540/496, 501
See application file for complete search history.

(56) References Cited

U.S. PATENT DOCUMENTS 4,918,186 A * 4/1990 Kajimoto et al. ........... 540/492

(Continued)

FOREIGN PATENT DOCUMENTS

DE    28 47 760    *    5/1980

(Continued)

OTHER PUBLICATIONS

Hawley's Condensed Chemical Dictionary, 13th ed., revised by Richard J. Lewis, Sr, Van Nostrand Reinhold, p. 50, © 1997.*

(Continued)

*Primary Examiner*—Zachary C. Tucker
(74) *Attorney, Agent, or Firm*—McCarter & English, LLP

(57) ABSTRACT

A method for preparing cyclic urea compounds from at least an activated carbamic acid derivative containing an unprotected primary or secondary amine function, includes a cyclization step which consists in a reaction between the primary or secondary amine function and the carbamic acid function of the carbamic acid derivative(s).

3 Claims, 1 Drawing Sheet

U.S. PATENT DOCUMENTS

| | | | |
|---|---|---|---|
| 5,508,400 A | * | 4/1996 | Wilkerson et al. .......... 540/460 |
| 5,532,356 A | * | 7/1996 | Smyser et al. .............. 540/492 |
| 5,532,357 A | * | 7/1996 | Rodgers et al. ............. 540/492 |

FOREIGN PATENT DOCUMENTS

| | | |
|---|---|---|
| EP | 0 765 873 | 4/1997 |
| EP | 0 858 999 | 8/1998 |
| WO | WO 93/07128 | 4/1993 |
| WO | WO 96/29329 | 9/1996 |

OTHER PUBLICATIONS

Guha and Ramaswami, "Attempts to Synthesise Uric Acid from Nine-Membered Cycloids" Journal of the Indian Chemical Society, vol. 11, pp. 811-822 (1934).*

G. Guichard et al., "Solid phase synthesis of oligourea using O-succinimidyl-(9H-fluoren-9-ylmethoxycarbonylamino) ethylcarbamate derivatives as activated monomers" Tetrahedron Letters, NL, Elsevier Science Publishers, Amsterdam, vol. 41, No. 10, Mar. 2000, pp. 1553-1557.

G. Guichard et al, "Effective preparation of O-Succinimidyl-2-(tert-butoxycarbonylamino beta-amino acids", Journal of Organic Chemistry, vol. 64, No. 23, Nov. 12, 1999, pp. 8702-8705.

M.E. Wilson et al., "An Efficient Synthesis of N, N'-Linked Oligoureas" Tetrahedron Letters, NL, Elsevier Science Publishers, Amsterdam, vol. 39, No. 37, Sep. 10, 1998; pp. 6613-6616.

K. Burgess et al., "Solid phase syntheses of Oligoureas", Journal of the Americal Chemical Society, US, American Chemical Society, Washington, DC, vol. 119, No. 7, Feb. 19, 1997, pp. 1556-1564.

Jong-Man K et al, "The Solid Phase Synthesis of Oligoureas" Tetrahedron Letters, NL, Elsevier Science Publishers, Amsterdam, vol. 37, No. 30, Jul. 22, 1996, pp. 5305-5308.

* cited by examiner

CYCLIC UREA COMPOUNDS AND PREPARATION THEREOF

The invention relates to a new method for preparation of cyclic urea compounds and new cyclic urea compounds.

The last few years have seen rapid development in the synthesis and uses of substituted ureas. In particular, cyclic ureas are present in a number of active ingredients currently being developed in the pharmaceutical industry, such as HIV protease inhibitors, or factor Xa (fXa) inhibitors. The cyclic ureas described in the literature (WO 93/07128, WO 96/29329, WO 97/08150, WO 98/20009) generally possess rings of 5, 6, 7 or 8 atoms. These rings can sometimes contain an additional hetero atom, such as a nitrogen atom adjacent to the urea function (Sham et al., Journal of Medicinal Chemistry, 1996, 39, 392–397). The urea ring of the biologically active cyclic ureas described in the literature is used as a restrained conformation platform on which are arranged the pharmacophoric groups used for recognition by the HIV protease. It is therefore important to have a method of synthesis which is sufficiently flexible to easily allow the introduction of a molecular diversity at the level of the pharmacophoric groups as well as at the level of the position of these groups on the ring. The cyclic ureas described in the literature are generally prepared from the corresponding diamines by intramolecular cyclisation of said diamines using a carbonylation agent such as carbonyldiimidazole. The alkylation of N,N'-disubstituted ureas by alkyl bihalides for the preparation of cyclic ureas has also been described (WO96/00708 and WO 93/07128).

Within the framework of research aimed at developing new compounds with immunomodulating activity, the applicant Company has previously developed a simple and effective method for the preparation of new stable activated carbamic acid derivatives from an N-protected amino acid derivative, comprising three steps:

a) a step of transformation of the —COOH group of the N-protected amino acid ($\alpha$, $\beta$, $\gamma$ and $\delta$ amino acids) into a —CON$_3$ group in order to obtain an acyl azide, b) a step of transformation of the —CON$_3$ group of the acyl azide into a —NCO group in order to obtain an isocyanate, c) a step of treatment of the isocyanate in order to obtain said stable carbamic acid derivative.

The term "amino acid derivative" must be interpreted in a broad sense, as understood by the person skilled in the art, and designates in particular a peptide, polypeptide, protein, pseudopeptide or oligourea derivative.

The carbamic acid derivatives are stable, crystalline intermediates which react with amines to form substituted ureas. The carbamic acid derivatives also make it possible to prepare peptides containing urea motifs (Guichard et al., J. Org. Chem. 1999, 64, 8702–8705, and Guichard et al., Tetrahedron Letter, 2000, 41, 1553–1557).

One of the aspects of the invention is to propose a new method for preparation of cyclic urea compounds.

Another aspect of the invention is to propose a new method for preparation of cyclic urea compounds, making it possible in order to obtain easily and in very few steps a considerable molecular diversity of cyclic urea compounds.

Another aspect of the invention is to propose new cyclic urea compounds.

Generally, a subject of the invention is a method for preparation of cyclic urea compounds from at least one activated carbamic acid derivative containing a non-protected primary or secondary amine function, comprising a step of cyclisation by reaction between the primary or secondary amine function and the carbamic acid function of said carbamic acid derivative or derivatives.

The term "activated carbamic acid derivative" denotes a carbamic acid derivative, in particular a carbamate, containing a primary or secondary amine function capable of reacting with primary or secondary amines in the presence or not in the presence of a base in an organic solvent.

The term "non-protected" primary or secondary amine function denotes a free primary or secondary amine function, i.e. one capable of reacting with another chemical functional group, and in particular with a carbamic acid function. The "non-protected" primary or secondary function may also be referred to as "released", "free" or "deprotected" primary or secondary amine function.

In the following, the term "activated carbamic acid derivative containing a non-protected primary or secondary amine function" is also understood to mean:

an oligomeric carbamic acid derivative, also referred to in the following as "activated homo-oligomeric carbamic acid derivative" or "homo-oligomeric derivative" or "activated hetero-oligomeric carbamic acid derivative" or "hetero-oligomeric derivative" or, a monomeric carbamic acid derivative, corresponding to an activated non-homo-oligomeric carbamic acid or to an activated non-hetero-oligomeric carbamic acid derivative.

The homo-oligomeric and/or hetero-oligomeric carbamic acid derivatives are obtained at the end of one or more homo-oligomerisation and/or hetero-oligomerisation reactions of at least one activated monomeric carbamic acid derivative. The homo-oligomerisation or hetero-oligomerisation reactions may also be referred to in the following as "intermolecular reactions".

The term "cyclisation step" must be understood to mean an intramolecular cyclisation step, or an intermolecular cyclisation step.

Intramolecular cyclisation occurs by reaction between the non-protected primary or secondary amine function of the activated carbamic acid derivative and its carbamic acid function.

Intermolecular cyclisation occurs by reaction between:

the non-protected primary or secondary amine function of an activated carbamic acid derivative (denoted derivative 1) and the carbamic acid function of another activated carbamic acid derivative (denoted derivative 2) and, the non-protected primary or secondary amine function of said carbamic acid derivative 2 and the carbamic acid function of said carbamic acid derivative 1.

According to an advantageous embodiment, the invention concerns a method for preparation of cyclic urea compounds comprising:

a step of obtaining at least one activated carbamic acid derivative containing a non-protected primary or secondary amine function from at least one stable activated carbamic acid derivative containing an amine function protected by a protecting group, by selective release of said protected amine function from said stable activated carbamic acid derivative or derivatives, by cleavage or transformation of said protecting group, a step of cyclisation by reaction between the non-protected primary or secondary amine function of at least one activated derivative obtained at the end of the selective release step and the carbamic acid function of the derivative or derivatives.

According to an advantageous embodiment of the method of the invention, the cyclisation step is an intramolecular cyclisation between the non-protected primary or secondary amine function of an activated derivative obtained at the end of the selective release step and its carbamic acid function.

The term "protecting group" denotes a group protecting the amine function of the activated carbamic acid derivative, in particular to prevent it from reacting with other chemical functional groups, during synthesis of said derivative.

The term "stable activated carbamic acid derivative" denotes a carbamic acid derivative which can be isolated, purified and stored (preferably at 4° C.) for a period of at least 3 months without appreciable degradation. Stability can be measured for example by the following test: high performance liquid chromatography (HPLC), thin-layer chromatography (TLC), nuclear magnetic resonance (No) or infra red (IR).

The term "selective release" of the protected amine function must be understood to mean a release making it possible to release only the protected amine function of the stable activated carbamic acid derivative without altering the carbamic acid function of said derivative. In the following, the "selective release" step may also be referred to as "selective deprotection".

The selective release or deprotection step of the amine function protected by a protecting group is dependent on:
the protecting group used to protect the amine function and,
the reagent used during deprotection or release of the amine function.

The release of an amine function by cleavage of the protecting group or by transformation of the protecting group is carried out according to the standard methods described in the literature.

According to an advantageous embodiment of the method of the invention, the stable activated carbamic acid derivative containing an amine function protected by a protecting group is obtained from an amino acid derivative in which the amino group is protected by a method such as that described below, comprising the following three steps:
transformation of the —COOH group of the N-protected amino acid derivative into a $CON_3$ group in order to obtain an acyl azide,
transformation of the —$CON_3$ group of the acyl azide into an —NCO group in order to obtain an isocyanate,
treatment of the —NCO isocyanate in order to obtain said stable carbamic acid derivative.

According to an advantageous embodiment of the preparation method of the invention, the non-protected primary or secondary amine function of the activated carbamic acid derivative is present:
(1) in free form and/or,
(2) in protonated form, in particular in salt form.

As an example of an activated carbamic acid derivative containing a primary or secondary amine in protonated form, in particular in salt form, the following may in particular be cited: an acetate salt, a hydrochloride salt or a trifluoroacetate salt.

The activated carbamic acid derivative containing a non-protected primary or secondary amine function in protonated form can be isolated, whereas the activated carbamic acid derivative containing a non-protected primary or secondary amine function in free form cannot be isolated: in the latter case, the cyclisation step takes place immediately after obtaining at least one activated carbamic acid derivative containing a non-protected primary or secondary amine function is obtained.

According to an advantageous embodiment of the invention, the method for preparation of cyclic urea compounds comprises, during or at the end of the selective release step, a homo-oligomerisation and/or hetero-oligomerisation step between:
the non-protected primary or secondary amine function of a molecule of the activated carbamic acid derivative and the carbamic acid function of another molecule of said activated carbamic acid derivative and/or,
between the non-protected primary or secondary amine function of a molecule of the activated carbamic acid derivative and the carbamic acid function of a molecule of another activated carbamic acid derivative, in order to obtain at least one homo-oligomeric and/or hetero-oligomeric derivative of carbamic acid containing a non-protected primary or secondary amine function.

Thus, according to an advantageous embodiment, the preparation method of the invention comprises, during or at the end of the selective release step:
a homo-oligomerisation step between the non-protected primary or secondary amine function of a molecule of the activated carbamic acid derivative and the carbamic acid function of another molecule of said activated carbamic acid derivative, in order to obtain at least one homo-oligomeric carbamic acid derivative containing a non-protected primary or secondary amine function or,
at least one homo-oligomerisation step between the non-protected primary or secondary amine function of a molecule of an activated carbamic acid derivative and the carbamic acid function of another molecule of said activated carbamic acid derivative and at least one hetero-oligomerisation step between the non-protected primary or secondary amine function of a molecule of one activated carbamic acid derivative and the carbamic acid function of a molecule of another activated carbamic acid derivative, in order to obtain at least one homo-oligomeric and at least one hetero-oligomeric carbamic acid derivative containing a non-protected primary or secondary amine function.

Thus the bifunctional acyclic precursors obtained during or at the end of the selective release of the protected amine function, namely the monomeric activated carbamic acid derivatives containing a primary or secondary amine function in free or protonated form, can undergo, before the intramolecular cyclisation step, intermolecular homo- and/or hetero-oligomerisation reactions, to form homo-oligomeric and/or hetero-oligomeric bifunctional acyclic precursors. The acyclic homo-oligomeric and/or hetero-oligomeric carbamic acid derivatives thus obtained, like acyclic non-homo-oligomeric and/or non-hetero-oligomeric carbamic acid derivatives, then undergo intramolecular cyclisation (or macrocyclisation) by reaction of their non-protected primary or secondary amine function with their carbamic acid function, in order to obtain homo-oligomeric and/or hetero-oligomeric cyclic ureas.

However, for the intermolecular homo-oligomerisation and/or hetero-oligomerisation reactions, and the intramolecular cyclisation reactions to take place, the released primary or secondary amine function of the activated carbamic acid derivative must be in free form and not in protonated form. In effect, only the primary or secondary amine function in free form can react by intermolecular homo-oligomerisation or hetero-oligomerisation reaction, or by intramolecular cyclisation.

Thus, when the activated carbamic acid derivative, obtained at the end of the selective release step, contains a non-protected primary or secondary amine function in free form, the homo- and/or hetero-oligomerisation, and intramolecular cyclisation reactions can take place immediately after the formation of the activated carbamic acid derivative containing a non-protected primary or secondary amine function in free form, as said amine function in free form can react with the activated carbamic acid group.

When the activated carbamic acid derivative obtained at the end of the selective release step contains a non-protected primary or secondary amine function in protonated form, it will be necessary beforehand to neutralise said protonated form of the amine into free form so that the intermolecular homo-oligomerisation and/or hetero-oligomerisation reactions, and the intramolecular cyclisation reactions can take place.

According to an advantageous embodiment of the method for preparation of cyclic urea compounds, when the activated carbamic acid derivative contains a primary or secondary amine function in protonated form, the homo-oligomerisation and/or hetero-oligomerisation step is carried out by neutralising the primary or secondary amine function in protonated form into a primary or secondary amine function in free form, in order to obtain at least one homo-oligomeric and/or hetero-oligomeric derivative containing a non-protected primary or secondary amine function in free form.

According to another advantageous embodiment of the method for preparation of cyclic urea compounds, when the activated carbamic acid derivative contains a primary or secondary amine function in protonated form, the cyclisation step is carried out by neutralising the primary or secondary amine function in protonated form into a primary or secondary amine function in free form.

The neutralisation of said protonated amine function into free form is in particular carried out using a base chosen from the group made up of diisopropylethylamine, triethylamine, lutidine, pyridine, 2,4,6-collidine, N-methylmorpholine, 2,6-di-tert-butyl-4-methylpyridine or mixtures thereof.

Furthermore, to carry out the step of intramolecular cyclisation of the activated oligomeric or monomeric carbamic acid derivatives containing a primary or secondary amine function, it is possible to use in particular a solvent chosen from the group made up of acetonitrile (MeCN), toluene, pyridine, N,N-dimethylformamide (DMF), tetrahydrofuran (THF), chloroform, dichloromethane, N-methylpyrrolidone (NMP), dimethylsulfoxide (DMSO), ethyl acetate, methanol, ethanol or mixtures thereof.

The solvent used to carry out the cyclisation step is denoted in the following by the term "reaction solvent" or "cyclisation solvent".

Thus, the step of intramolecular cyclisation of activated carbamic acid derivatives containing a non-protected primary or secondary amine function in protonated form is carried out in the presence:

of a base in order to neutralise the protonated form of the amine into free form and,
of the reaction solvent for intramolecular cyclisation,
whereas the step of intramolecular cyclisation of activated carbamic acid derivatives containing a non-protected primary or secondary amine function in free form is carried out directly using a reaction solvent for intramolecular cyclisation.

According to an advantageous embodiment of the method of the invention the step of intramolecular cyclisation of the activated carbamic acid derivative containing a non-protected primary or secondary function is carried out at a temperature of approximately −40° C. to approximately 40° C., in particular of approximately −20° C. to approximately 40° C., and preferably of approximately 0° C. to approximately 20° C.

According to another advantageous embodiment of the method of the invention, the concentration of an activated carbamic acid derivative containing a non-protected primary or secondary amine function in free form, in a solution containing a reaction solvent for intramolecular cyclisation, is approximately $10^{-6}$ M to approximately 10 M, in particular approximately $10^{-5}$ M to approximately 1 M, and preferably approximately $10^{-4}$ M to approximately 1 M.

According to another advantageous embodiment of the method of the invention, the concentration of an activated carbamic acid derivative containing a non-protected primary or secondary amine function in protonated form, in a solution containing a reaction solvent for intramolecular cyclisation and a base, is approximately $10^{-6}$ M to approximately 10 M, in particular approximately $10^{-5}$ M to approximately 1 M, and preferably approximately $10^{-4}$ M to approximately 1 M.

The concentration of the base in the reaction solvent for intramolecular cyclisation is approximately $10^{-6}$ M to approximately 10 M, in particular approximately $10^{-5}$ M to approximately 1 M, and preferably approximately $10^{-4}$ M to approximately 1 M.

According to an advantageous embodiment of the method for preparation of cyclic urea compounds, the activated carbamic acid derivative containing a protected amine function is synthesised on a solid support, and is chemically bonded to said solid either (a) by its amine function, or (b) by its carbamic acid function, or (c) by any other functional group present in said activated carbamic acid derivative.

The term "solid support" must be understood to mean the matrix on which the chemical reaction is carried out. This is generally an insoluble solid polymer which allows the filtration or centrifugation, and hence the separation of the reagents and of the product formed on the resin. As examples of solid supports, the following may be cited: polystyrene resins, polyacrylamide, polyethylene glycol, cellulose, glass and silica.

According to an advantageous embodiment of the preparation method of the invention, when the activated carbamic acid derivative containing a protected amine function is chemically bonded to a solid support:

by its amine function, the selective release step involves the cleavage of the amine function of said derivative vis-à-vis the support,
by its carbamic acid function, the cyclisation step involves the cleavage of the carbamic acid function of said derivative vis-à-vis the support,
by a functional group other than the amine or carbamic acid function, such as a hydroxyl function, an amide function or a carboxyl function, the cleavage of said functional group vis-à-vis the support can take place during or at the end of any one of the selective release or cyclisation steps.

According to another advantageous embodiment of the preparation method of the invention, the amine function of the activated carbamic acid derivative is protected in the form of:

a carbamate (ROCON—) group in which R is a tert-butyl, 9-fluorenylmethyl, benzyl, allyl, tert-butyldimethylsilyl, ethyl, 2,2,2-trichloroethyl, 2-(trimethylsilyl)ethyl group,
tertiary amine group of formula R'N< when the amine function to be protected is a secondary amine, or of formula R'R"N— when the amine function to be protected is a primary amine, R' and R" each representing a protecting group chosen from the group made up of benzyl, 4-methoxybenzyl, 2,4-dimethoxybenzyl, diphenylmethyl, para-methoxyphenyl, 3,4-dimethoxybenzyl or 9-phenyl-9-fluorenyl an amide group, a nitro group, an azide group, a trityl group, an ortho-(or para)-nitrophenylsulfonyl group, a tosyl group, a phthalimide group, or a cyano group.

The release of the amine function by cleavage of the protecting group is carried out according to the standard methods described in the literature. In this connection, reference may be made to the work entitled "Protecting groups" by P. J. Kocienski (Thieme edition), which gives an exhaustive list of the protecting groups of the amine functions and their deprotection methods As examples, reference may be made in particular to:

deprotection of the tert-butoxycarbonyl group (ROCO— with R=tert-butyl group) (also called Boc group) in acid condition (trifluoroacetic acid or hydrochloric acid solution in a 3–4 M organic solvent) which leads to the obtaining of the corresponding amine in trifluoroacetate or hydrochloride salt form, deprotection of the benzyloxycarbonyl group (ROCO— with R=benzyl group) (also called Z group) or tertiary amines (of formula R'N< or R'R"N—) containing one or two benzyl groups, by catalytic hydrogenation in the presence of Pd/C, with or without the addition of an acid to protonate, or not to protonate, the released primary or secondary amine.

The release of the amine function by transformation of a chemical group serving as hidden form of the amine such as a nitro, cyano, amide or azide group is in particular described in the examples below. However, these examples are not exhaustive, as there is a large number of methods making it possible to achieve the transformations described below ("Textbook of Practical Organic Chemistry" de Vogel, (5th edition), 1989).

The release of the amine function can be carried out by reduction of the nitro or cyano groups into amine, for example by catalytic hydrogenation in the presence of Pd/C and $PtO_2$ respectively.

The transformation of an amide group into an amine group can be carried out by Hoffman rearrangement, for example by treatment of the amide with iodobenzyl bis-trifluoroacetate in a water/acetonitrile mixture.

The reduction of an azide group into an amine group can be carried out by different methods, for example by catalytic hydrogenation or by treatment with lithium aluminium hydride.

The invention also relates to cyclic urea compounds comprising a ring of at least 7 atoms, in particular from 7 to 50 atoms, and preferably from 7 to 20 atoms, said ring comprising at least one amide function and at least one urea function, each amide or urea function being separated from the closest adjacent amide or urea function by at least one carbon atom, and in particular by 1 to 4 carbon atoms.

The invention relates in particular to cyclic urea compounds comprising a ring of at least 7 atoms, in particular from 7 to 50 atoms, and preferably from 7 to 10 atoms, said ring comprising one amide function and one urea function, separated from one another by at least one carbon atom, and in particular by 1 to 4 carbon atoms.

In this respect, the invention concerns cyclic urea compounds of formula (Ia):

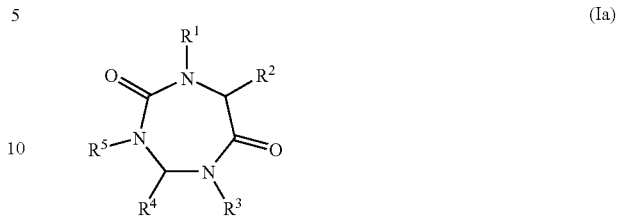

in which the $R^1$, $R^2$, $R^3$, $R^4$ and $R^5$ groups can each and independently from one another represent:

a)—a hydrogen, b)—a halogen, c)—the protected or non-protected side chain of an amino acid chosen from the natural or non-natural amino acids, d)—a linear or branched alkyl group (C1–C20), non-substituted or substituted by one or more substituents which include: —$COOR_a$, —$CONHR_a$, —$OR_a$, —$NHR_a$, —NH($CO)R_a$, —$NHCOOR_a$, an aryl or heteroaryl group, whose cyclic structure contains from 5 to 20 carbon atoms, one halogen atom, and an R'''CO— group, the R''' group comprising from 1 to 10 carbon atoms, a nitrile, guanidino or nitro group, e)—an aryl group whose ring structure contains from 5 to 20 carbon atoms, substituted or non-substituted by the abovementioned substituents, and by cyano or amidine groups, f)—an alkenyl or alkynyl group (C1–C6)

g)—a sulfonyl group ($R_cSO2$)

h)—an acyl group ($R_cCO$)

i)—an $OR_b$ group j)—an $NH_2$ group k) —$COOR_b$ l) —$CONHR_b$ m) —$CH_2CONH_2$ $R_a$ and $R_b$ representing, independently from one another, a hydrogen, an allyl, benzyl, t-butyl, fluorenylmethyl, benzyloxymethyl, tert-butyldimethylsilyl, 2-ethoxyethyl, methoxymethyl, 2-methoxyethoxymethyl, tetrahydropyran-2-yl, trimethylsilyl, triethylsilyl, 2-(trimethylsilyl)ethyl, trityl, 2,2,2-trichloroethyl, tosyl, ortho-(or para)-nitrophenylsulfonyl, or alkyl group having from 1 to 20 carbon atoms, or an aryl group whose ring structure contains from 5 to 20 carbon atoms, $R_c$ representing an alkyl group having from 1 to 20 carbon atoms, or an aryl group whose ring structure contains from 5 to 20 carbon atoms, or a heteroaryl, arylalkyl or heteroarylalkyl group, the $R^1$, $R^2$, $R^3$ and $R^4$ groups also being able to form the following intramolecular cyclisations:

1/cyclisation between $R^1$ and $R^2$ and/or,

2/cyclisation between $R^3$ and $R^4$, said cyclic urea compounds able to be, when one or more asymmetric carbons are present in formula (Ia), independently, either of R configuration (rectus) or of S configuration (sinister).

An advantageous group of cyclic urea compounds corresponding to general formula (Ia) is made up of the cyclic urea compounds corresponding more particularly to formulae (Ib), (Ic), (Id), (Ie), (If), (Ig), (Ih):

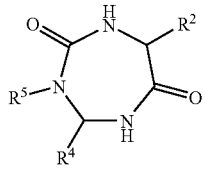
Ih

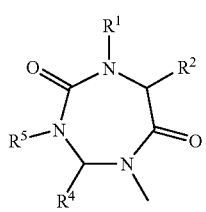
Ib

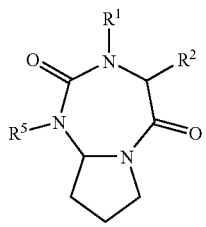
Ic

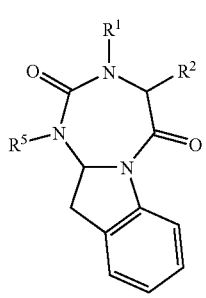
Id

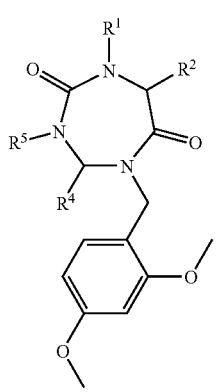
Ie

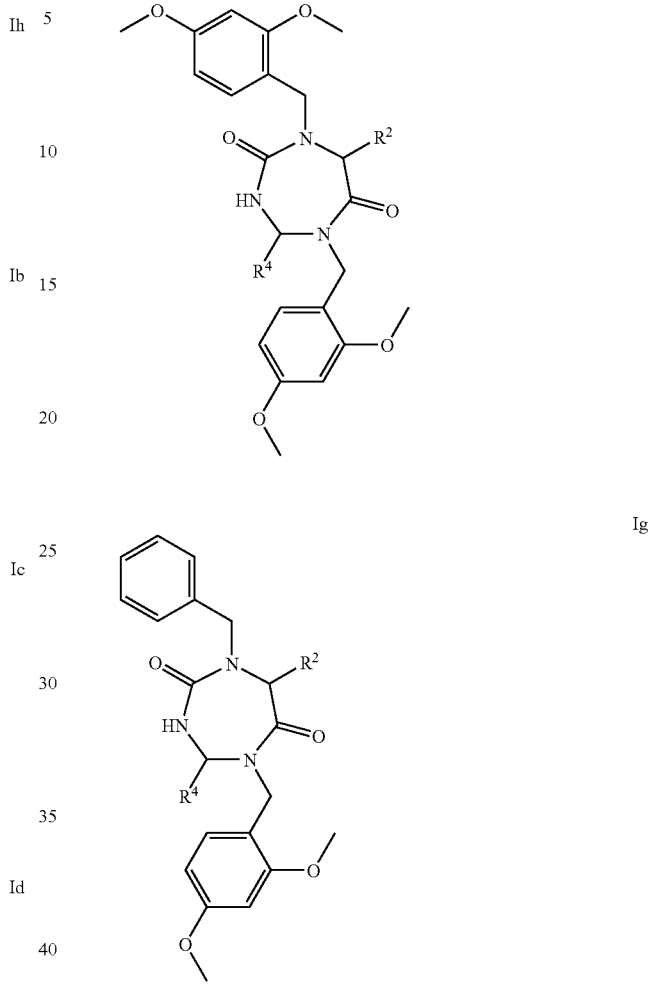

If

Ig in which the $R^1$, $R^2$, $R^4$ and $R^5$ groups have the meanings indicated above, the $R^1$ and $R^2$ groups also being capable of forming an intramolecular cyclisation, said cyclic urea compounds able to be, when one or more asymmetric carbons are present in formulae (Ib) to (Ih), independently, either of R configuration (rectus) or of S configuration (sinister).

In the compounds represented above and below, the bond <<—>> represents a methyl group, and could also be represented as follows: <<—$CH_3$>>.

The invention also concerns the cyclic urea compounds of formulae (IIa), (IIb), (IIc), (IId):

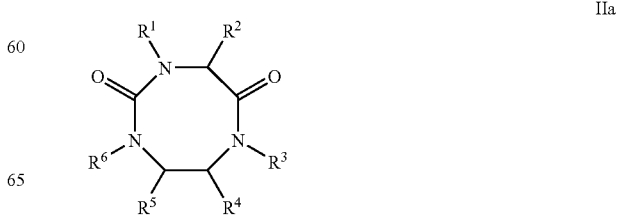
IIa

-continued

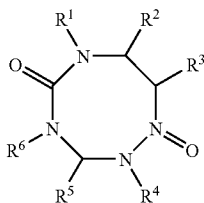
IIb

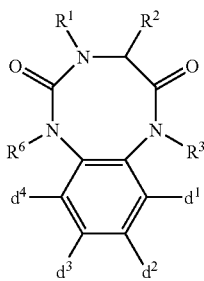
IIc

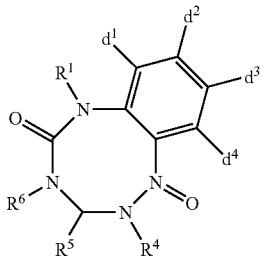
IId in which the $R^1$, $R^2$, $R^3$, $R^4$, $R^5$ and $R^6$ groups have the meanings indicated above regarding the $R^1$ to $R^5$ groups, the $R^1$, $R^2$, $R^3$, $R^4$ and $R^5$ groups also being able to form the following intramolecular cyclisations:

1/cyclisation between $R^1$ and $R^2$ or,
2/cyclisation between $R^2$ and $R^3$ and/or,
3/cyclisation between $R^4$ and $R^5$ or,
4/cyclisation between $R^5$ and $R^6$, the $d^1$, $d^2$, $d^3$ and $d^4$ groups can each represent, independently from one another: a nitro, alkyl group comprising from 1 to 4 carbon atoms, and in particular a methyl, alkoxy group comprising from 1 to 7 carbon atoms, and in particular a methoxy, aryloxy group comprising from 5 to 10 carbon atoms, and in particular a benzyloxy, halogen group, such as a fluoro, bromo, chloro or iodo, CN, guanidino, $NHR_a$, $NHCOOR_a$, $COOR_a$, or $OR_a$ group, $R_a$ having the meanings indicated above, said cyclic urea compounds able to be, when one or more asymmetric carbons are present in formulae (IIa) to (IId), independently, either of R configuration (rectus) or of S configuration (sinister).

The invention also relates to cyclic urea compounds comprising a ring of at least 14 atoms, in particular from 14 to 30 atoms, and preferably from 14 to 20 atoms, said ring comprising two amide functions and two urea functions, each amide or urea function being separated from the closest adjacent amide or urea function by at least one carbon atom, and in particular by 1 to 4 carbon atoms.

In this respect, the invention concerns cyclic urea compounds of formula (IIIa):

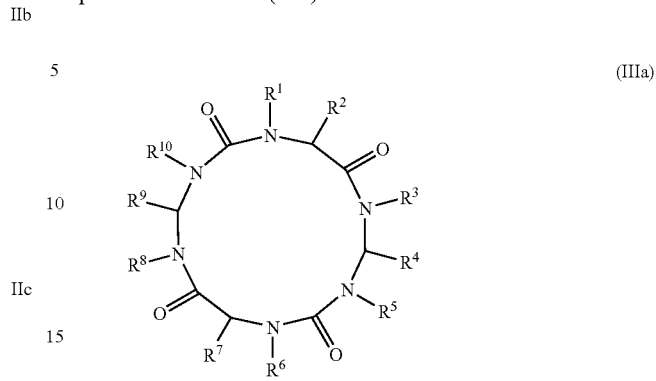
(IIIa)

in which the $R^1$, $R^2$, $R^3$, $R^4$, $R^5$, $R^6$, $R^7$, $R^8$, $R^9$ and $R^{10}$ groups have the meanings mentioned above regarding the $R^1$ to $R^5$ groups, the $R^1$, $R^2$, $R^3$, $R^4$, $R^5$, $R^6$, $R^7$, $R^8$ and $R^9$ groups can also form the following intramolecular cyclisations:

1/cyclisation between $R^1$ and $R^2$ and/or,
2/cyclisation between $R^3$ and $R^4$ and/or,
3/cyclisation between $R^6$ and $R^7$ and/or,
4/cyclisation between $R^8$ and $R^9$, said cyclic urea compounds able to be, when one or more asymmetric carbons are present in formula (IIIa), independently, either of R configuration (rectus) or of S configuration (sinister).

An advantageous group of cyclic urea compounds corresponding to general formula (IIIa) is constituted by the cyclic urea compounds corresponding more particularly to formulae (IIIb), (IIIc), (IIId), (IIIe), (IIIf) and (IIIg):

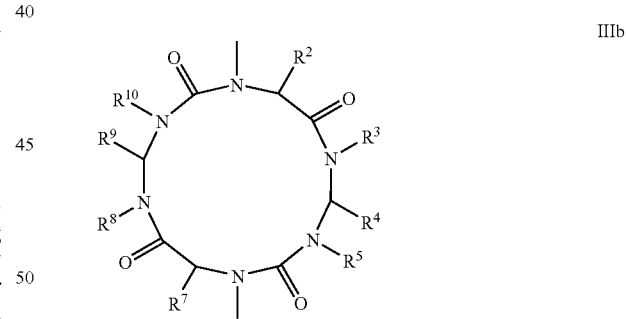
IIIb

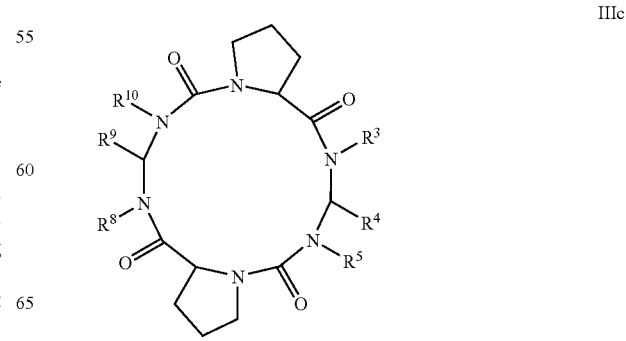
IIIc

-continued

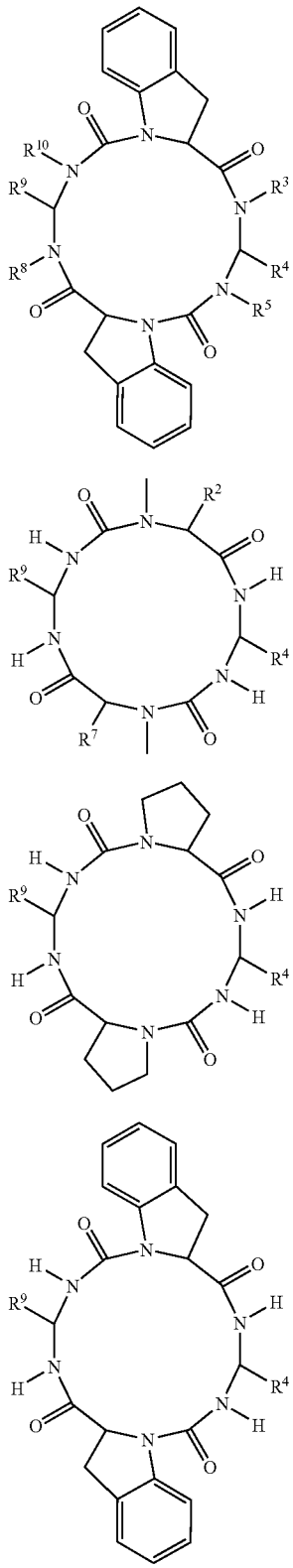

IIId

IIIe

IIIf

IIIg in which the $R^2$, $R^3$, $R^4$, $R^5$, $R^7$, $R^8$, $R^9$ and $R^{10}$ groups have the meanings mentioned above regarding the $R^1$ to $R^5$ groups, the $R^3$, $R^4$, $R^7$, $R^8$ and $R^9$ groups also being capable of forming intramolecular cyclisations as defined above regarding the $R^1$, $R^2$, $R^3$, $R^4$, $R^5$, $R^6$, $R^7$, $R^8$ and $R^9$ groups of the compounds of general formula (IIIa), said cyclic urea compounds able to be, when one or more asymmetric carbons are present in formulae (IIIb) to (IIIg), independently, either of R configuration (rectus) or of S configuration (sinister).

The invention also relates to cyclic urea compounds consisting of a ring having 7 atoms and comprising a urea function, of formula (IVa):

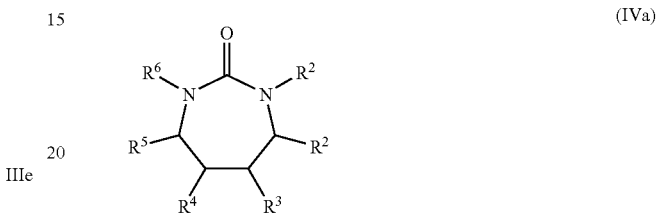

(IVa)

in which $R^1$, $R^2$, $R^3$, $R^4$, $R^5$ and $R^6$ have the meanings mentioned above regarding the $R^1$ to $R^5$ groups, with the restriction that if $R^3=R^4=OH$ then $R^2$ must be different from $R^5$, the $R^1$, $R^2$, $R^3$, $R^4$ and $R^5$ groups also being able to form the following intramolecular cyclisations:

1/cyclisation between $R^1$ and $R^2$ and/or,

2/cyclisation between $R^2$ and $R^3$ and/or,

3/cyclisation between $R^3$ and $R^4$ and/or,

4/cyclisation between $R^4$ and $R^5$, said cyclic urea compounds able to be, when one or more asymmetric carbons are present in formula (IVa), independently, either of R configuration (rectus) or of S configuration (sinister).

According to an advantageous embodiment, the activated carbamic acid derivative containing a non-protected primary or secondary amine function involved in the preparation method of the invention corresponds respectively:

either to one of the following formulae (VIa), (VIb), (VIc) or (VId) (in order to obtain the compounds of formulae (Ia) to (Ih) as defined above):

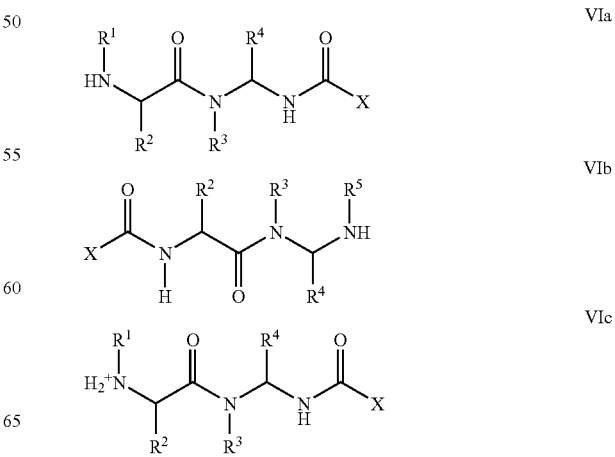

-continued

VId

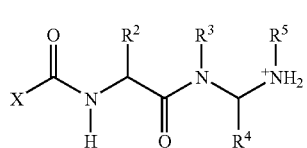

in which:

the X group represents a group conferring upon the derivative an activated carbamic acid derivative structure, said X group being produced from a compound chosen in particular from the phenols, optionally substituted by at least one nitro group or at least one halogen, or hydroxylamine derivatives, or benzyl alcohol derivatives grafted onto a solid support and more particularly chosen from the following compounds: N-hydroxysuccinimide, phenol, pentafluorophenol, pentachlorophenol, p-nitrophenol, 2,4-dinitrophenol, 2,4,5-trichlorophenol, 2,4-dichloro-6-nitrophenol, hydroxy-1,2,3-benzotriazole, 1-oxo-2-hydroxydihydrobenzotriazine (HODhbt), 7-aza-1-hydroxy-benzotriazole (HOAt), 4-aza-1-hydroxybenzotriazole (4-HOAt), imidazole, tetrazole, and WANG resin, the $R^1$, $R^2$, $R^3$, $R^4$, and $R^5$ groups have the meanings mentioned above regarding the $R^1$ to $R^5$ groups, or to one of the following formulae (VIIa), (VIIb), (VIIc) or (VIId) (in order to obtain the compounds of formula (IIa) as defined above):

VIIa
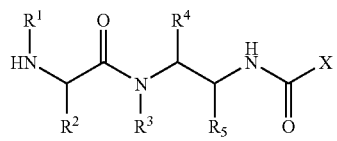

VIIb
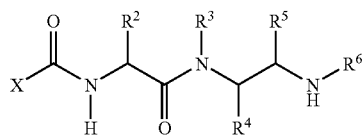

VIIc
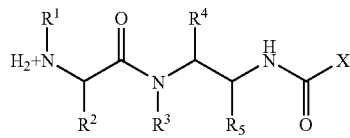

VIId
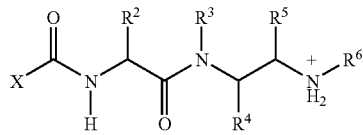

in which:
X is as defined above,
the $R^1$, $R^2$, $R^3$, $R^4$, $R^5$ and $R^6$ groups have the meanings mentioned above regarding the $R^1$ to $R^5$ groups, or to one of the following formulae (VIIIa), (VIIIb), (VIIIc) or (VIIId) (in order to obtain the compounds of formula (IIb) as defined above):

VIIIa
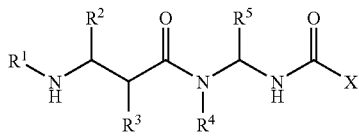

VIIIb
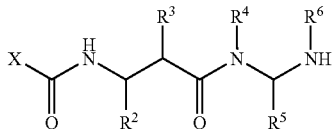

VIIIc
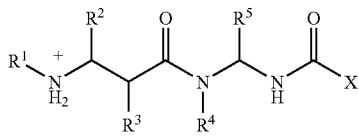

VIIId
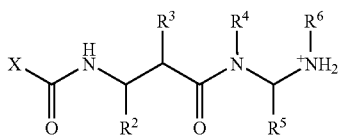

in which:
X is as defined above,
the $R^1$, $R^2$, $R^3$, $R^4$, $R^5$ and $R^6$ groups have the meanings mentioned above regarding the $R^1$ to $R^5$ groups, or to one of the following formulae (IXa), (IXb), (IXc) or (IXd) (in order to obtain the compounds of formula (IIc) as defined above):

IXa
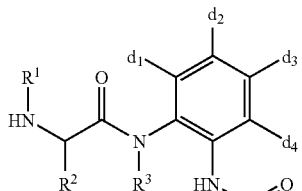

IXb
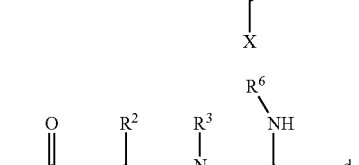

IXc
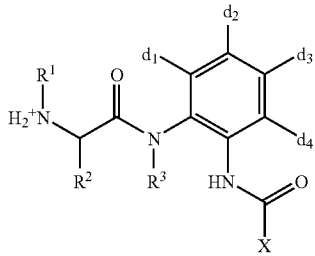

-continued

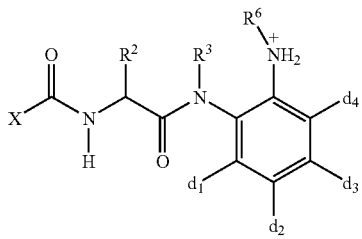

IXd in which:
X is as defined above,
the $R^1$, $R^2$, $R^3$, and $R^6$ groups have the meanings mentioned above regarding the $R^1$ to $R^5$ groups,
the $d^1$, $d^2$, $d^3$ and $d^4$ groups have the meanings mentioned above,
or to one of the following formulae (Xa), (Xb), (Xc) or (Xd) (in order to obtain the compounds of formula (IId) as defined above):

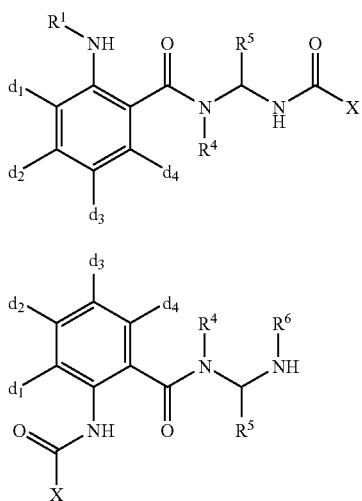

Xa

Xb

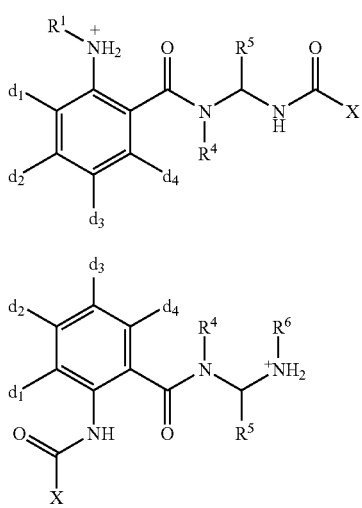

Xc

Xd in which:
X is as defined above,
the $R^1$, $R^4$, $R^5$, and $R^6$ groups have the meanings mentioned above regarding the $R^1$ to $R^5$ groups,
the $d^1$, $d^2$, $d^3$ and $d^4$ groups have the meanings mentioned above,
or to one of the following formulae (XIa), (XIb), (XIc), (XId) (in order to obtain the compounds of formulae (IIIa) to (IIIg) as defined above):

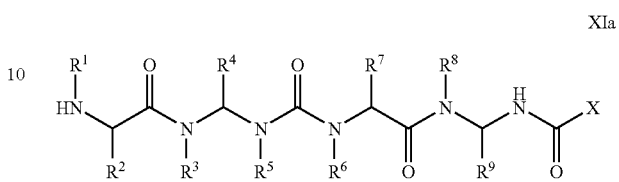

XIa

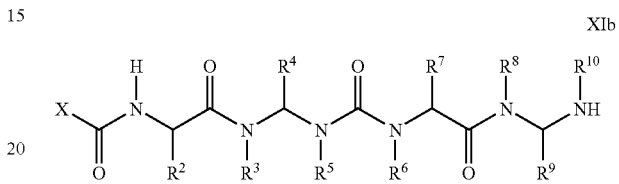

XIb

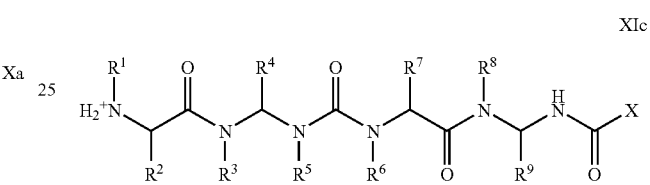

XIc

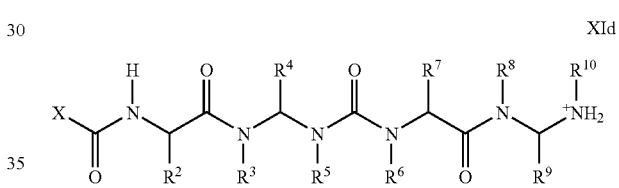

XId in which
X is as defined above,
the $R^1$, $R^2$, $R^3$, $R^4$, $R^5$, $R^6$, $R^7$, $R^8$, $R^9$ and $R^{10}$ groups have the meanings mentioned above regarding the $R^1$ to $R^5$ groups,
or to one of the following formulae (XIIa) or (XIIb) (in order to obtain the compounds of formulae (IVa) as defined above):

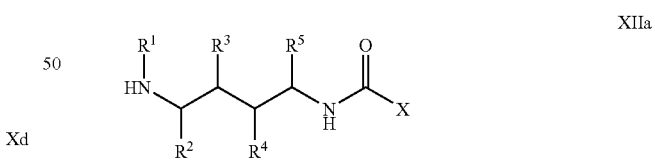

XIIa

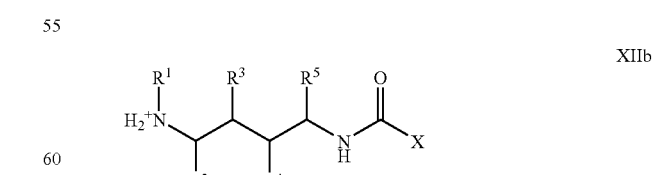

XIIb in which:
X is as defined above,
the $R^1$, $R^2$, $R^3$, $R^4$, and $R^5$ groups have the meanings mentioned above regarding the $R_1$ to $R^5$ groups.

According to an advantageous embodiment of the present invention, the activated carbamic acid derivatives containing a non-protected primary or secondary amine function of formulae:

(VIa), (VIb), (VIc), (VId), (VIIa), (VIIb), (VIc), (VIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), are obtained by selective release of the protected amine function of the corresponding stable activated carbamic acid derivatives under the conditions described below.

Examples of protecting groups and deprotection solvents used in order to obtain the compounds (VIIa), (VIIb), (VIIc), (VIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa) and (XIIb) respectively, are given below.

The amine function of the stable activated carbamic acid derivatives will be advantageously protected by oxycarbonyl groups (such as the tert-butoxycarbonyl (Boc) groups or benzyloxycarbonyl (Z) groups) or benzyl groups, or will be masked in the form of nitro, cyano or azide groups. Two methods of deprotection will be used advantageously according to the method of the invention.

The Boc group will be deprotected by acid hydrolysis (for example using trifluoroacetic acid (TFA), or a TFA/dichloromethane mixture, or a hydrochloric acid (HCl) solution in an organic solvent (dioxane, ether etc.)), at a temperature of approximately 0° C. to approximately 40° C., in order in order to obtain carbamic acid derivatives containing a protonated primary or secondary amine function, in trifluoroacetate or hydrochloride form.

The hydrogenation will be used for cleavage of the Z and benzyl groups, and for reduction of the nitro, cyano or azide groups. The hydrogenation can be carried out with catalysts of the $PtO_2$, Pd/C type in solvents such as ethanol, methanol, dimethylformamide (DMF), ethyl acetate, tetrahydrofuran (THF), chloroform or a mixture of said solvents, at a temperature of approximately 0° C. to approximately 40° C., and at a pressure of approximately 1 bar to approximately 100 bar. In the absence of acid added during hydrogenation (HCl or acetic acid), deprotection leads exclusively to carbamic acid derivatives containing a primary or secondary amine function in free form. The addition of an HCl or acetic acid equivalent makes it possible in order to obtain carbamic acid derivatives containing a protonated primary or secondary amine function, in acetate or hydrochloride form.

The cyclisation of the activated carbamic acid derivatives containing a non-protected primary or secondary amine function in protonated form of formulae:

(VIa), (VIb), (VIc), (VId),
(VIIa), (VIIb), (VIIc), (VIId),
(VIIIa), (VIIIb), (VIIIc), (VIIId),
(IXa), (IXb), (IXc), (IXd),
(Xa), (Xb), (Xc), (Xd),
(XIa), (XIb), (XIc), (XId),
(XIIa), (XIIb), in order to obtain respectively the activated carbamic acid derivatives containing formulae:

(Ia) to (Ih),
(IIa),
(IIb),
(IIc),
(IId),
(IIIa) to (IIIg),
(IVa), is carried out respectively in the conditions described below.

The carbamic acid derivative containing a primary or secondary amine function in protonated form, namely the derivative of formula (VIc), (VId), (VIIc), (VIId), (VIIIc), (VIId), (IXc), (IXd), (Xc), (Xd), (XIc), (XId) or (XIIb) is:

rendered soluble in the cyclisation solvent, in particular chosen from the group made up of acetonitrile (MeCN), toluene, pyridine, N,N-dimethylformamide (DMF), tetrahydrofuran (THF), chloroform, dichloromethane, N-methylpyrrolidone (NMP), dimethylsulfoxide (DMSO), ethyl acetate, methanol, ethanol or mixtures thereof, then is added dropwise to a solution containing a base, in particular that chosen from the group made up of diisopropylethylamine, triethylamine, lutidine, pyridine, 2,4,6-collidine, N-methylmorpholine, 2,6-di-tert-butyl-4-methylpyridine or mixtures thereof, and the reaction solvent as defined above, at a temperature of approximately −20° C. to approximately 20° C., and in particular of approximately 0° C. to 20° C.

The concentration of the carbamic acid derivative containing a primary or secondary amino acid function in protonated form in the cyclisation solvent is approximately $10^{-4}$ M to approximately 1 M, and in particular approximately $10^{-3}$ M to approximately 1 M.

The concentration of the base in the cyclisation solvent is approximately $10^{-6}$ M to approximately 10 M, in particular approximately $10^{-5}$ M to approximately 1 M, and preferably approximately $10^{-4}$ M to approximately 1 M.

The cyclisation conditions of the carbamic acid derivative containing a primary or secondary amine function in free form, namely the derivative of formula (VIa), (VIb), (VIIa), (VIIb), (VIIIa), (VIIIb), (IXa), (IXb), (Xa), (Xb), (XIa), (XIb) or (XIIa), differ from those set forth above in relation to the carbamic acid derivatives containing a primary or secondary amine function in protonated form only in that it is not necessary to operate in the presence of a base.

According to another advantageous embodiment, the invention concerns a method as defined above, for the preparation of cyclic urea compounds of formula (IIIa) to (IIIg) as defined above, characterised in that said compounds (IIIa) to (IIIg) are obtained at the end of a homo-oligomerisation or hetero-oligomerisation reaction, from at least one activated carbamic acid derivative containing a primary or secondary amine function, corresponding to at least one of formulae (VIa), (VIb), (VIc) or (VId) as defined above.

The homo-oligomerisation or hetero-oligomerisation reaction of activated carbamic acid derivatives containing a primary or secondary amine function of formula (VIa), (VIb), (VIc) or (VId), as well as the cyclisation of the homo- or hetero-oligomers thus obtained into cyclic urea compounds of formula (IIIa) to (IIIg), is encouraged for carbamic acid derivatives of formula (VIa), (VIb), (VIc) or (VId) in which the —CO—$NR^3$ bond mostly adopts a trans conformation.

The homo-oligomerisation or hetero-oligomerisation reaction is advantageously carried out for low concentrations of the activated carbamic acid derivatives of formula (VIa), (VIb), (VIc) or (VId) in the cyclisation solvent, namely concentrations of approximately $10^{-3}$ M to approximately $10^{-5}$ M, at temperatures of approximately 0° C. to approximately 20° C.

According to an advantageous embodiment, the preparation method of the invention is characterised in that it comprises:

a step of cyclisation of the activated carbamic acid derivatives containing a non-protected primary or secondary amine function, leading to cyclic urea compounds comprising in their ring a urea function of formula —NH—CO—N< or —NH—CO—NH—, a step of alkylation of the hydrogen of the —NH— group or groups included in the urea function of the cyclic urea compound obtained at the end of the cyclisation step above.

The step of alkylation of the hydrogen of the —NH— group or groups included in the urea function of the cyclic urea compound obtained at the end of the cyclisation step consists of reacting an alkylating agent on the NH function or functions of the cyclic urea in the presence of an adapted base.

As an example of an alkylating agent, a halogenated derivative can in particular be cited, the halogen group being generally a chlorine, bromine or iodine.

As an example of a base, it is possible in particular to cite that chosen from the group made up of:
  a metal hydride, such as a sodium hydride (NaH),
  a metal alcoholate such as sodium methanolate or potassium t-butanolate,
  sodium, lithium or potassium bis(trimethylsilyl)amide, potassium fluoride on alumina ($KF/Al_2O_3$),
  in non-protic solvents such as tetrahydrofuran (THF), N,N-dimethylformamide (DMF), N-methylpyrrolidone, dimethoxy ethane (DME), or under phase transfer conditions with potassium carbonate ($K_2CO_3$), sodium carbonate ($Na_2CO_3$) or potash (KOH).

According to an advantageous embodiment, the method for preparation of the cyclic urea compounds of formula (Ia), (Ib), (Ic), (Id), (Ie), (If), (Ig) and (Ih) as described above is more particularly characterised in that it consists of:
  a step of cyclisation:
    of the activated carbamic acid derivatives containing a non-protected primary or secondary amine function of formula (VIa) or (VIc) or,
    of the activated carbamic acid derivatives containing a non-protected primary or secondary amine function of formula (VIb) or (VId),
  leading respectively to:
    cyclic urea compounds comprising in their ring a urea function of formula —NH—CO—$NR^1$— or,
    cyclic urea compounds comprising in their ring a urea function of formula —$R^5N$—CO—NH—,
  a step of alkylation respectively:
    of the hydrogen of the urea function of formula —NH—CO—$NR^1$— obtained at the end of the cyclisation step using an alkylating agent comprising the $R^5$ group or,
    of the hydrogen of the urea function of formula —$R^5N$—CO—NH— obtained at the end of the cyclisation step using an alkylating agent comprising the $R^1$ group,
  in order to obtain the cyclic urea compounds of formulae (Ib), (Ic), (Id), (Ie), (If), (Ig) and (Ih) comprising in their ring the urea function —($R^5N$—CO—$NR^1$)—, the $R^1$ and $R^5$ groups being as described above.

According to an advantageous embodiment, the method for preparation of the cyclic urea compounds of formula (IIa) is more particularly characterised in that it consists of:
  a step of cyclisation:
    of the activated carbamic acid derivatives containing a non-protected primary or secondary amine function of formula (VIIa) or (VIIc) or,
    of the activated carbamic acid derivatives containing a non-protected primary or secondary amine function of formula (VIIb) or (VIId),
  leading respectively to:
    cyclic urea compounds comprising in their ring a urea function of formula —NH—CO—$NR^1$— or,
    cyclic urea compounds comprising in their ring a urea function of formula —$R^6N$—CO—NH—,
  a step of alkylation respectively:
    of the hydrogen of the urea function of formula —NH—CO—$NR^1$— obtained at the end of the cyclisation step using an alkylating agent comprising the $R^6$ group or,
    of the hydrogen of the urea function of formula —$R^6N$—CO—NH— obtained at the end of the cyclisation step using an alkylating agent comprising the $R^1$ group,
  in order to obtain the cyclic urea compounds of formula (IIa) comprising in their ring the urea function —($R^6N$—CO—$NR^1$)—, the $R^1$ and $R^6$ groups being as described above.

According to an advantageous embodiment, the method for preparation of the cyclic urea compounds of formula (IIb) is more particularly characterised in that it consists of:
  a step of cyclisation:
    of the activated carbamic acid derivatives containing a non-protected primary or secondary amine function of formula (VIIIa) or (VIIc) or,
    of the activated carbamic acid derivatives containing a non-protected primary or secondary amine function of formula (VIIIb) or (VIIId),
  leading respectively to:
    cyclic urea compounds comprising in their ring a urea function of formula —NH—CO—$NR^1$— or,
    cyclic urea compounds comprising in their ring a urea function of formula —$R^6N$—CO—NH—,
  a step of alkylation respectively:
    of the hydrogen of the urea function of formula —NH—CO—$NR^1$— obtained at the end of the cyclisation step using an alkylating agent comprising the $R^6$ group or,
    of the hydrogen of the urea function of formula —$R^6N$—CO—NH— obtained at the end of the cyclisation step using an alkylating agent comprising the $R^1$ group,
  in order to obtain the cyclic urea compounds of formula (IIb) comprising in their ring the urea function —($R^6N$—CO—$NR^1$)—.

According to an advantageous embodiment, the method for preparation of the cyclic urea compounds of formula (IIc) is more particularly characterised in that it consists of:
  a step of cyclisation:
    of the activated carbamic acid derivatives containing a non-protected primary or secondary amine function of formula (IXa) or (IXc) or,
    of the activated carbamic acid derivatives containing a non-protected primary or secondary amine function of formula (IXb) or (IXd),
  leading respectively to:
    cyclic urea compounds comprising in their ring a urea function of formula —NH—CO—$NR^1$— or,
    cyclic urea compounds comprising in their ring a urea function of formula —$R^6N$—CO—NH—,
  a step of alkylation respectively:
    of the hydrogen of the urea function of formula —NH—CO—$NR^1$— obtained at the end of the cyclisation step using an alkylating agent comprising the $R^6$ group or, of the hydrogen of the urea function of formula —R⁶N—CO—NH— obtained at the end of the cyclisation step using an alkylating agent comprising the R¹ group, in order to obtain the cyclic urea compounds of formula (IIc) comprising in their ring the urea function —(R⁶N—CO—NR¹)—.

According to an advantageous embodiment, the method for preparation of the cyclic urea compounds of formula (IId) is more particularly characterised in that it consists of:

a step of cyclisation:
of the activated carbamic acid derivatives containing a non-protected primary or secondary amine function of formula (Xa) or (Xc) or,
of the activated carbamic acid derivatives containing a non-protected primary or secondary amine function of formula (Xb) or (Xd), leading respectively to:
cyclic urea compounds comprising in their ring a urea function of formula —NH—CO—NR¹— or,
cyclic urea compounds comprising in their ring a urea function of formula —R⁶N—CO—NH—, a step of alkylation respectively:
of the hydrogen of the urea function of formula —NH—CO—NR¹— obtained at the end of the cyclisation step using an alkylating agent comprising the R⁶ group or,
of the hydrogen of the urea function of formula —R⁶N—CO—NH— obtained at the end of the cyclisation step using an alkylating agent comprising the R¹ group, in order to obtain the cyclic urea compounds of formula (IId) comprising in their ring the urea function —(R⁶N—CO—NR¹)—.

According to an advantageous embodiment, the method for preparation of the cyclic urea compounds of formulae (IIIa), (IIIb), (IIIc), (IIId), (IIIe), (IIIf) and (IIIg) is more particularly characterised in that it consists of:

a step of cyclisation:
of the activated carbamic acid derivatives containing a non-protected primary or secondary amine function of formula (XIa) or (XIc) or,
of the activated carbamic acid derivatives containing a non-protected primary or secondary amine function of formula (XIb) or (XId), leading respectively to:
cyclic urea compounds comprising in their ring a urea function of formula —NH—CO—NR¹— or,
cyclic urea compounds comprising in their ring a urea function of formula —R¹⁰N—CO—NH—, a step of alkylation respectively:
of the hydrogen of the urea function of formula —NH—CO—NR¹— obtained at the end of the cyclisation step using an alkylating agent comprising the R₁₀ group or,
of the hydrogen of the urea function of formula —R¹⁰N—CO—NH— obtained at the end of the cyclisation step using an alkylating agent comprising the R¹ group, in order to obtain the cyclic urea compounds of formulae (IIIa), (IIIb), (IIIc), (IIId), (IIIe), (IIIf) and (IIIg) comprising in their ring the urea function —(R¹⁰N—CO—NR¹)—, the R¹ and R¹⁰ groups being as described above.

According to an advantageous embodiment, the method for preparation of the cyclic urea compounds of formula (IVa) is more particularly characterised in that it consists of:

a step of cyclisation of the activated carbamic acid derivatives containing a non-protected primary or secondary amine function of formula (XIIa) or (XIIb), leading to cyclic urea compounds comprising in their ring a urea function of formula —NH—CO—NR¹—, a step of alkylation of the hydrogen of the urea function of formula —NH—CO—NR¹— obtained at the end of the cyclisation step using an alkylating agent comprising the R⁶ group, in order to obtain the cyclic urea compounds of formula (IVa) comprising in their ring the urea function —(R⁶N—CO—NR¹)—.

The alkylation step of the method for preparation of the cyclic urea compounds as described above, can in particular be carried out under the particular conditions described below. A solution of a cyclic urea compound (10 mmol) in THF (10 ml) is added dropwise to a suspension of NaH (1–1.2 equivalents if one NH is to be alkylated, 2–2.4 equivalents if two NH are to be alkylated) in THF (under Argon and at 0° C.). The reaction medium is agitated at 0° C. for 60 minutes then the alkylating agent (1–1.5 equivalents if one NH is to be alkylated, 2–3 equivalents if two NH's are to be alkylated) dissolved in THF is added at 0° C. The reaction is left for 12 h then the reaction medium is diluted with ethyl acetate and with a saturated NH₄Cl solution. The organic phase is washed with a saturated KHSO₄ 1N, H₂O solution, a saturated NaHCO₃ solution and H₂O. The organic phase is dried over MgSO₄ and the solvent is concentrated by rotative evaporation.

The invention also concerns a method as defined above for preparation of cyclic urea compounds comprising a 6-atom ring and comprising a urea function of formula

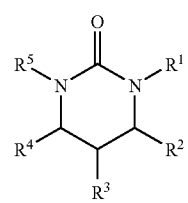

(Va)

in which R¹, R², R³, R⁴ and R⁵ can each and independently from one another represent:

a)—a hydrogen, b)—a halogen, c)—the protected or non-protected side chain of an amino acid chosen from the natural or non-natural amino acids, d)—a linear or branched alkyl group (C1–C20), non-substituted or substituted by one or more substituents which include: —COOR$_a$, —CONHR$_a$, —OR$_a$, —NHR$_a$, —NH(CO)R$_a$, —NHCOOR$_a$, an aryl or heteroaryl group, whose cyclic structure contains from 5 to 20 carbon atoms, a halogen atom, and an R'''CO— group, the R''' group comprising from 1 to 10 carbon atoms, a nitrile, guanidino or nitro group, e) an aryl group whose ring structure contains from 5 to 20 carbon atoms, substituted or non-substituted by the abovementioned substituents, as well as by the cyano or amidine groups, f)—an alkenyl or alkynyl group (C1–C6)

g)—a sulfonyl group (R$_c$SO2)

h)—an acyl group (R$_c$CO)

i)—an OR$_b$ group j)—an NH₂ group k) —COOR$_b$,
l) —CONHR$_b$,
m) —CH$_2$CONH$_2$ R$_a$ and R$_b$ representing, independently from one another, a hydrogen, an allyl, benzyl, t-butyl, fluorenylmethyl, benzyloxymethyl, tert-butyldimethylsilyl, 2-ethoxyethyl, methoxymethyl, 2-methoxyethoxymethyl, tetrahydropyran-2-yl, trimethylsilyl, triethylsilyl, 2-(trimethylsilyl)ethyl, trityl, 2,2,2-trichloroethyl, tosyl, ortho-(or para)-nitrophenylsulfonyl, alkyl group having from 1 to 20 carbon atoms, or an aryl group whose ring structure contains from 5 to 20 carbon atoms, R$_c$ representing an alkyl group having from 1 to 20 carbon atoms, or an aryl group whose ring structure contains from 5 to 20 carbon atoms, or a heteroaryl, arylalkyl or heteroarylalkyl group, the R$^1$, R$^2$, R$^3$ and R$^4$ groups being able to form the following intramolecular cyclisations:

1/cyclisation between R$^1$ and R$^2$ and/or,
2/cyclisation between R$^3$ and R$^4$, said cyclic urea compounds able to be, when one or more asymmetric carbons are present in formula (Va), independently, either of R configuration (rectus) or of S configuration (sinister), starting from an activated carbamic acid derivative containing a primary or secondary amine function corresponding to one of the following formulae (XIIIa) or (XIIIb):

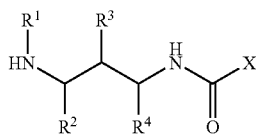

XIIIa

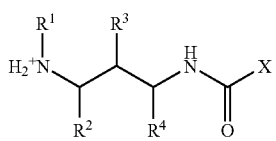

XIIIb in which:

the X group represents a group conferring upon the derivative an activated carbamic acid derivative structure, said X group being produced from a compound chosen in particular from the phenols, optionally substituted by at least one nitro group or at least one halogen, or hydroxylamine derivatives, or benzyl alcohol derivatives grafted onto a solid support and more particularly chosen from the following compounds: N-hydroxysuccinimide, phenol, pentafluorophenol, pentachlorophenol, p-nitrophenol, 2,4-dinitrophenol, 2,4,5-trichlorophenol, 2,4-dichloro-6-nitrophenol, hydroxy-1,2,3-benzotriazole, 1-oxo-2-hydroxydihydrobenzotriazine (HODhbt), 7-aza-1-hydroxy-benzotriazole (HOAt), 4-aza-1-hydroxybenzotriazole (4-HOAt), imidazole, tetrazole, and WANG resin, and the R$^1$, R$^2$, R$^3$ and R$^4$ groups are as defined above.

The invention also relates to a method as defined above for preparation of cyclic urea compounds comprising a ring having at least 8 atoms, said ring comprising at least two urea functions separated from one another by at least one carbon atom and in particular by 1 to 4 carbon atoms.

In this respect, the invention also relates to a method as defined above for preparation of cyclic urea compounds comprising a ring having at least 8 atoms, and comprising at least two urea functions separated from one another by two carbon atoms, corresponding to formulae (XIV), (XV) and (XVIa):

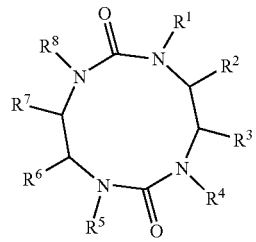

XIV

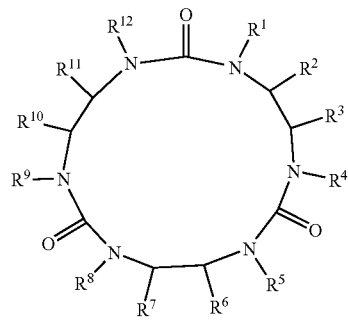

XV

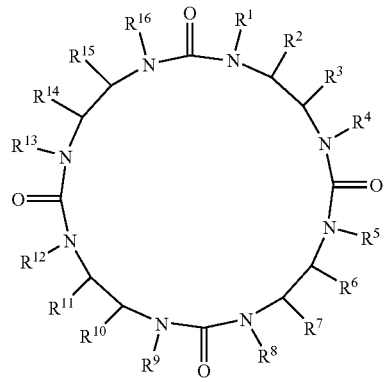

XVIa in which the R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$ and R$^{16}$ groups have the meanings mentioned above regarding the R$^1$ to R$^5$ groups, the R$^1$, R$^2$, R$^5$, R$^6$, R$^9$, R$^{10}$, R$^{13}$ and R$^{14}$ groups also being able to form the following intramolecular cyclisations:

1/cyclisation between R$^1$ and R$^2$ and/or,
2/cyclisation between R$^5$ and R$^6$ and/or,
3/cyclisation between R$^9$ and R$^{10}$ and/or,
4/cyclisation between R$^{13}$ and R$^{14}$, starting from, respectively, activated carbamic acid derivatives containing a primary or secondary amine function and corresponding to the following formulae (XXIII), (XXIV) and (XXV):

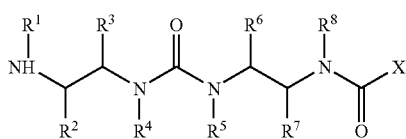

XXIII

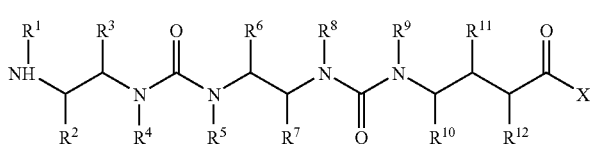

XXIV

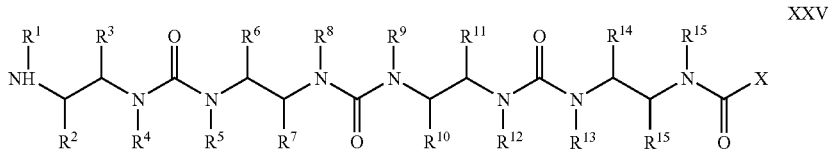

XXV in which:
the $R^1, R^2, R^3, R^4, R^5, R^6, R^8, R^9, R^{10}, R^{11}, R^{12}, R^{13}, R^{14}, R^{15}$ and $R^{16}$ groups are as defined above,
the X group is as defined above,
said carbamic acid derivatives also being able to be in protonated form.

A subject of the invention is also a method as defined above for preparation of cyclic urea compounds comprising at least four urea functions, of formulae (XVIb), (XVIc), (XVId) and (XVIe):

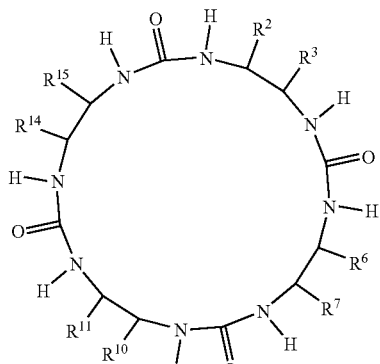

XVIb

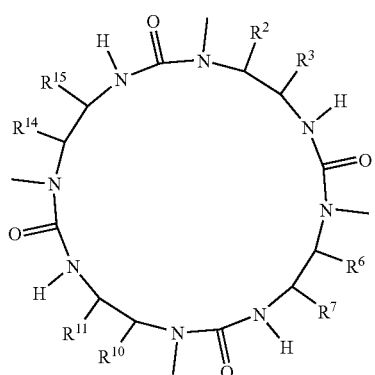

XVIc

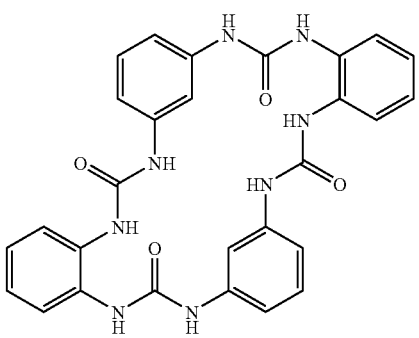

XVId

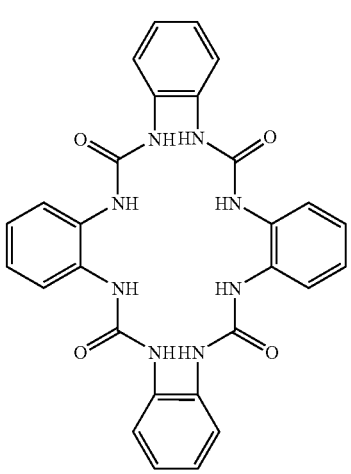

XVIe in which:
in which the $R^2, R^3, R^6, R^7, R^6, R^{10}, R^{11}, R^{14}$ and $R^{15}$ groups have the meanings mentioned above regarding the $R^1$ to $R^5$ groups, The invention also relates to a method as defined above, for preparation of compounds of formula (XVIh), in which:
the substituents $R^2$, $R^6$, $R^{10}$ and $R^{14}$ are chosen from:
  a hydrogen atom,
  a linear or branched C1–C6 alkyl chain, substituted or non-substituted by:
    i) a protected or non-protected amine function,
    ii) a protected or non-protected acid function,
    iii) a protected or non-protected alcohol function,
    iv) an aryl or heteroaryl group,
  the protected or non-protected side chain of an amino acid chosen from the natural or non-natural amino acids
the substituents $R^3$, $R^7$, $R^{11}$ and $R^{15}$ represent a hydrogen atom,
starting from activated carbamic acid derivatives of formula (XXV), as mentioned above, in which:
  i)—the substituents $R^2$, $R^6$, $R^{10}$ and $R^{14}$ have the same definition as above and the substituents $R^1$, $R^3$, $R^4$, $R^5$, $R^7$, $R^8$, $R^9$, $R^{11}$, $R^{12}$, $R^{15}$ and $R^{16}$ represent a hydrogen atom, or
  the substituents $R^3$, $R^7$, $R^{11}$ and $R^{15}$ have the meanings mentioned previously for $R^2$, $R^6$, $R^{10}$ and $R^{14}$ and the substituents $R^1$, $R^2$, $R^4$, $R^5$, $R^6$, $R^8$, $R^9$, $R^{10}$, $R^{12}$, $R^{14}$ and $R^{16}$ represent a hydrogen atom, and
  ii) the $R^{13}$ group is an arylalkyl or heteroarylalkyl group, which can be bonded to a solid support,
and allowing the formation, before the final deprotection step, of a synthesis intermediate having formula (XVIa), as mentioned above, in which the different substituents $R_1$ to $R^{16}$ have the same meanings as mentioned above for the compound of formula (XXV).

The invention also relates to a method as defined above, for preparation of compounds of formula (XV), in which:
the substituents $R^2$, $R^6$ and $R^{10}$ are chosen from:
  a hydrogen atom,
  a linear or branched C1–C7 alkyl chain, substituted or non-substituted by:
    a) a protected or non-protected amine function,
    ii) a protected or non-protected acid function,
    iii) a protected or non-protected alcohol function,
    iv) an aryl or heteroaryl group,
  the protected or non-protected side chain of an amino acid chosen from the natural or non-natural amino acids,
the substituents $R^1$, $R^3$, $R^4$, $R^5$, $R^7$, $R^8$, $R^9$, $R^{11}$ and $R^{12}$ represent a hydrogen atom,
starting from activated carbamic acid derivatives of formula (XXIV), as mentioned above, in which:
  i)—the substituents $R^2$, $R^6$ and $R^{10}$ have the meanings mentioned above and the substituents $R^1$, $R^3$, $R^4$, $R^5$, $R^7$, $R^8$, $R^{11}$ and $R^{12}$ represent a hydrogen atom, or
  the substituents $R^3$, $R^7$ and $R^{11}$ have the meanings mentioned previously for $R^2$, $R^6$ and $R^{10}$, and the substituents $R^1$, $R^2$, $R^4$, $R^5$, $R^6$, $R^8$, $R^{10}$ and $R^{12}$ represent a hydrogen atom,
  ii) the $R^9$ group is an arylalkyl or heteroarylalkyl group, which can be bonded to a solid support,
and allowing the formation, before the final deprotection step, of a synthesis intermediate having formula (XV), as mentioned above, in which the different substituents $R_1$ to $R^{12}$ have the same meanings as mentioned above for the compound of formula (XXIV).

The invention also concerns compounds of formulae (XV) or (XVIa) as mentioned above, in which the substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ represent:

either a hydrogen atom,
or the protected or non-protected side chain of an amino acid chosen from the natural or non-natural amino acids,
and in particular in which:
  $R^1$, $R^3$, $R^4$, $R^5$, $R^7$, $R^8$, $R^9$, $R^{11}$, $R^{12}$, $R^{13}$, $R^{15}$ and $R^{16}$ represent a hydrogen atom, and
  $R^2$, $R^6$, $R^{10}$ and $R^{14}$ represent a group chosen from the methyl, isopropyl, isobutyl, sec-butyl, benzyl, alkyl and hydroxybenzyl acetate (ortho, meta or para) groups,
subject to the compounds of formula (XV) or (XVIa) being different from the following compounds of formulae (VIII bis/1), (VIII bis/2), (VIII bis/3) and (VIII bis/4)

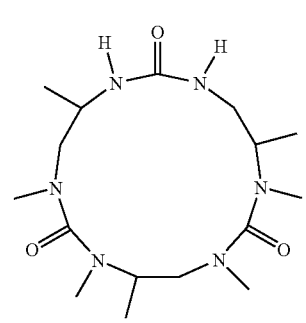

(VIII bis/1)

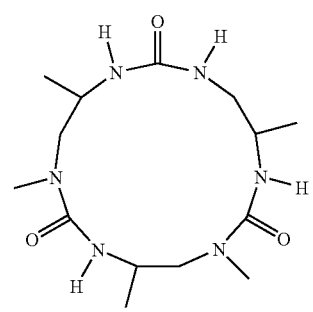

(VIII bis/2)

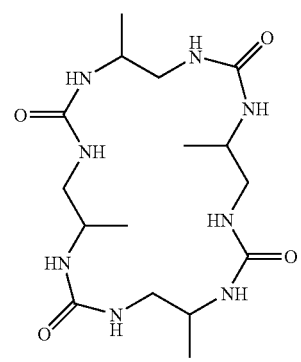

(VIII bis/3)

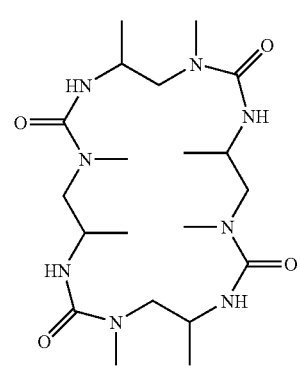

(VIII bis/4)

The invention also concerns compounds as defined above, corresponding to the following formulae:
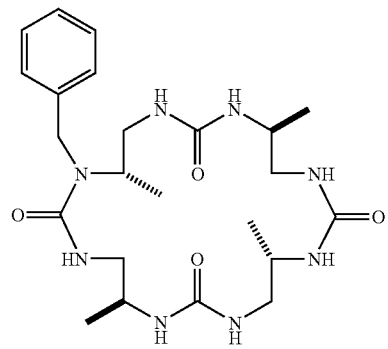
(XVIa-1)
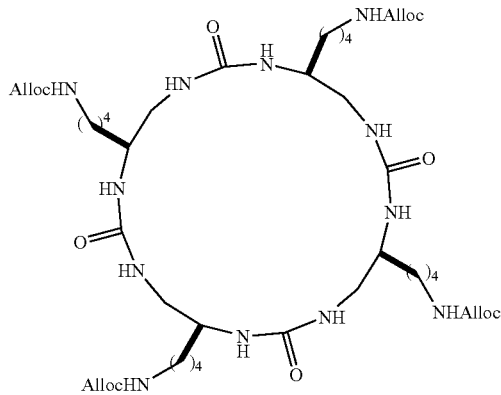
(XVIa-6)
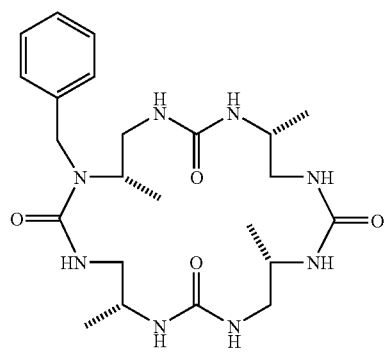
(XVIa-3)
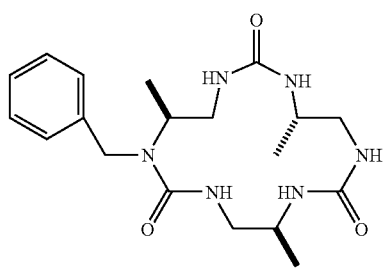
(XV-1)
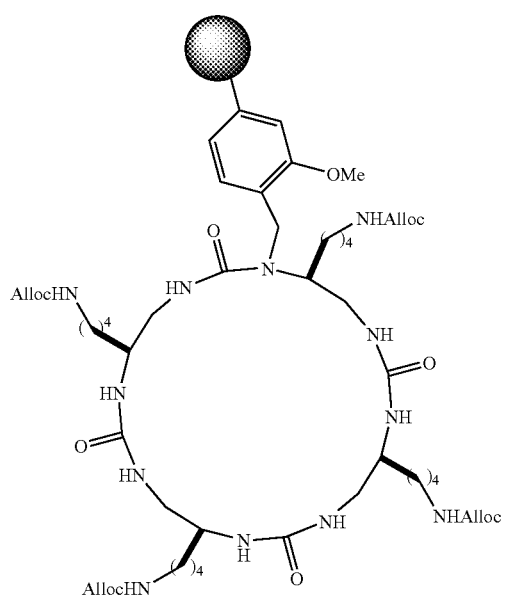
(XVIa-5)
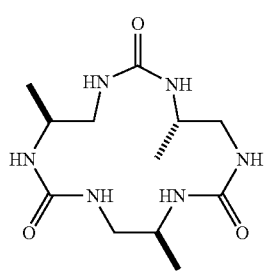
(XV-2)
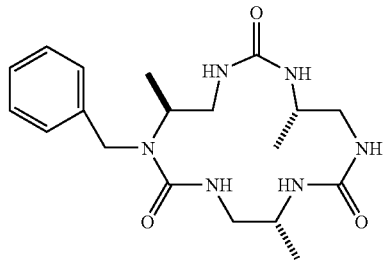
(XV-3)

-continued
(XV-4)
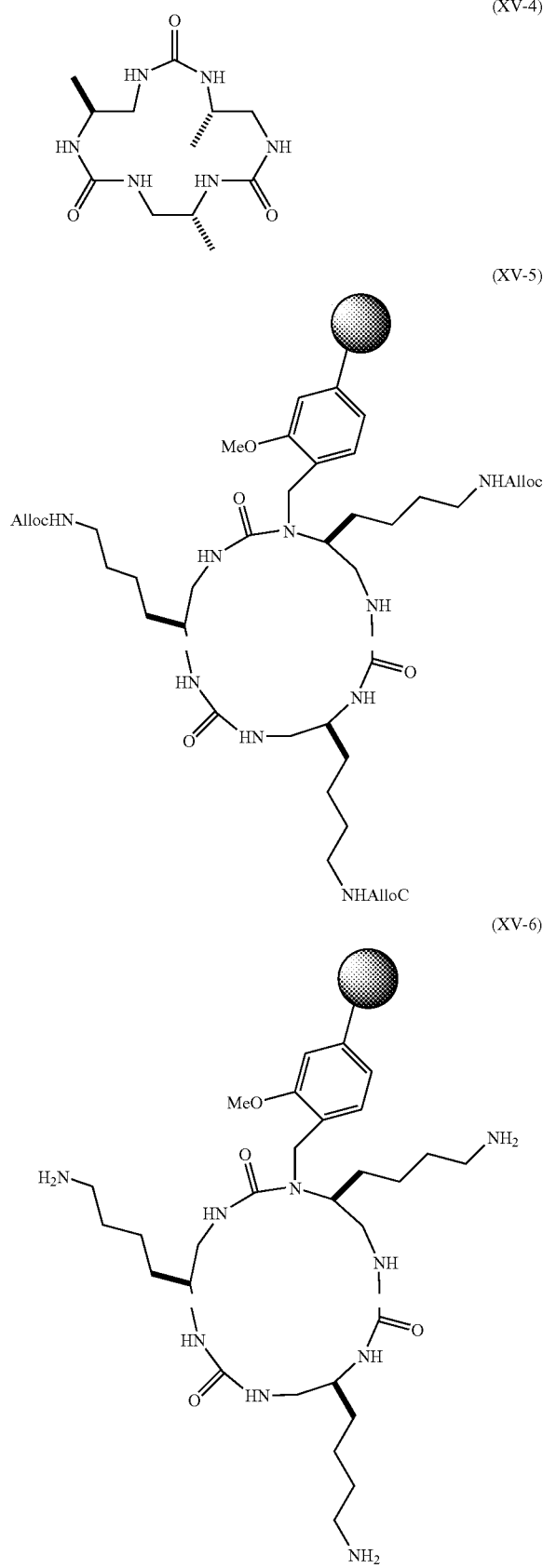
(XV-5)
(XV-6)
(XV-7)
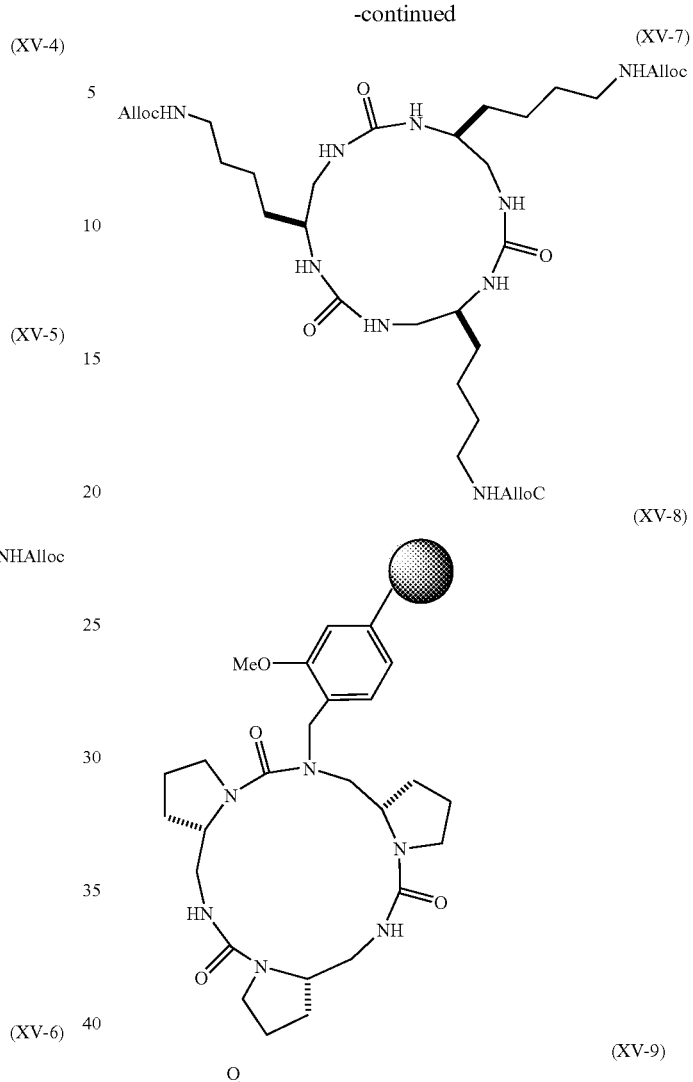
(XV-8)
(XV-9)
in which Alloc represents an allyloxycarbonyl group and
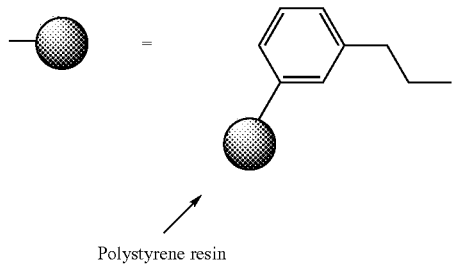
Polystyrene resin According to an advantageous embodiment, the preparation method of the present invention makes it possible in particular to obtain new cyclic urea compounds which would have been difficult to obtain using preparation methods of the prior art which generally require the preparation of diamines. The preparation method of the present invention allows the cyclisation of carbamic acid derivatives obtained from N-protected amino acid derivatives (α, β, γ and δ amino acids), and thus make it possible to obtain easily and in very few steps, a considerable molecular diversity on the side chains used. The method of the invention also applies to the cyclisation of carbamic acid derivatives obtained in only three steps, namely:

a) a step of transformation of the —COOH group of the N-protected amino acid derivative (α, β, γ and δ amino acids) into a —CON$_3$ group in order to obtain an acyl azide, b) a step of transformation of the —CON$_3$ group of the acyl azide into an —NCO group in order to obtain an isocyanate, c) a step of treatment of the isocyanate in order to obtain said stable carbamic acid derivative, from very simple molecules, such as the N-protected dipeptides, to give extremely functionalised and dissymetric cyclic urea molecules.

It should be recalled that the term "amino acid derivative" must be interpreted in the broad sense, as understood by the person skilled in the art, and designates in particular a peptide, polypeptide, protein, pseudopeptide or oligourea derivative.

BRIEF DESCRIPTION OF THE DRAWINGS

FIG. 1A corresponds to the view of the urea ring seen from above.

FIG. 1B corresponds to the view along the axis formed by the C$^α$ carbons, denoted C(1) and C(4).

Figure 1A:
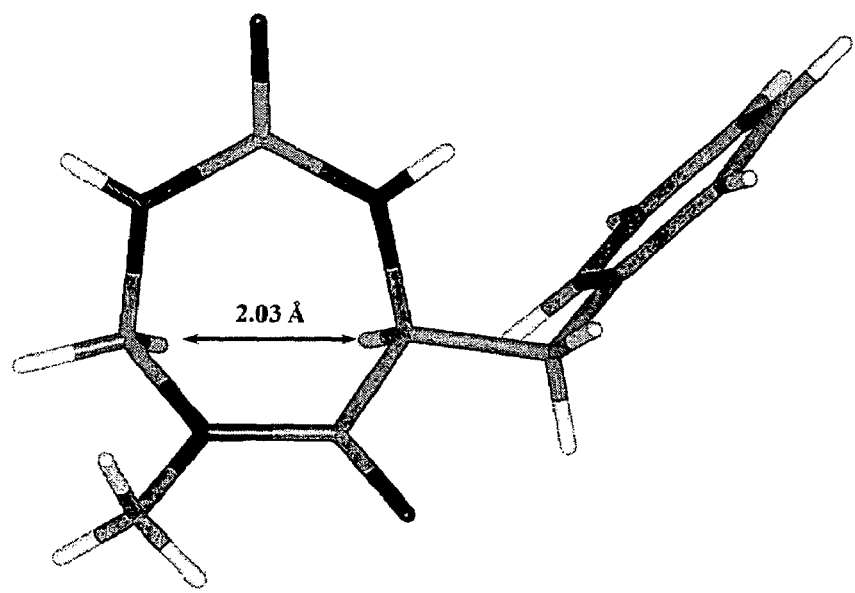
FIGS. 1A and 1B represent the two-dimensional structure of the compound of formula (Ij).

For greater clarity, the atoms have been numbered. The following tables indicate certain interatomic distances (in Å) and certain angle values.

Lengths of certain bonds in the compound of formula (Ij)

| Bond | Length (Å) |
| --- | --- |
| N(1)—C(3) | 1.32 |
| N(2)—C(12) | 1.32 |
| C(12)—N(3) | 1.38 |

Values of certain angles in the compound of formula (Ij)

| Angle | Value (°) |
| --- | --- |
| C(3)—N(1)—C(1) | 120 |
| N(1)—C(3)—C(4) | 119 |
| C(12)—N(2)—C(4) | 132 |
| N(2)—C(12)—N(3) | 119 |
| C(12)—N(3)—C(1) | 126 |

Values of certain angles in the compound of formula (Ij)

| Angle | Value (°) |
| --- | --- |
| N(3)—C(12)—N(2)—C(4) | 0.47 |
| C(1)—N(3)—C(12)—N(2) | −3.43 |
| C(4)—C(3)—N(1)—C(1) | −1.07 |

The following examples illustrate the invention. They do not limit it in any way.

EXAMPLE 1

Intermolecular and Intramolecular Reactions which can Occur During Preparation of the Cyclic Urea Compounds.

The process of macrocyclisation from homo-oligomeric and/or hetero-oligomeric bifunctional acyclic precursors (activated carbamic acid derivatives containing a primary or secondary amine function), can lead to the obtaining of homo-oligomeric and/or hetero-oligomeric cyclic urea compounds, whose size distribution depends on the dilution of the reaction medium and the effective molarity of the different linear precursors. It is the competition that exists between the intermolecular and intramolecular reaction processes that leads to the obtaining of a reaction mixture which can be more or less complex.

1) Use of a Stable Activated Carbamic Acid Derivative

When the carbamic acid derivative containing a primary or secondary amine function (precursor) in protonated form is reacted in the presence of a base, it is possible to obtain homo-oligomeric cyclic ureas of variable sizes, and in variable proportions.

Diagram 1 below represents the homo-oligomeric cyclic urea compounds obtained at the end of intermolecular and intramolecular reactions.

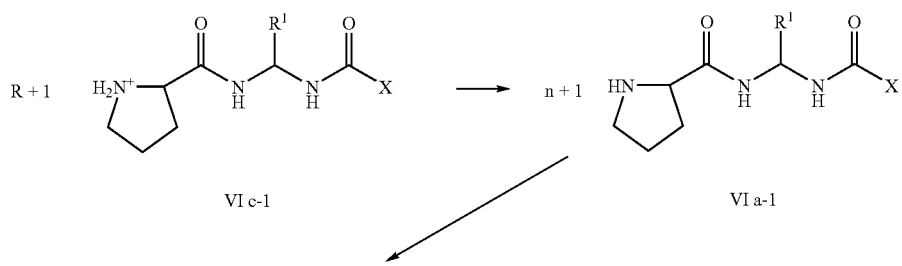

-continued

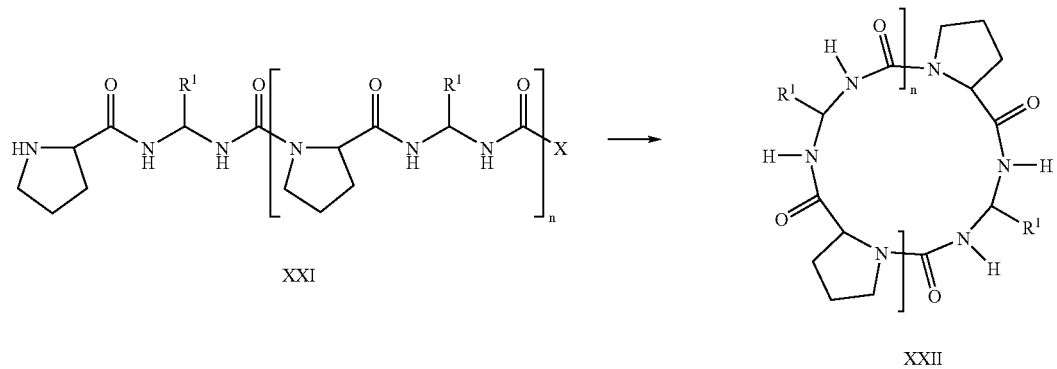

XXI

XXII

In this diagram, the secondary amine functions of the activated carbamic acid derivatives (bifunctional acyclic precursors) are represented in protonated form (VIc-1) and in free form (VIa-1).

When the initial compound is the bifunctional acyclic precursor (VIa-1) (activated carbamic acid derivative containing a secondary amine function in free form) obtained at the end of the release step, the intermolecular homo-oligomerisation reaction can take place directly after said release step, without the addition of a base.

When the initial compound is the bifunctional acyclic precursor (VIc-1) (activated carbamic acid derivative containing a secondary amine function in protonated form), the intermolecular homo-oligomerisation reaction takes place in the presence of a base, in order to neutralise the protonated secondary amine function into a secondary amine function in free form (VIa-1). At the end of the intermolecular homo-oligomerisation reaction, a bifunctional homo-oligomeric acyclic precursor containing a secondary amine function in free form (XXI) is obtained, which undergoes intramolecular cyclisation to form a homo-oligomeric cyclic urea (XXII). Thus, in the case where the precursor is the molecule (VIc-1) or (VIa-1), or the homo-oligomer (XXI), mass spectrometry of the reaction medium makes it possible to detect cyclic ureas (XXII) of variable sizes, from monomer to octamer, and represented by means of the integer n (n=an integer from 0 to 7). When n is equal to 0, there is no homo-oligomer formation, and the intramolecular cyclisation step b) takes place immediately after the formation of the compound (VIa-1).

In general, for this family of precursors, among the cyclic ureas present in the reaction medium, the cyclic dimer (n=1) is the main product.

It is thus possible, from a single precursor (stable activated carbamic acid derivative containing a primary or secondary amine function in free form or protonated form), to obtain a mixture of homo-oligomeric cyclic ureas having rings of different sizes. The cyclic ureas thus obtained can be characterised by mass spectrometry and purified by chromatography.

2) Use of Two Stable Activated Carbamic Acid Derivatives

It is also possible, from a mixture of several precursors of the same family, to obtain a statistical distribution, for different ring sizes, of hetero-oligomeric and homo-oligomeric cyclic ureas.

Diagram 2 below represents homodimeric (IIIf1) and (IIIf3), and heterodimeric (IIIf2) cyclic urea compounds obtained at the end of intermolecular and intramolecular reactions.

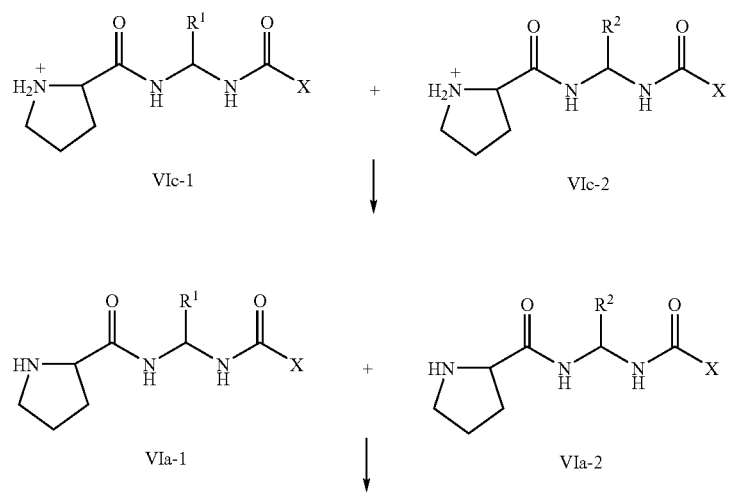

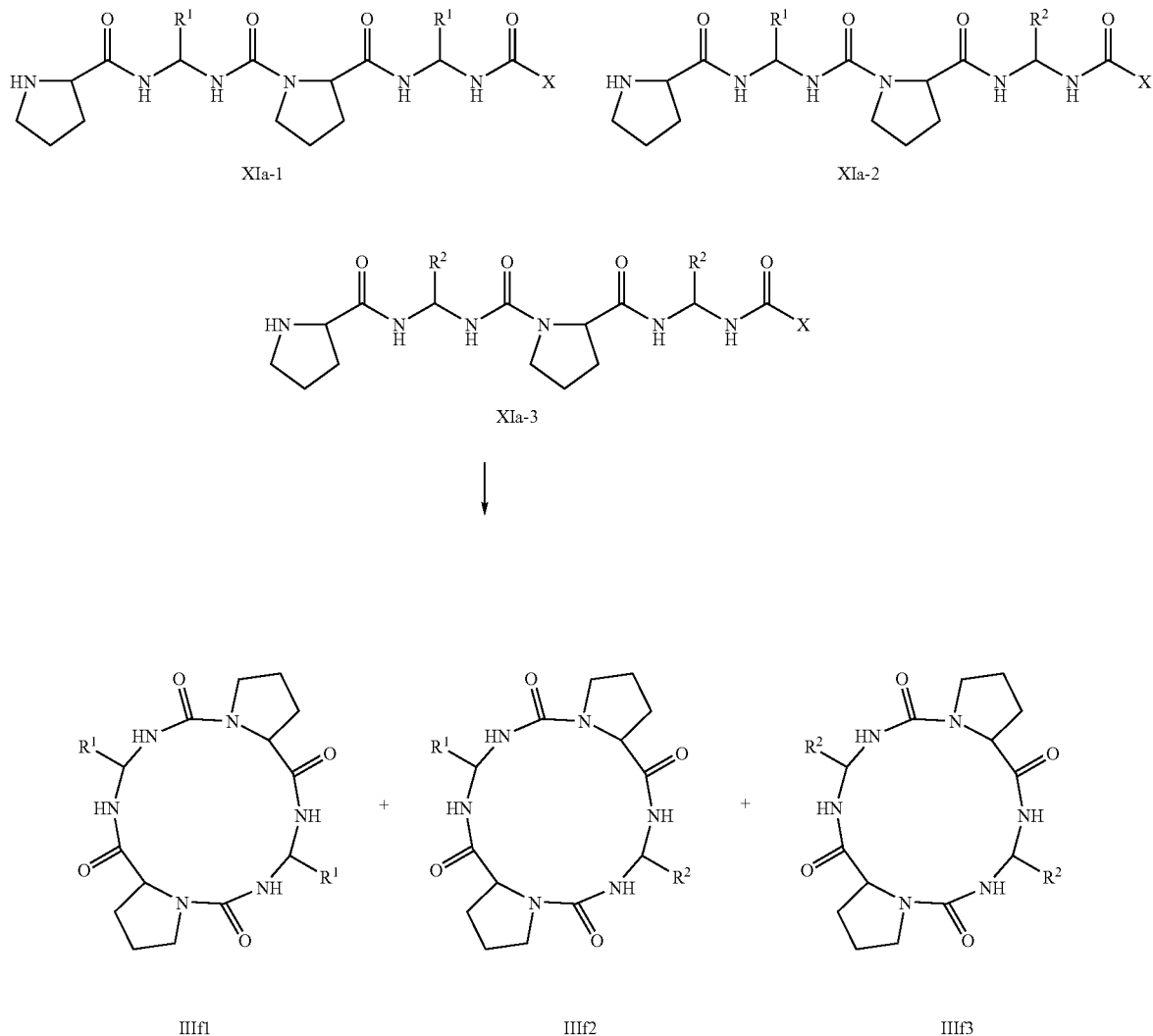

The secondary amine functions of the bifunctional acyclic precursors are represented in protonated form (VIc-1) and (VIc-2) and in free form (VIa-1) and (VIa-2).

The two bifunctional acyclic precursors (VIc-1) and (VIc-2) (activated carbamic acid derivatives containing a secondary amine function in protonated form) each, in the presence of a base, undergo homo-dimerisation to form two homodimeric bifunctional acyclic precursors (XIa-1) and (XIa-3) respectively, containing a secondary amine function in free form, as well as hetero-dimerisation to form a dimeric bifunctional precursor (XIa-2) containing a secondary amine function in free form.

Said homo-dimeric (XIa-1), (XIa-3) and heterodimeric (XIa-2) derivatives thus obtained undergo intramolecular cyclisation to form homodimeric cyclic ureas (IIIf1) and (IIIf3) and one heterodimeric cyclic urea (IIIf2) respectively.

Thus, if the reaction is carried out on a mixture of two precursors, (VIc-1), (VIc-2) or (VIa-1), (VIa-2), in the case of cyclic dimers, a heterodimer (IIIf2) and two homodimers (IIIf1) and (IIIf3) must statistically be formed.

EXAMPLE 3

Cleavage of the Activated Carbamic Acid Derivative Containing a Protected Amine Function in Relation to the Solid Support.

Diagram 3 below represents the cleavage, in relation to a solid support (a resin), of an activated carbamic acid of formula:

B—A—NH—CO—X in which

X represents a group conferring upon said derivative an activated carbamic acid function, B represents the protected amine function, A represents the part of the molecule separating the activated carbamic acid function and the protected amine function.

■ represents the solid support (resin).

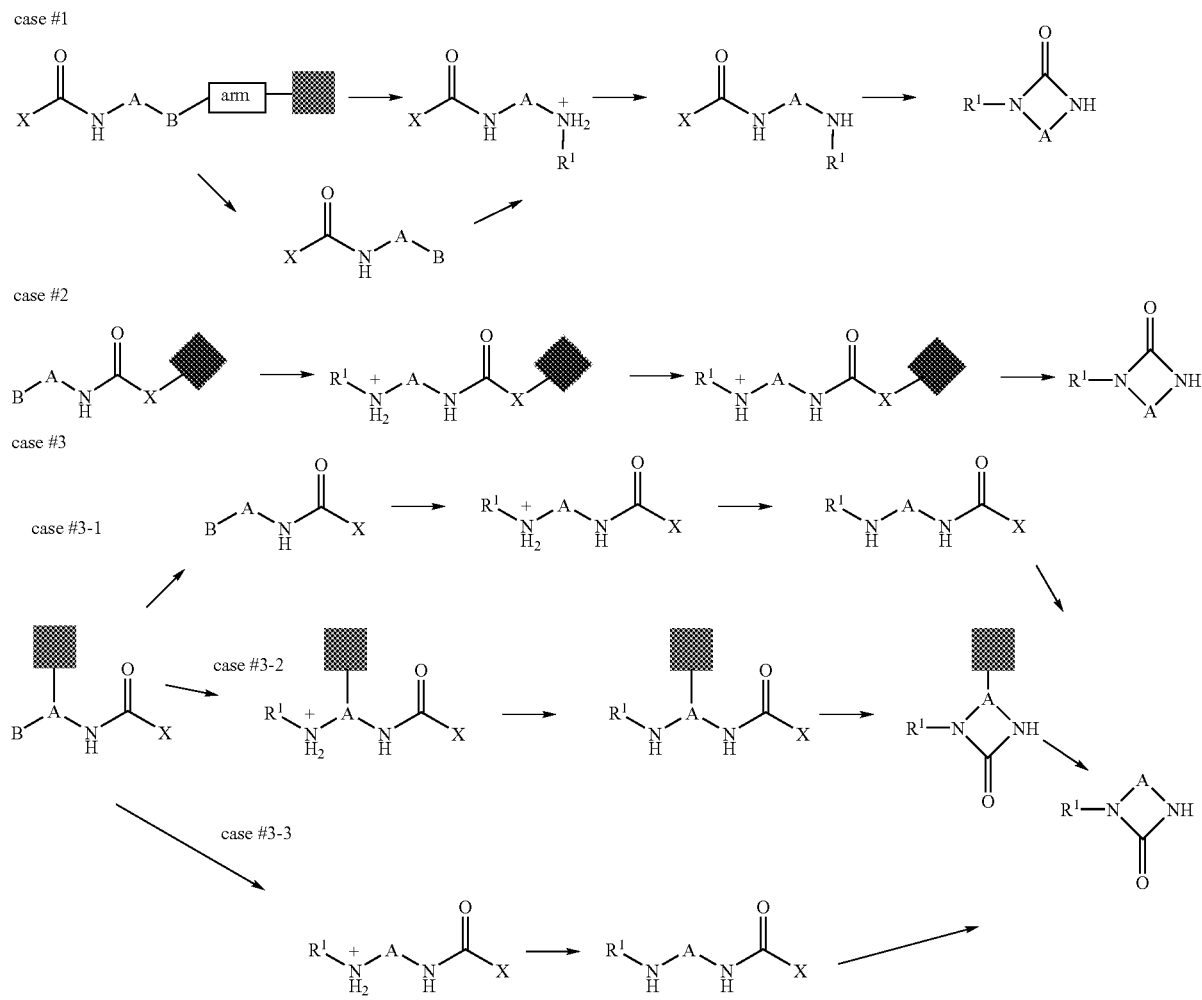

The activated carbamic acid derivative is chemically bonded to the resin either (1) by its amine function (the resin and the resin arm serving as protecting group) [case #1], or (2) by its activated carbamic acid function [case #2], or (3) by another functional group present in said activated carbamic acid derivative [case #3].

On the basis of the method of attachment of the activated carbamic acid derivative to the resin, the cleavage can be achieved either before the intramolecular cyclisation step (the cyclisation step will then be carried out in solution after cleavage) [case #1, case #2, case #3-1 and case #3-3] or after the cyclisation step (which will therefore take place on the solid support [case #3-2].

EXAMPLE 4

Method for Preparation of Cyclic Urea Compounds from N-Boc Protected Carbamic Acid Derivatives (XVII) and (XIX).

The selectivity of the deprotection of the amine function is dependent on the type of protecting group used for the amine and on the activated carbamic acid group. Such an example of orthogonality (namely the selective release of the amine function so as not to alter the carbamic acid function of the activated carbamic acid derivative) is shown below by the selective deprotection of the Boc (ter-butoxycarbonyl) group which does not alter the integrity of the O-succinimidyl carbamate (XVII), and (XIX). In effect the O-succinimidyl carbamate is not degraded in the presence of trifluoroacetic acid or hydrochloric acid in organic solvent: the step of release of the amine function (via deprotection of the Boc group) is thus completely selective.

This example is by no means exhaustive. It is possible to imagine other types of orthogonality such as the use of the benzyloxycarbonyl group with O-succinimidyl carbamate.

1) Step of release or deprotection of the protected amine function of the stable activated carbamic acid derivatives (XVII) and (XIX) leading respectively to carbamic acid derivatives containing a primary or secondary amine function in protonated form (XVIIIa) and (VIc-3), or in free form (XVIIIb) or (VIa-3).

Studies have shown that the N-hydroxysuccinimide carbamate was stable in an acid medium (treatment with trifluoroacetic acid (TFA) for example). The carbamic acid derivatives of N-hydroxysuccinimide (XVII) and (XIX) represented in diagram 4 below have been synthesised as described previously, namely by:

a step of transformation of the —COOH group of the corresponding N-protected amino acid derivative into a —CON$_3$ group in order to obtain an acyl azide,

- a step of transformation of the corresponding —CON₃ group of the acyl azide into a —NCO group in order to obtain an isocyanate,
- a step of treatment of the corresponding isocyanate in order to obtain the carbamic acid derivative of N-hydroxysuccinimide of formula (XVII) or (XIX).

The diagrams of synthesis of the activated carbamic acid derivatives of N-hydrosuccinimide (XVII) and (XIX) are respectively represented below:

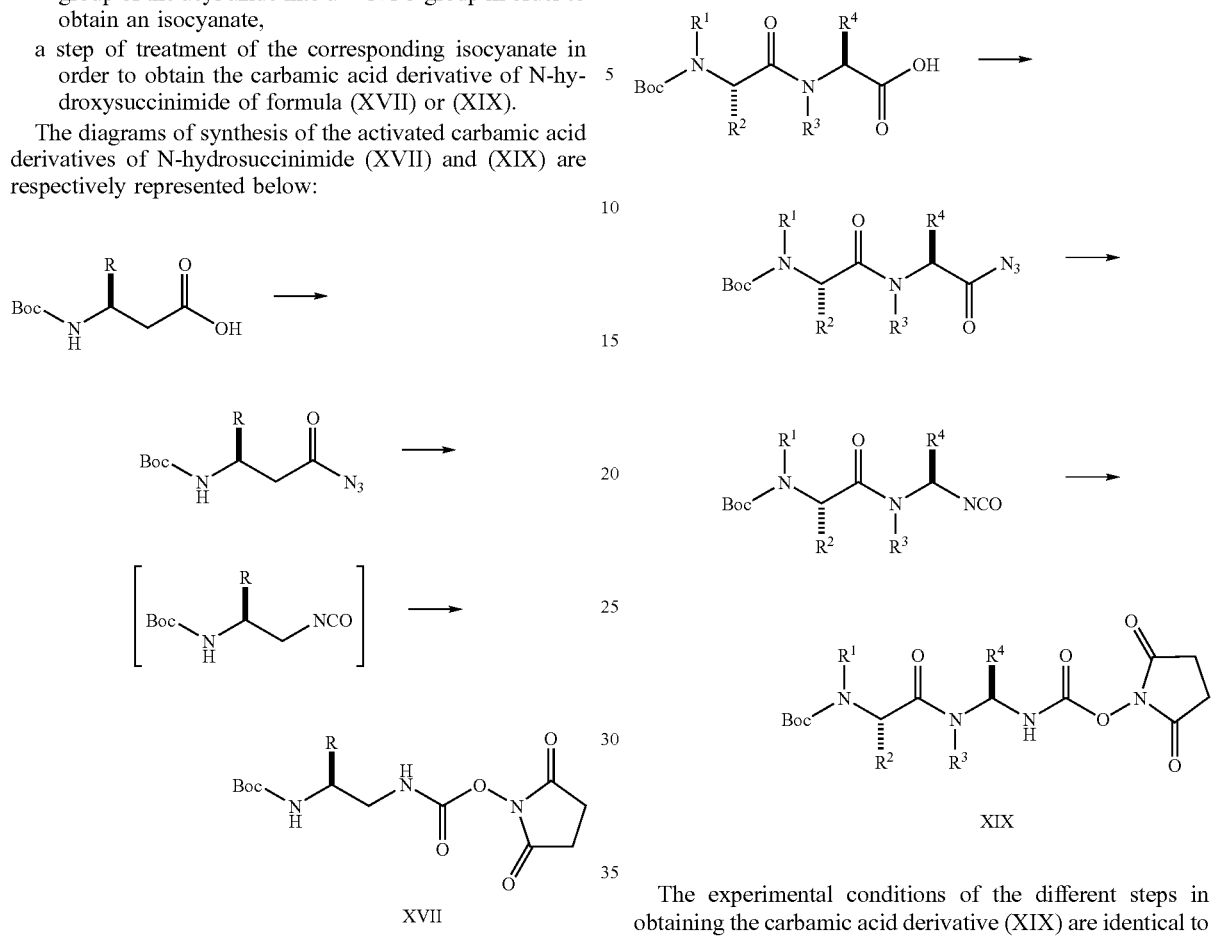

The experimental conditions of the different steps in obtaining the carbamic acid derivative (XVII) are described in the publication of Guichard et al., "J. Org. Chem., 1999, 64, 8702–8705".

The experimental conditions of the different steps in obtaining the carbamic acid derivative (XIX) are identical to those described for the compound (XVII).

Diagram 4 below represents the selective deprotection by the trifluoroacetic acid (TFA) of the Boc group of the N-protected carbamic acid (XVII) and (XIX) and succinimidyl derivatives.

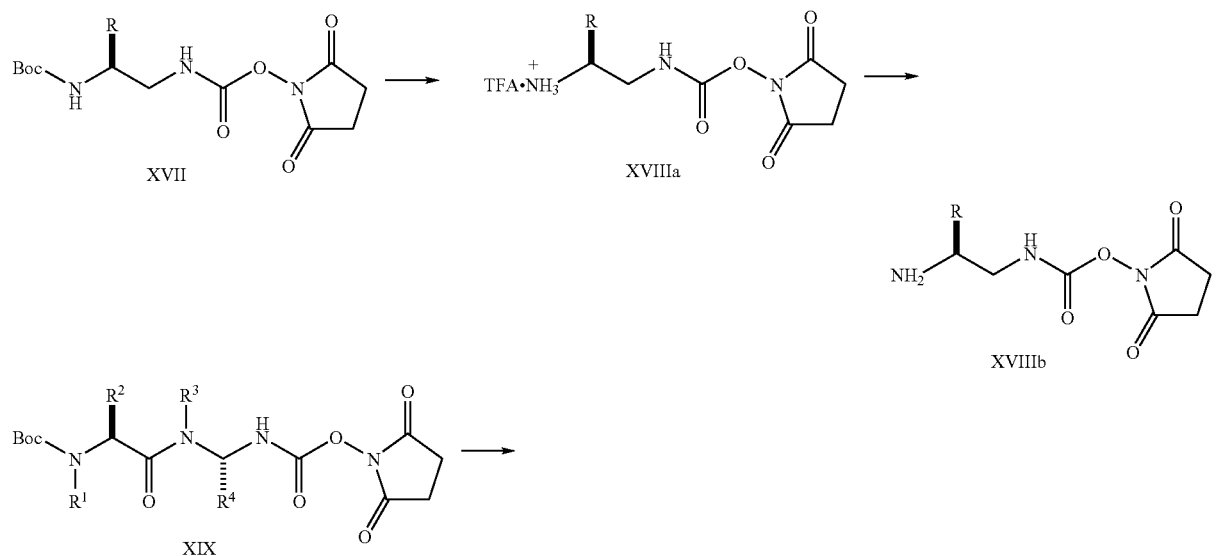

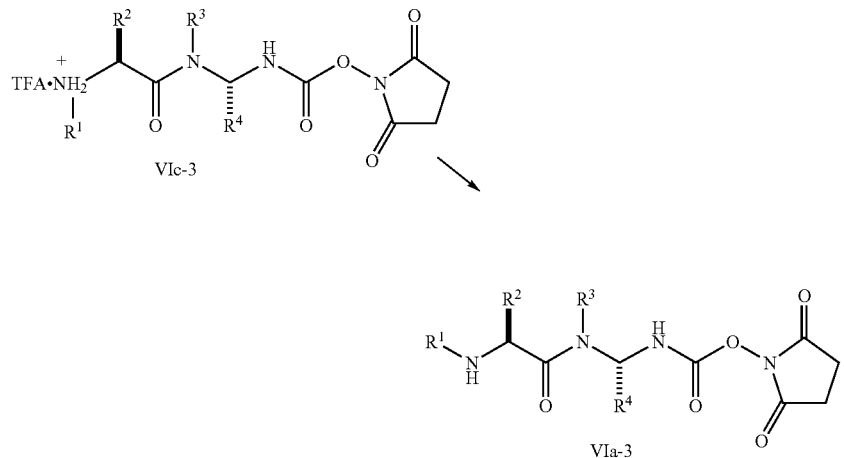

The treatment of the N-Boc protected carbamates (XVII) and (XIX) by TFA makes it possible to obtain the intermediate compounds (XVIIIa) and (VIc-3) (trifluoroacetate salts which can be isolated), or (XVIIIb) and (VIa-3) (which cannot be isolated) which represent precursors of interest for the synthesis of cyclic urea compounds.

The N-Boc protected carbamic acid derivatives (XVII) and (XIX) are each dissolved in a solution of trifluoroacetic acid ($CF_3COOH$ or TFA) (deprotection solvent) containing methylene chloride ($CH_2Cl_2$) (50/50 v/v for example), or in a solution of pure TFA. After 30 minutes, the TFA is evaporated or coevaporated in the presence of ether ($Et_2O$) or hexane. In a certain number of cases, the addition of ether or hexane leads to a precipitate which is filtered and dried under vacuum. Otherwise, the residual oil after evaporation of the TFA is dried under vacuum.

2) Step of intramolecular cyclisation of the precursor compounds (XVIIIb) and (VIa-3).

The TFA salts (XVIIIa) and (VIc-3) previously isolated are each dissolved or suspended in a volume of solvent (for example of acetonitrile (MeCN)) (cyclisation solvent) to achieve a dilution ranging from approximately 0.0001M to approximately 0.1M. A tertiary base (at least one equivalent to neutralise the amine salt formed during the deprotection step), for example diisopropylethylamine, N-methylmorpholine, triethylamine ($Et_3N$), lutidine or collidine (pure or diluted in an organic solvent such as MeCN) is added (either dropwise, or directly) to the trifluoroacetate salt solution over a period of time that may be up to 24 hours.

Compounds (XVIIIb) and (VIa-3) thus obtained react intramolecularly to give corresponding cyclic urea compounds which possess different ring sizes.

The reaction is followed by high performance liquid chromatography (HPLC). When there is no further reaction, the solvent is evaporated and the residue is purified either by inverse phase HPLC, or by flash chromatography on silica, or by recrystallisation in an appropriate solvent to give the expected cyclic urea compound or compounds.

Diagrams 5 to 11 below represent respectively:

the step of release of the protected amine function of a stable activated carbamic acid derivative corresponding to general formula (XVII) or (XIX) and, the step of intramolecular cyclisation from the carbamic acid derivative thus obtained containing an amine function in free form.

Diagram 5: Preparation of the Cyclic Urea Compound (XX).

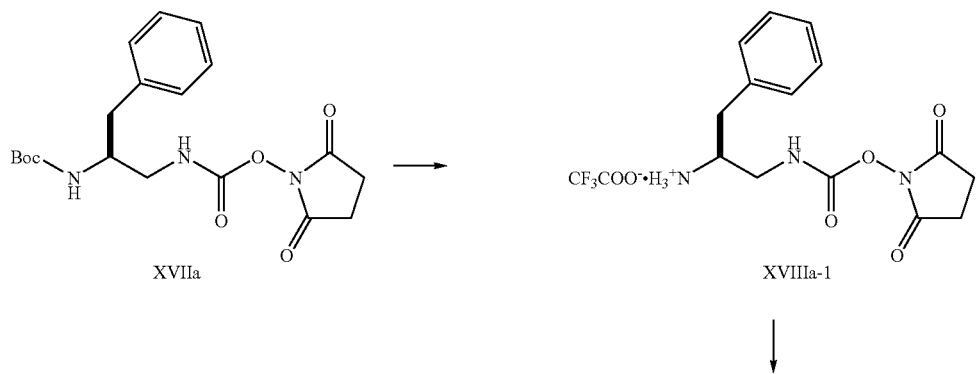

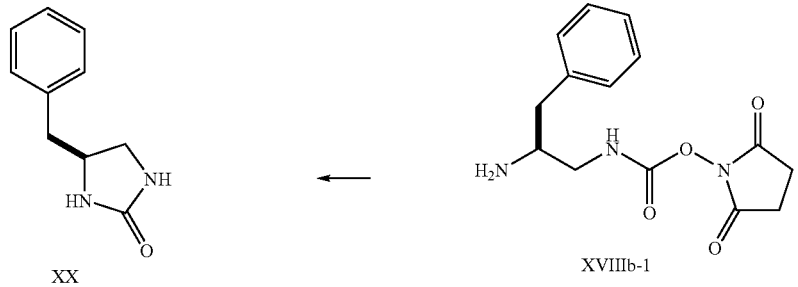

1) Compound (XVIIa) (323 mg, 0.8 mmol) is dissolved in 10 ml of a TFA/CH$_2$Cl$_2$ (50/50 v/v) mixture, and the solution is agitated at ambient temperature for 30 minutes. The solvent is then concentrated and the TFA salt (XVIIIa-1) is precipitated by addition of hexane. The precipitate is filtered and dried using a vane pump for 12 hours to give a white solid (XVIIIa-1) (300 mg, 93%).

2) Compound (XVIIIa-1) (300 mg, 0.72 mmol) is dissolved in MeCN (10 ml) and a solution of diisopropylethylamine (130 µl, 0.73 mmol) is added. The reaction mixture is agitated for 60 minutes. MeCN is evaporated and the residue is redissolved with ethyl acetate. The organic phase is washed with a saturated NaCl solution to give the compound (XX) (110 mg, 87%).

In the case of carbamic acid derivative (XVIIa) (βamino acid derivative), the cyclic compound (XX) obtained after deprotection of the Boc group and intramolecular cyclisation, comprises a 5-atom ring. This compound has been previously described in the literature.

This example has been given in order to show that the method for preparation of the present invention makes it possible to obtain cyclic urea compounds already described in the literature.

Diagram 6: Preparation of the Cyclic Urea Compound (IIIf-4).

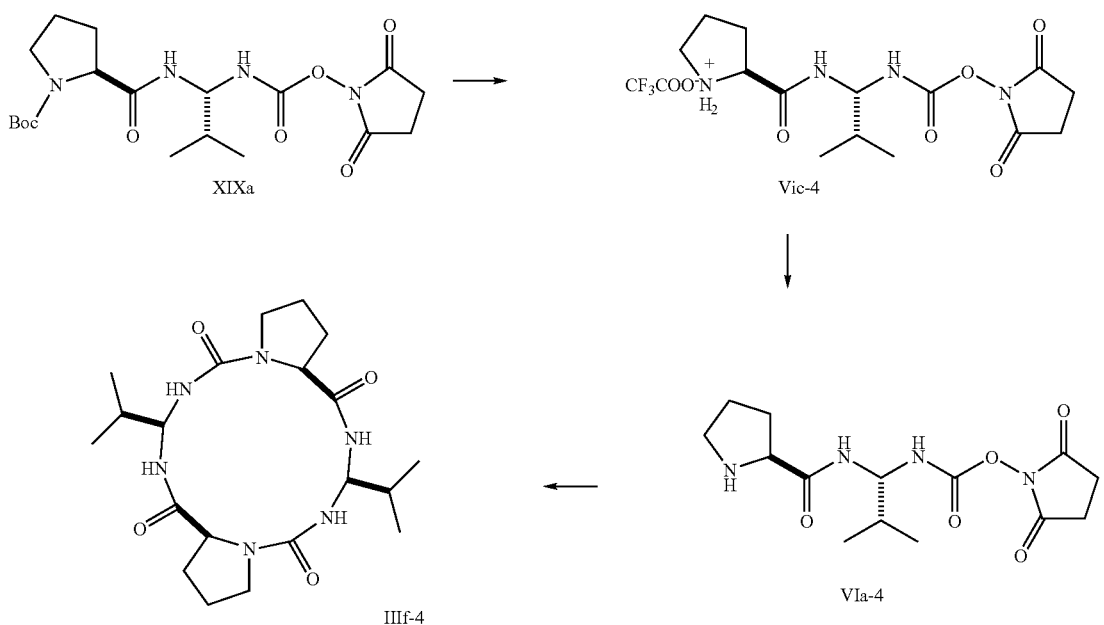

1) Compound (XIXa) (500 mg, 1.17 mmol) is dissolved in 10 ml of a TFA/CH$_2$Cl$_2$ (50/50 v/v) mixture, and the solution is agitated at ambient temperature for 30 minutes. The solvent is then concentrated and the TFA salt (VIc-4) is precipitated by addition of ether. The precipitate is filtered and dried using a vane pump for 12 hours to give a white solid (VIc-4) (450 mg, 87%).

2) Compound (VIc-4) (430 mg, 0.97 mmol) is dissolved in 80 ml MeCN and the solution is added dropwise to a solution of diisopropylethylamine (421 µl, 2.4 mmol) in MeCN (500 ml) for 1 hour. The reaction mixture is agitated for 5 hours. MeCN is evaporated and the residue taken up in CH$_2$Cl$_2$. The organic phase is washed with 1N KHSO$_4$, dried over MgSO$_4$, and concentrated. The residue is purified by inverse phase chromatography using a C18 column to give the compound (IIIf-4) (140 mg, 70%).

In the case of the carbamic acid derivative (XIXa), a dipeptide derivative for which the amide bond is not in cis configuration, a 14-atom cyclic dimer (IIIf-4) is mainly obtained, with a yield of 70% (diagram 6).

Compound (IIIf-4) is new.

Diagram 7: Preparation of the Compound (Ii).

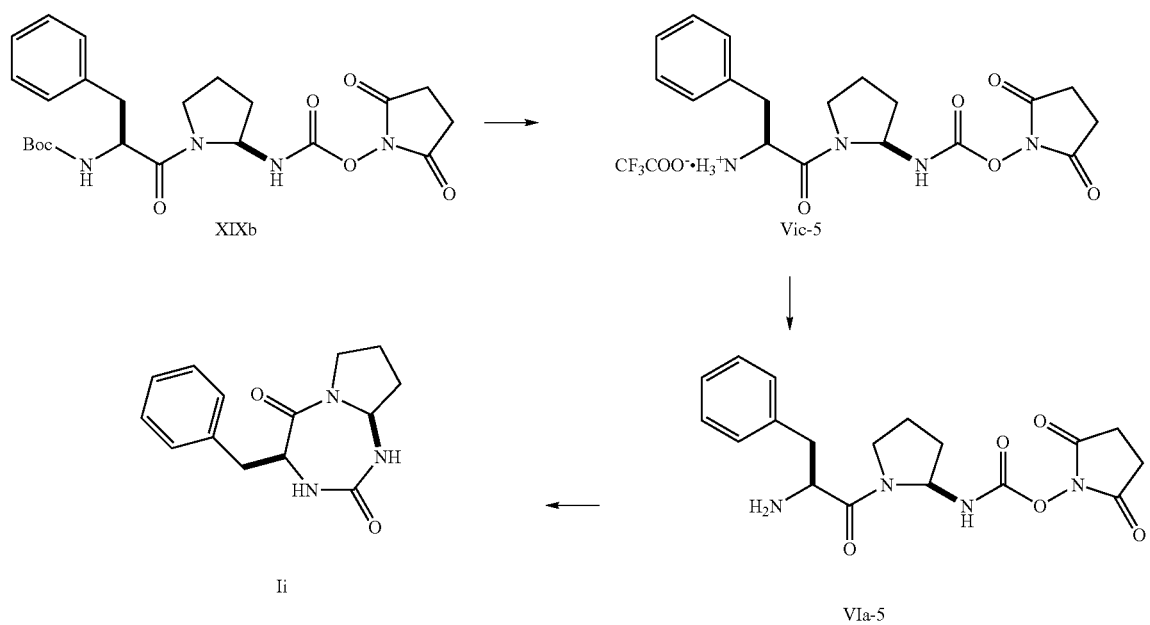

In the case of the carbamic acid derivative (XIXb), for which the amide bond can adopt a cis configuration, the corresponding 7-atom cyclic monomer (Ii) is obtained with a yield greater than 70% (diagram 7).

Compound (Ii) is new.

Diagram 8: Preparation of the Compound (Ij).

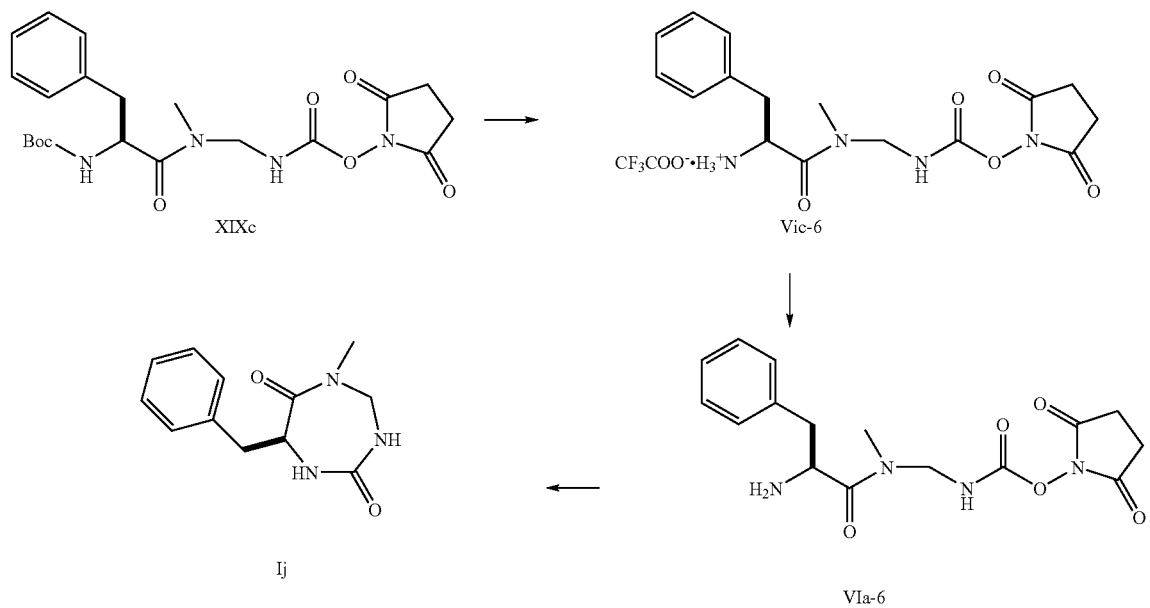

1) Compound (XIXc) (3 g, 6.91 mmol) is dissolved in 20 ml of a TFA/CH$_2$Cl$_2$ (50/50 v/v) mixture, and the solution is agitated at ambient temperature for 30 minutes. The solvent is then concentrated and the TFA salt (VIc-6) dried using a vane pump for 12 hours to give a solid foam (VIc-6) (3.23 g, 100%).

2) Compound (VIc-6) (400 mg, 0.89 mmol) is dissolved in MeCN (30 ml) and the solution is added dropwise to a solution of diisopropylethylamine (353 ml, 2.0 mmol) in MeCN (40 ml) at −20° C. for 1 hour. The reaction mixture is agitated for 3 hours. MeCN is evaporated and the residue is recrystallised in a CH$_2$Cl$_2$/diisopropylether mixture to give (Ij) (135 mg, 70%).

Diagram 9: Preparation of the Compound (Ik).

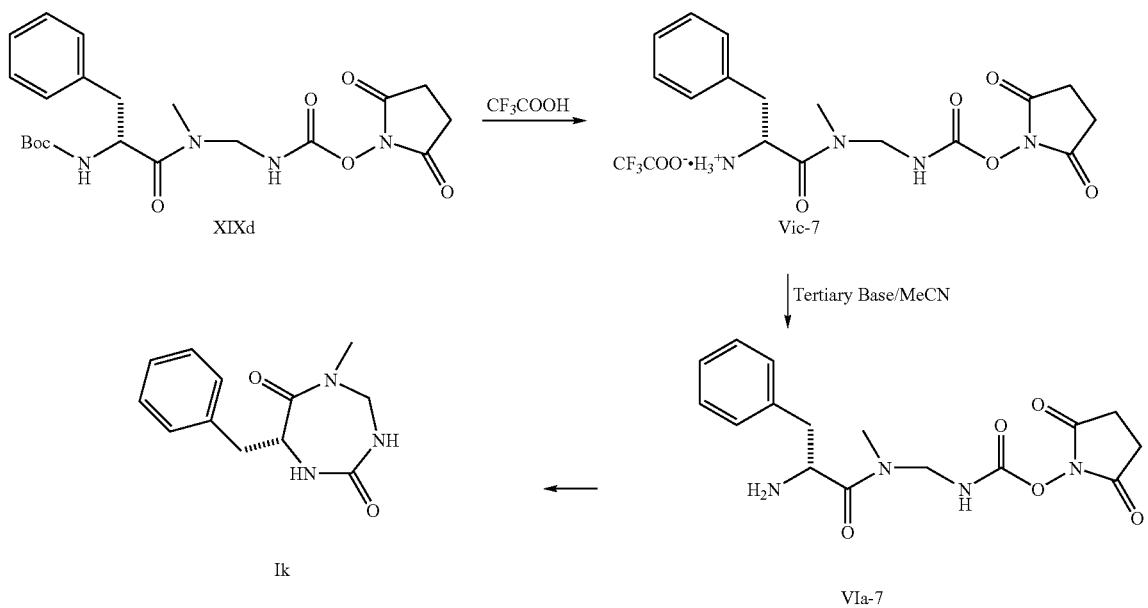

1) Compound (XIXd) (2.02 g, 4.49 mmol) is dissolved in trifluoroacetic acid (v=10 ml) for 30 minutes. The precipitate formed by the addition of diethylether is collected on frit, washed with ether and dried with a vane pump for 12 hours to give a white solid (VIc-7): 1.98 g, 95%.

2) Compound (VIc-7) (1.94 g, 4.17 mmol) is dissolved in MeCN (90 ml) and the solution is added dropwise to a solution of diisopropylethyl amine (1.78 ml, 10.42 mmol) in MeCN (50 ml) at ambient temperature for 4 hours. MeCN is evaporated and the residue is recrystallised in a $CH_2Cl_2$/diisopropylether mixture to give (Ik) (586 mg, 60%).

Diagram 10: Preparation of the Compound (II).

1) Compound (XIXe) (1.21 g, 2.55 mmol) is dissolved in trifluoroacetic acid (v=10 ml) for 30 minutes. The precipitate formed by the addition of diethyl ether is collected on frit, washed with ether and dried with a vane pump for 12 hours to give a white solid (VIc-8): (816 mg, 65%).

2) Compound (VIc-8) (200 mg, 0.41 mmol) is dissolved in MeCN (20 ml) and the solution is added dropwise to a solution of diisopropylethyl amine (0.21 ml, 1.23 mmol) in MeCN (100 ml) at ambient temperature for 4 hours. MeCN is evaporated and the residue is purified by preparative HPLC to give (II) after lyophilisation (70 mg, 66%).

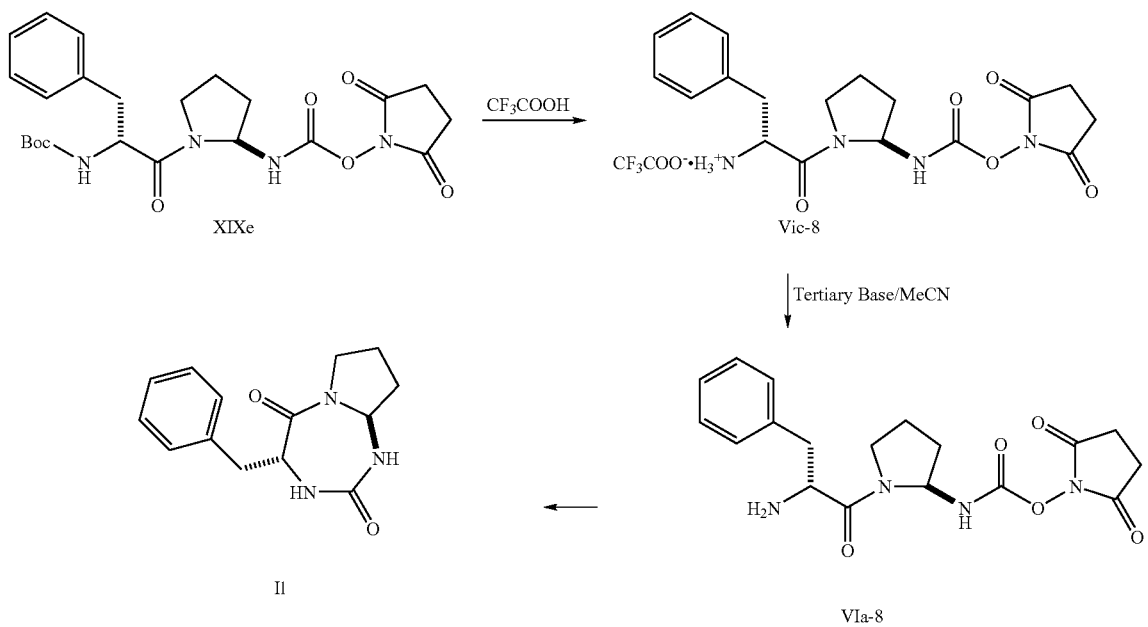

Diagram 11: Preparation of the Compound (Im).

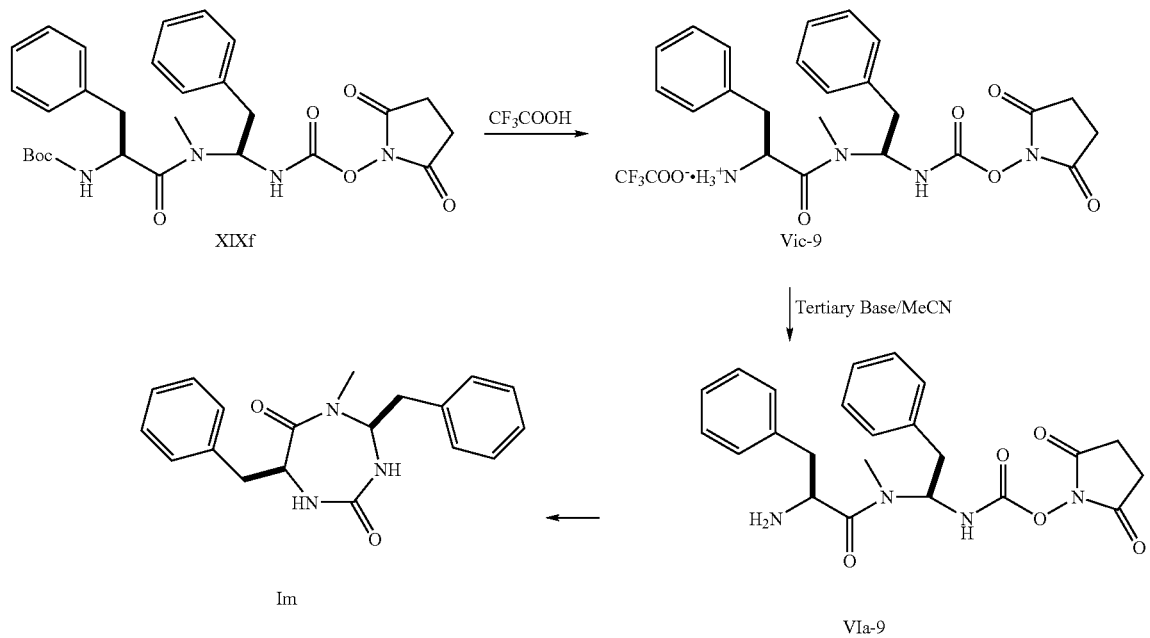

1) Compound (XIXf) (1.05 g, 1.95 mmol) is dissolved in trifluoroacetic acid (v=10 ml) for 30 minutes. The precipitate formed by the addition of diethyl ether is collected on frit, washed with ether and dried with a vane pump for 12 hours to give a white solid (VIc-9): (1,045 mg, 97%).

2) Compound (VIc-9) (200 mg, 0.36 mmol) is dissolved in MeCN (20 ml) and the solution is added dropwise to a solution of diisopropylethyl amine (0.19 ml, 1.08 mmol) in MeCN (100 ml) at ambient temperature for 4 hours. MeCN is evaporated and $CH_2Cl_2$ (1.5 ml) is added. The cyclic urea derivative is then purified by treatment with a "scavenger" resin (Tris-(2-aminoethyl)-amine polystyrene) to give (Im): (116 mg, 99%).

TABLE 1

| Carbamates (XVII) or (XIX) | Cyclic ureas | Yield (%)[a] | HPLC Rt (min)[b] | MALDI-MS |
|---|---|---|---|---|
| (XVIIa) | (XX) | 90 | 11.2[c] | 177.2 [M + H]+ |
| (XIXa) | (IIIf-4) | 70 | 10.00[d] | 367.4 [M + H]+ |
| (XIXb) | (Ii) | 70 | 10.03[d] | 260.3 [M + H]+ |
| (XIXc) | (Ij) | 70 | 9.39[d] | 234.5 [M + H]+ |
| (XIXd) | (Ik) | 60 | 9.22[d] | 234.3 [M + H]+ |
| (XIXe) | (Il) | 66 | 9.55[d] | 260.4 [M + H]+ |
| (XIXf) | (Im) | 99 | 7.88[d] | 324.2 [M + H]+ | cyclic urea compounds (XX), (IIIf-4), (Ii), (Ij), (Ik), (Il) and (Im) obtained from the stable activated carbamic acid derivatives (XVIIa), (XIXa), (XIXb), (XIXc), (XIXd), (XIXe) and (XIXf) respectively.
[a]yields of the cyclic urea compounds (XX), (IIIf-4), (Ii), (Ij), (Ik), (Il) and (Im)
[b]linear gradient of A (aqueous solution containing 0.1% TFA) and B (acetonitrile solution containing 0.08% TFA),
[c]5–65% B, 20 min (passing from 5% to 65% of B in 20 min),
[d]0–100% B, 20 min.
HPLC: high performance liquid chromatography
MALDI-MA: mass spectrometry The physico-chemical data of compounds (IIIf-4), (Ii), (Ij) and (Ik) are given below.

(IIIf-4): Yield 70% white solid; HPLC $t_r$ 10.0 min (linear gradient, 0–100% B, 20 min)—$^1$H NMR ([D$_6$]DMSO, 200 MHz): δ=0.86 (d, J=6.8 Hz, 6H, Me), 0.86 (d, J=6.7 Hz, 6H, Me), 1.59–1.70 (m, 2H, CH(Me)$_2$), 1.76–2.11 (m, 1H, CHCH$_2$CH$_2$), 3.14–3.26 (m, 1H, CH$_2$N), 3.49–3.60 (m, 1H, CH$_2$N), 4.80 (m, 1H, NHCHNH), 5.58 (d, J=8.9 Hz, NCONH), 6.48 (d, J=6.5 Hz, CH$_2$CONH).

(Ii): Yield 70% white solid; HPLC $t_r$ 10.0 min (linear gradient, 0–100% B, 20 min)—$^1$H NMR ([D$_6$]DMSO, 200 MHz): δ=1.89–2.29 (m, 4H, CHCH$_2$CH$_2$), 2.78 (dd, J=8.7, 14.5 Hz, 1H, CH$_2$Ph), 3.37 (dd, J=5.4, 14.4 Hz, 1H, CH$_2$Ph), 3.45–3.55 (m, 1H, CH$_2$N), 3.75–3.86 (m, 1H, CH$_2$N), 4.59 (hept, J=2.7, 5.6, 8.5), 4.84 (s, 1H, NH), 5.46 (br q, J=, 3.3 Hz, 1H, NCHNH), 6.4 (s, 1H, NH), 7.20–7.35 (m, 5 arom. H).

(Ij): Yield 80% white solid; HPLC $t_r$ 9.39 min (linear gradient, 0–100% B, 20 min)—$^1$H NMR ([D$_6$]DMSO, 400 MHz): δ=6.18 (s, H, NHPhe, 1H), 5.17 (d, $^\alpha$CH-gem-Sar, 1H), 4.77 (m, $^\alpha$CH Phe, 1H), 4.10 (dd, $^\alpha$CH-gem-Sar, 1H).

(Ik): Yield 90% white solid; HPLC $t_r$ 9.22 min (linear gradient, 0–100% B, 20 min)—$^1$H NMR ([D$_6$]DMSO, 400 MHz): δ=6.18 (s, H, NHPhe, 1H), 5.17 (d, $^\alpha$CH-gem-Sar, 1H), 4.77 (m, $^\alpha$CH Phe, 1H), 4.10 (dd, $^\alpha$CH-gem-Sar, 1H).

EXAMPLE 5

Preparation of Cyclic Urea Compounds by Mono- or Di-Alkylation of the Cyclic Urea Compounds (Ij)

1) Preparation of the Compounds (In), (Io), (Ip) and (Iq) by Dialkylation of (Ij)

General method: to a solution of (Ij) (1 equivalent) in distilled THF is added NaH (5 equivalents) then the electrophile (RX, 3 equivalents). The reaction mixture is agitated for 3 to 48 hours. The reaction is followed by RP-HPLC using a C18 column. At the end of the reaction, ethyl acetate is added and the organic phase is washed with NH$_4$Cl. To eliminate the surplus electrophile, if this is not volatile, and if purification on silica is not desirable, a "scavenger" resin can be used, such as (mercaptoethyl) aminoethylpolystyrene resin for example. In this case, the "scavenger" resin (approximately 10 equivalents) is added to the reaction medium and the mixture is agitated for 48 hours. At the end of this treatment, the resin is eliminated by filtration and the organic phase is washed with NH$_4$Cl, dried and concentrated to give the desired purified product as shown in diagram 12.

Diagram 12

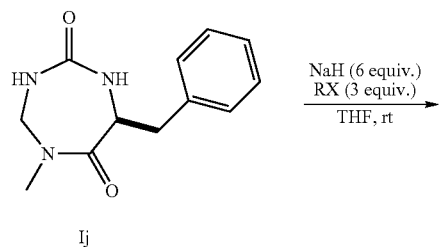

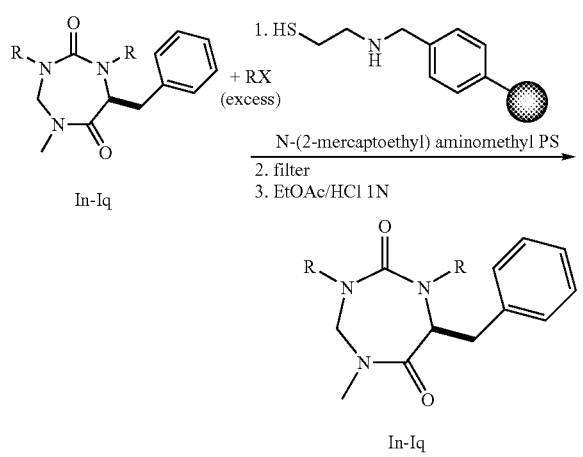

For the compounds (In), (Io), (Ip) and (Iq) the R group represents respectively: a methyl (Me) group, a —CH$_2$COOtBu group, a Bn (—CH$_2$—Φ) group and a BnOBn group.

TABLE 2

| Product | RX | "Scavenger" resin | Purity (%) | Yield (%) | HPLC $t_R$ (min)[a] |
|---|---|---|---|---|---|
| In | MeI | no | 95 | 99 | 10.66[b] |
| Io | BrCH$_2$COOtBu | yes | 94 | 95 | 15.82[b] |
| Ip | BnBr | yes | 94 | 90 | 16.30[b] |
| Iq | BnOBnBr + NaI | yes | 86 | 96 | 16.44[c] |

[a]gradient of A (0.1% TFA in H$_2$O) and B (MeCN containing 0.08% TFA).
[b]0–100% B, 20 min.
[c]30–100% B, 20 min.

2) Preparation of the Compounds (Ir), (Is), and (It) by Monoalkylation of (Ij)

General method: to a solution of (Ij) (1 equivalent) in a distilled anhydrous solvent (THF, MeCN or CH$_2$Cl$_2$) is added potassium fluoride on alumina (40 w/w) (10 equivalents) followed by the electrophile (RX, between 1 and 20 equivalents). The reaction mixture is agitated for 20 to 72 hours. The reaction is followed by RP-HPLC using a C18 column. At the end of the reaction the potassium fluoride on alumina is eliminated by filtration. To eliminate the surplus electrophile, if this is not volatile, and if purification on silica is not desirable, a "scavenger" resin can be used, such as (mercaptoethyl)aminoethylpolystyrene resin for example. In this case the "scavenger" resin (approximately 10 equivalents) is added to the reaction medium and the mixture is agitated for 48 hours. At the end of this treatment, the resin is eliminated by filtration and the organic phase is concentrated to give the desired purified product as shown in diagram 13 and in table 3. It is possible, under the best conditions (approximately 1 RX equivalent, reaction time of 48 h, see table 3), in order to obtain a selectivity of mono-alkylated product relative to di-alkylated product of the order of 93:7.

Diagram 13:

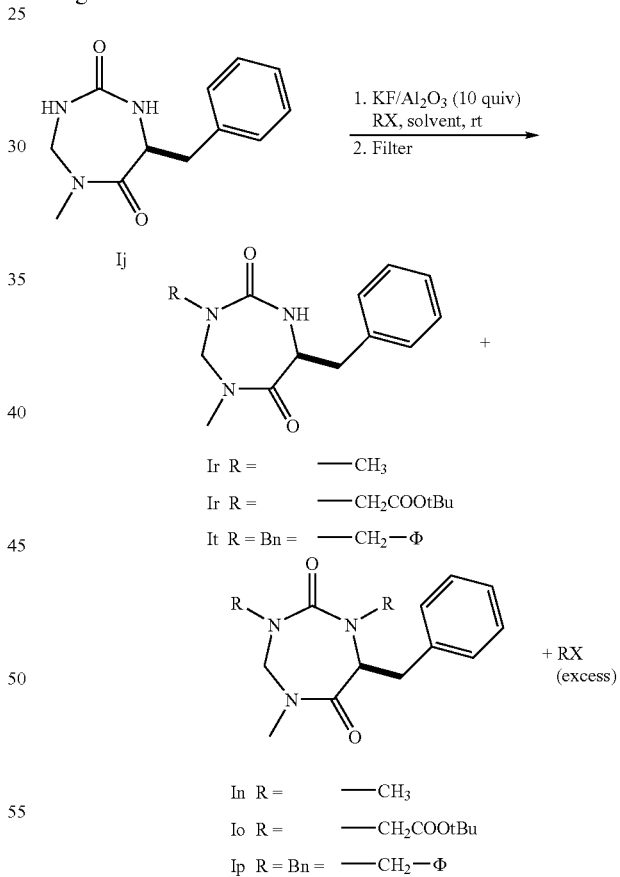

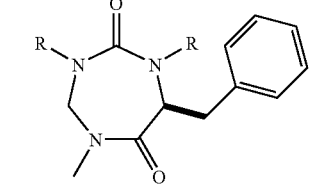

TABLE 3

| RX | eq. | solvent | time (hours) | Mono-: Di- alkylated | Overall purity (mono + di) | HPLC $t_R$ (mono/di) (min)[d] |
|---|---|---|---|---|---|---|
| MeI | 1.05 | THF | 48 h | 93:7 | 70[c] | 10.08/10.65 |
| MeI | 20 | MeCN | 72 h | 10:90 | 92 | |

TABLE 3-continued

| RX | eq. | solvent | time (hours) | Mono-: Di- alkylated | Overall purity (mono + di) | HPLC $t_R$ (mono/di) (min)[d] |
|---|---|---|---|---|---|---|
| BrCH$_2$COOtBu | 1.0 | THF | 48 | 93:7 | 87[a,d] | 12.73/15.79 |
| BrCH$_2$COOtBu | 1.5 | THF | 48 | 93:7 | 93[a] | |
| BrCH$_2$COOtBu | 10 | MeCN | 20 | 89:11 | 67[a] | |
| BnBr | 2 | DMF | 20 | Difficult reaction | — | 13.18/16.17 |
| BnBr | 2 | THF | 72 | 72:28 | 96[a] | |
| BnBr | 1.05 | THF | 48 | 87:13 | 87[a] | |
| BnBr | 1.05 | MeCN | 72 | 83:17 | 87[a] | |
| BnBr | 1 | CH$_2$Cl$_2$ | 48 | 94:6 | 74[a,b] | |

[a] after treatment with N-(2-mercaptoethyl)aminomethylpolystyrene resin.
[b] 6% of the initial product Ij is present.
[c] 0% of the initial product Ij is present.
[d] 10% of the initial product Ij is present.
[e] gradient of A (0.1% TFA in H$_2$O) and B (MeCN containing 0.08% TFA). 0–100% B, 20 min.

EXAMPLE 6

Structural Properties of Cyclic Urea Compounds (I)

Figure 1B:
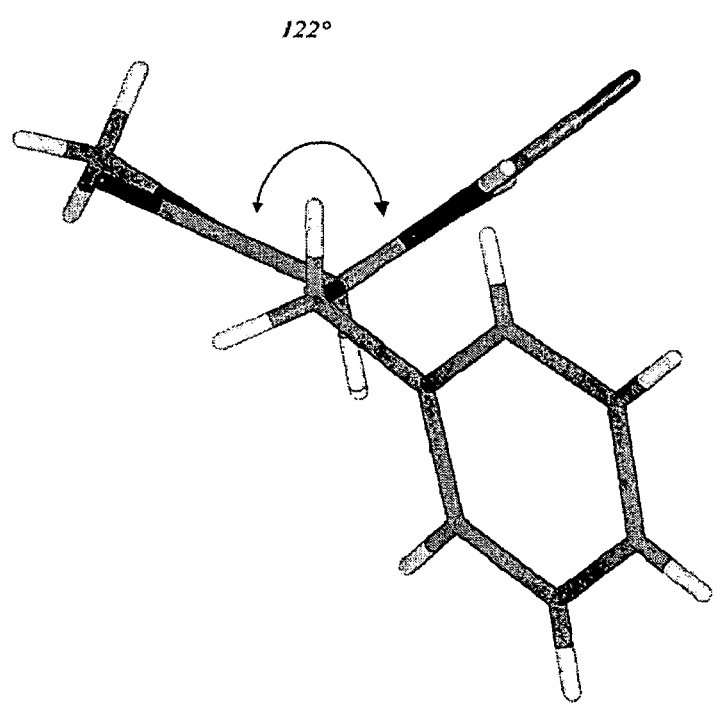

Cyclic urea compounds (I) have an extremely constrained structure, well defined on the basis of X-ray diffraction or of NMR. Knowledge of this structure is extremely useful for use of the heterocyclic platform based on the compounds (I) for the design and discovery of new compounds of pharmacological interest. The structure of (Ij) (see FIGS. 1A and 1B) has been obtained by X-ray diffraction and is representative of the structure of the compounds (I). This structure is in keeping with that obtained for the same compound by two-dimensional NMR and by modelling. The 1,3,5-triazepine-2,6-dione ring has a strongly folded conformation. The planes of the two amide and urea groups meet along a line joining the alpha carbon of the gem-Sarcosine residue (—N(CH$_3$)—$^\alpha$CH$_2$—NH—) and the alpha carbon of the phenylalanine with a dihedral angle of 120°. By way of comparison, in the case of the most folded diketopiperazines, the dihedral angle defined by the amide planes is of the order of 140–160°. Moreover, the hydrogen atoms in axial positions on the alpha carbon of the gem-Sarcosine residue and the alpha carbon of the phenylalanine are spatially extremely close: they are separated by only 2.03 angstroms. By way of comparison, the distance between the protons situated on the alpha carbons in the folded diketopiperazines is of the order of 2.7–2.8 angstroms.

EXAMPLE 7

Preparation of Compounds (XV) and (XVIa) According to Diagrams 14 to 20.

The reaction sequence leading to the obtaining of compound (XVIa-2) is represented in diagram 14 and the detailed procedure is given below.

Diagram 14

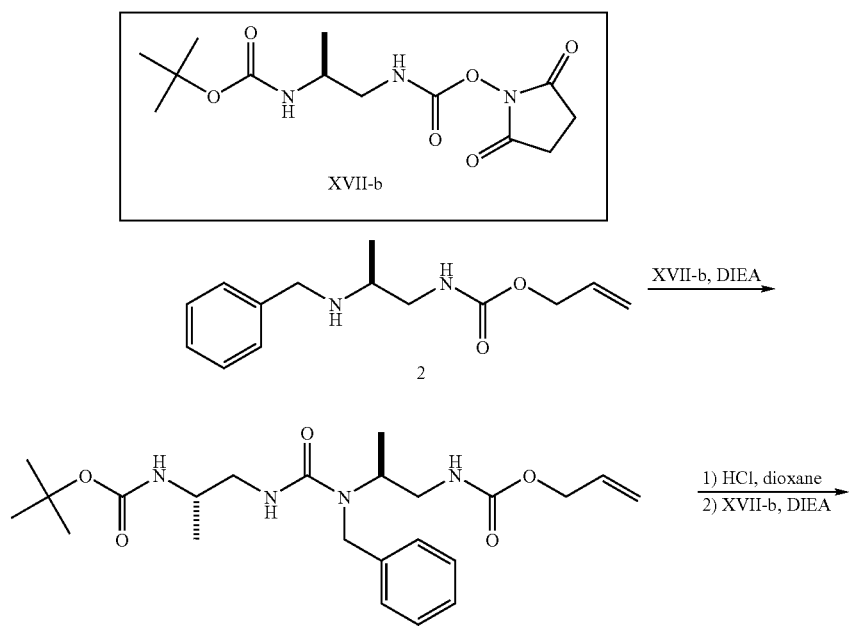

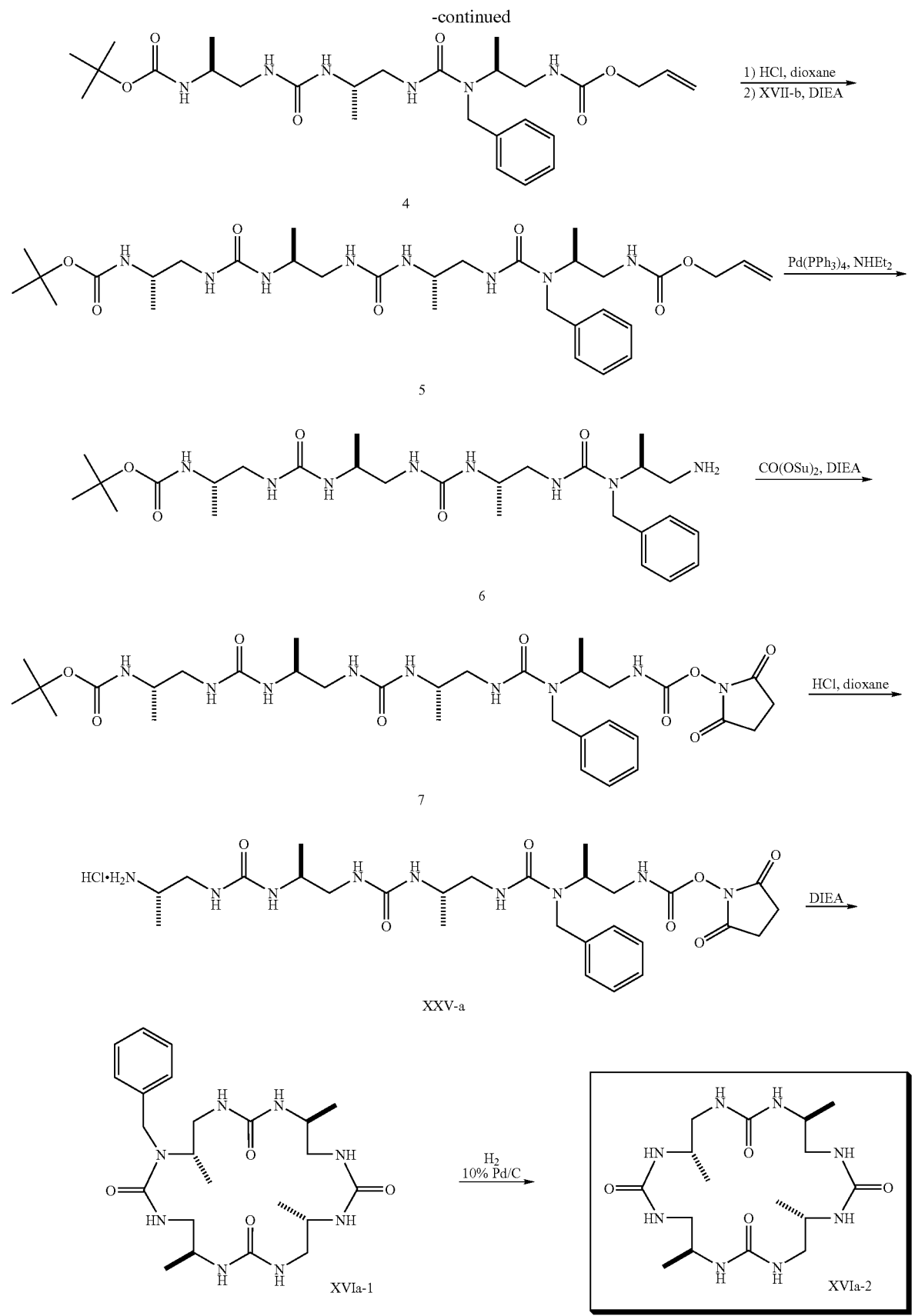

To a solution of compound 2 (see formula above, in diagram 14) (930 mg; 3.74.10$^{-3}$ mol) in acetonitrile (5 ml), is added DIEA (1.27 ml: 7.48.10$^{-3}$ mol) then compound (XVII-b) (1.18 g; 3.74.10$^{-3}$ mol). The reaction is followed by TLC. After 30 minutes, the acetonitrile is evaporated and the residue placed in ethyl acetate, followed by washing with 1N KHSO$_4$, saturated NaHCO$_3$, and finally saturated NaCl solutions consecutively. The organic phase thus obtained is dried (Na$_2$SO4) and evaporated. The residue is subjected to chromatography on silica with an AcOEt/Hexane 50/50 system, to obtain compound 3. Yield 74% (1.26 g). Translucent oil. HPLC $t_R$ 14.89 min (linear gradient, 20–80 B, 20 min).

Compound 3 (650 mg, 1.45.10$^{-3}$ mol) is deprotected by addition of trifluoroacetic acid (3 ml) with agitation. The latter is eliminated by successive coevaporations using hexane, until a residue is obtained, which is then dried. The product thus obtained is rendered soluble in acetonitrile (5 ml). DIEA (246 µl; 1.45.10$^{-3}$ mol) then compound (XVII-b) (457 mg; 1.45.10$^{-3}$ mol) is added. The reaction is followed by TLC. After 30 minutes, the acetonitrile is evaporated and the residue taken up in ethyl acetate, and washed by IN KHSO$_4$, saturated NaHCO$_3$, and finally saturated NaCl solutions consecutively. The organic phase thus obtained is dried (Na$_2$SO4) and evaporated, to obtain compound 4. Yield 87% (700 mg). HPLC $t_R$ 13.72 min (linear gradient, 20–80 B, 20 min); MS (MALDI-TOF) m/z 548.46 [M+H]$^+$, 571.31 [M+Na]$^+$, 587.81 [M+K]$^+$.

Compound 4 (640 mg; 1.17.10$^{-3}$ mol) is deprotected by addition of trifluoroacetic acid (3 ml) under agitation. The latter is eliminated by successive coevaporations using hexane, until a residue is obtained, which is then dried. The product thus obtained is rendered soluble in acetonitrile (5 ml). DIEA (199 µl; 1.17.10$^{-3}$ mol) then compound (XVII-b) (368 mg; 1.17.10$^{-3}$ mol) are added. The reaction is,followed by TLC. After 30 minutes, the acetonitrile is evaporated and the residue taken up in ethyl acetate, and washed with 1N KHSO$_4$, saturated NaHCO$_3$, and finally saturated NaCl solutions consecutively. The organic phase thus obtained is dried (Na$_2$SO4) and evaporated, to obtain compound 5. Yield 70% (530 mg). HPLC $t_R$ 13.62 min (linear gradient, 20–80 B, 20 min); MS (MALDI-TOF) m/z 671.17 [M+Na]$^+$, 687.68 [M+K]$^+$.

To a solution of compound 5 (460 mg; 7.09.10$^{-4}$ mol) in dichloromethane (5 ml), is added 1% mol Pd(PPh$_3$)$_4$ (8.2 mg; 7.09.10$^{-6}$ mol) followed by NHEt$_2$ (600 µl; 4.25.10$^{-3}$ mol). The reaction is followed by TLC. After 30 minutes, the dichloromethane is evaporated. The residue is placed in water (50 ml) with 1% acetic acid, and washed twice with AcOEt then lyophilised, in order to obtain compound 6. Quantitative yield (446 mg). HPLC $t_R$ 7.40 min (linear gradient, 20–100 B, 20 min); MS (MALDI-TOF) m/z 565.68 [M+H]$^+$, 587.38 [M+Na]$^+$.

A solution of compound 6 (75.5 mg; 1.34.10$^{-3}$ mol) in acetonitrile (400 µl) is prepared. In parallel, a solution of succinimidyl carbonate (69 mg; 2.68.10$^{-3}$ mol) in 2.69 ml acetonitrile is prepared. 50 ml of the succinimidyl carbonate solution in the solution of 6 is added 8 times, followed by the addition of approximately 6 µl of DIEA. After the last addition, the mixture is agitated for one hour and then evaporated. Compound 7 is then obtained. HPLC $t_R$ 11.32 min (linear gradient, 20–80 B, 20 min); MS (MALDI-TOF) m/z 729.03 [M+Na]$^+$, 745.31 [M+K]$^+$.

In a first phase, compound 7 is deprotected using HCl in dioxane to give (XXV-a). The mixture is coevaporated several times and the residue dried. Then, to a solution of DIEA (442 µl; 2.68.10$^{-3}$ mol) in 100 ml acetonitrile, a solution of product (XXV-a) previously obtained, in 10 ml of acetonitrile, is added dropwise over one hour. The mixture is evaporated and purified by preparative HPLC (linear gradient 0–80) to give (XVIa-1). HPLC $t_R$ 7.56 min (linear gradient, 20–80 B, 20 min); MS (MALDI-TOF) m/z 491.02 [M+H]$^+$, 513.46 [M+Na]$^+$, 529.66 [M+K]$^+$.

To a solution of (XVIa-1) (42 mg, 8.57.10$^{-3}$ mol) in ethanol (10 ml), palladium on charcoal is added. After two hours of reaction under 1 atm of H$_2$, filtration is carried out on Celite® followed by evaporation. The aggregate is placed in 1 ml of TFA until rendered partially soluble, then approximately 20 ml water is added. The whole is centrifuged and the supernatant lyophilised. Compound (XVIa-2) is then obtained. Yield (73%, 25 mg). White powder. HPLC $t_R$ 9.34 min (linear gradient, 0–100 B, 20 min); MS (MALDI-TOF) m/z 401.19 [M+H]$^+$; $^1$H NMR (500 MHz, CDCl$_3$+TFA, 333 K) δ 1.22 (d, 12H), 3.07 (br s, 4H), 3.39 (br d, 4 H), 3.91 (br s, 4H).

In the same way, compounds (XV-1) and (XV-2), (XVIa-3) and (XVIa-4), (XVIa-5) and (XVIa-6), (XV-3) and (XV-4), (XV-5), (XV-6) and (XV-7), (XV-8) and (XV-9) are synthesised as indicated in diagrams 15 to 20 respectively.

Diagram 15

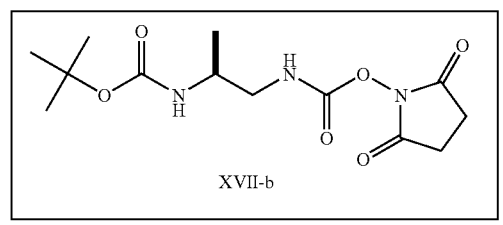

XVII-b

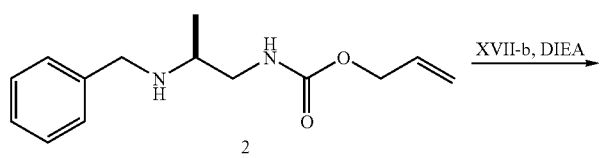

XVII-b, DIEA

2

-continued
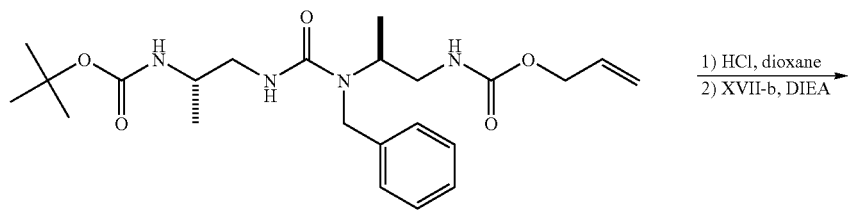
3
1) HCl, dioxane
2) XVII-b, DIEA
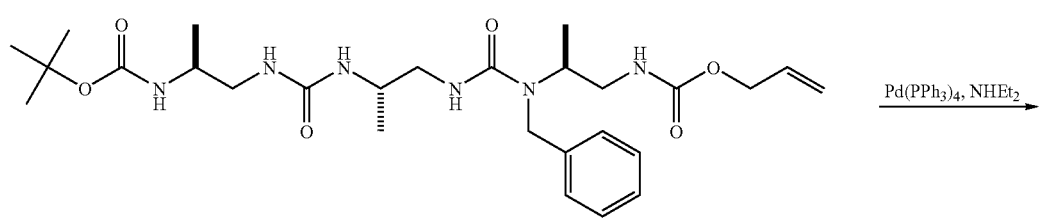
4
Pd(PPh$_3$)$_4$, NHEt$_2$
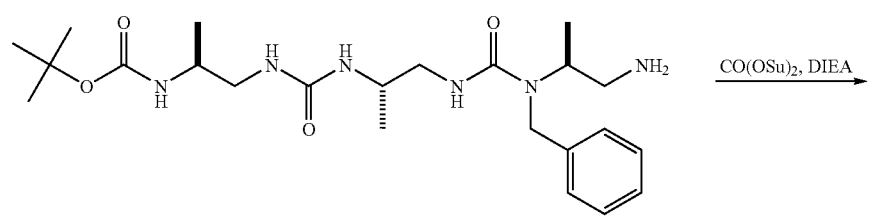
19
CO(OSu)$_2$, DIEA
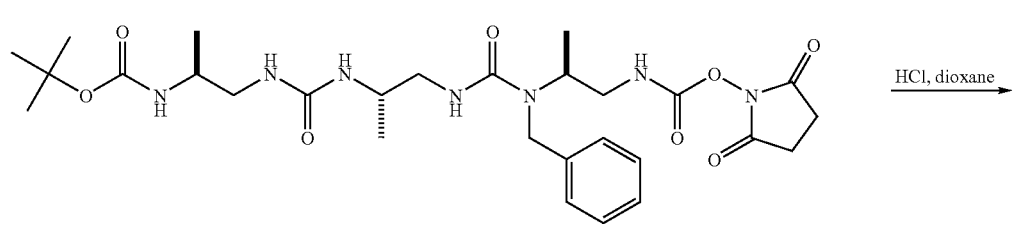
20
HCl, dioxane
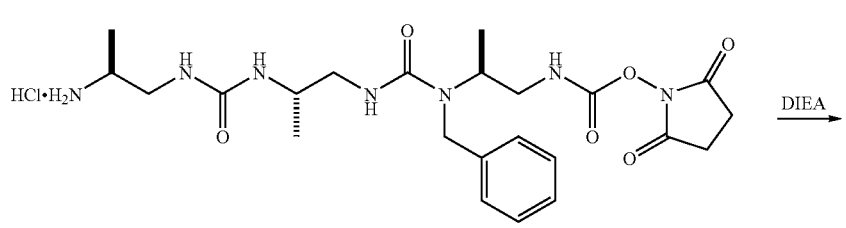
XXIV-a
DIEA
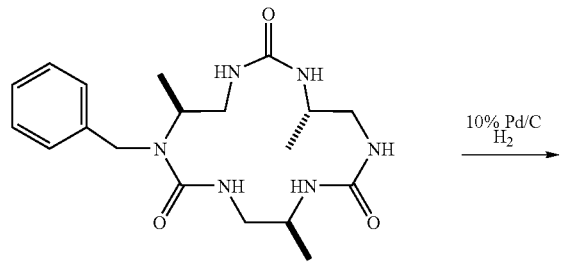
XV-1
10% Pd/C
H$_2$
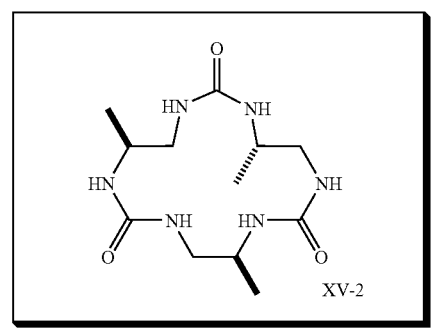
XV-2

Diagram 16:
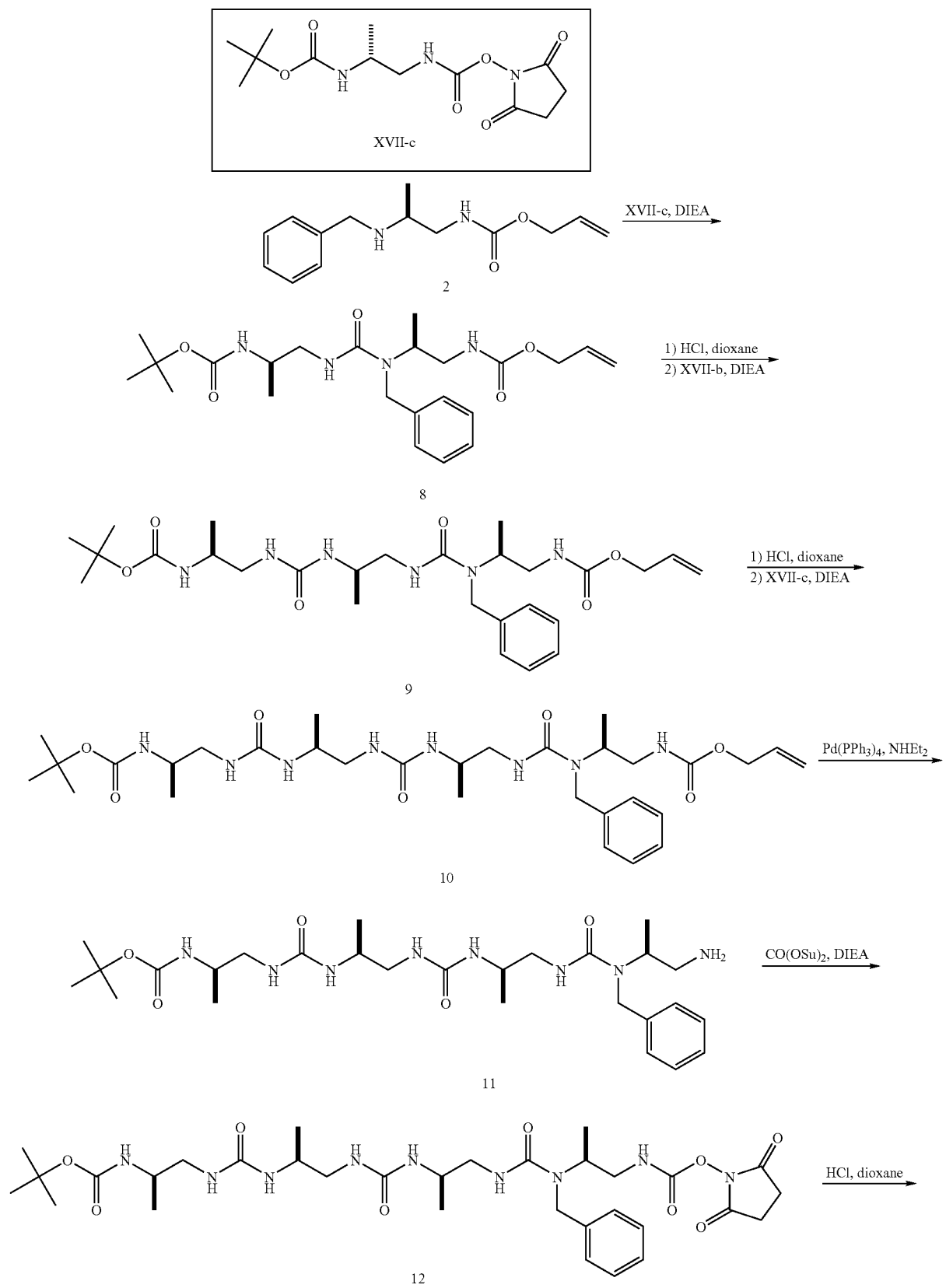

-continued
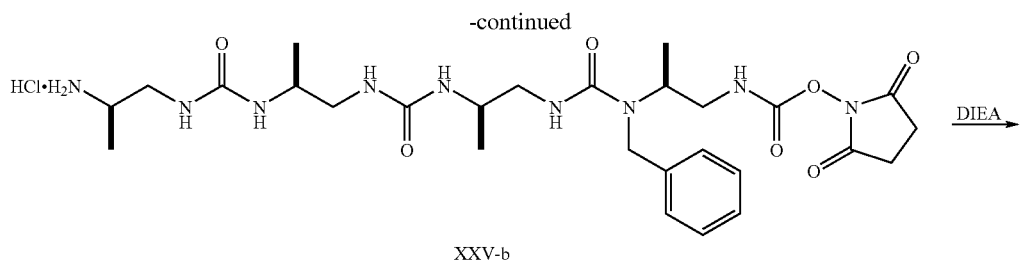
XXV-b
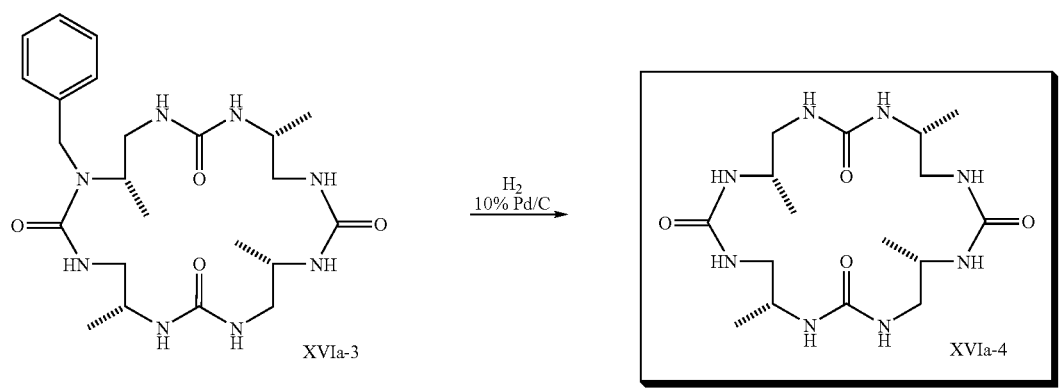
Diagram 17
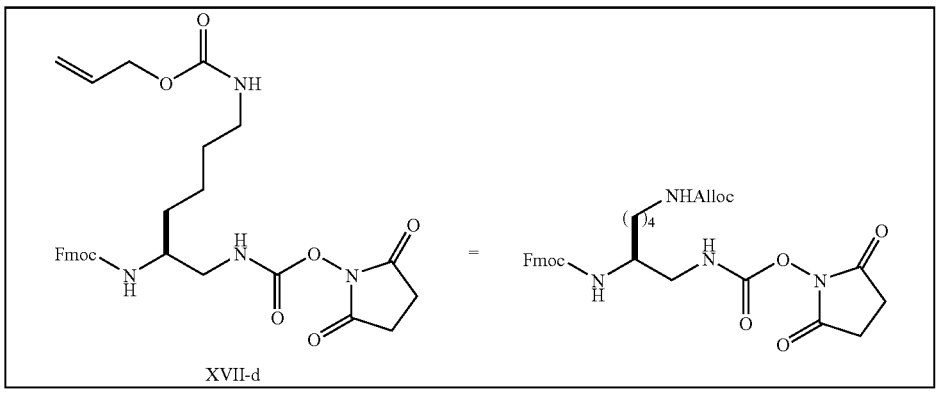
XVII-d
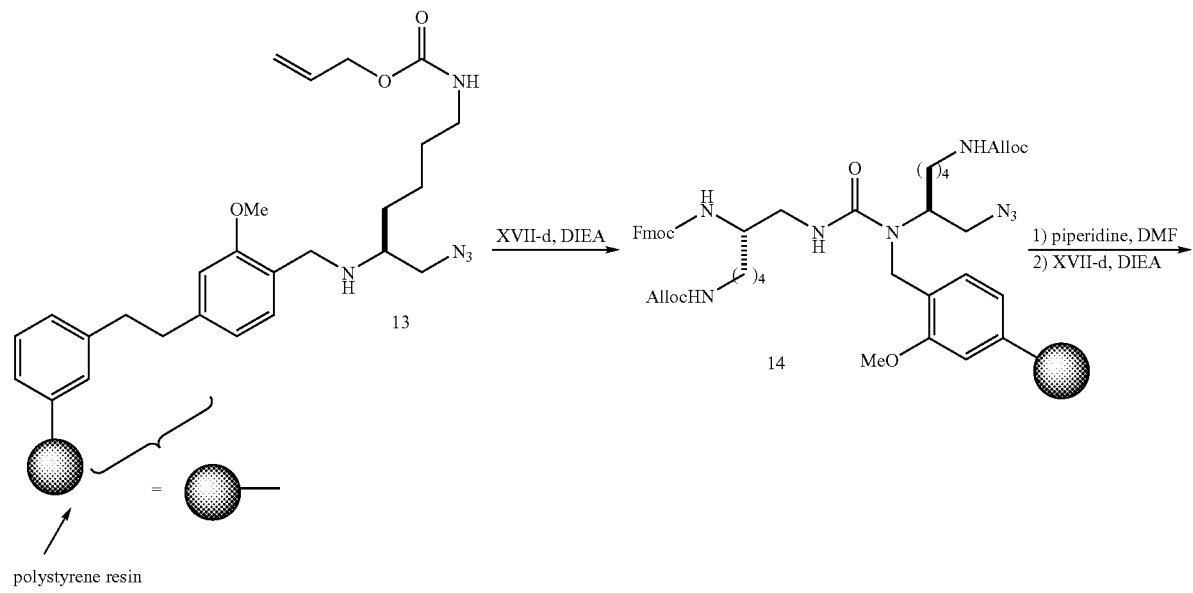

-continued
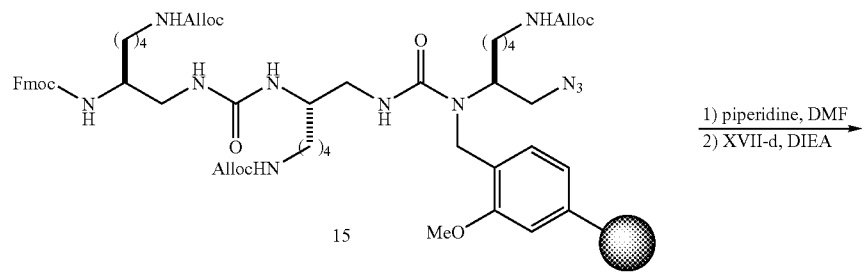
15
1) piperidine, DMF
2) XVII-d, DIEA
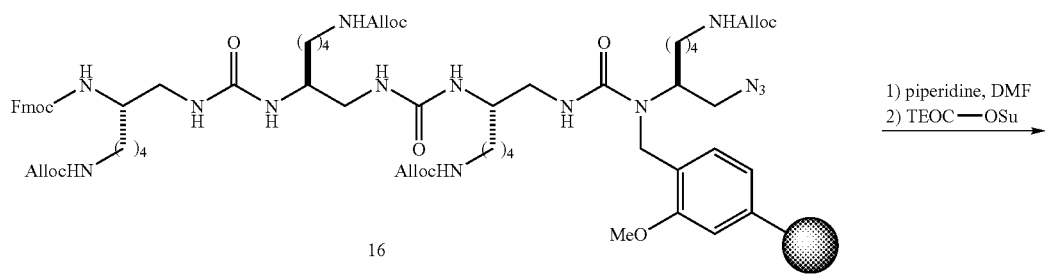
16
1) piperidine, DMF
2) TEOC—OSu
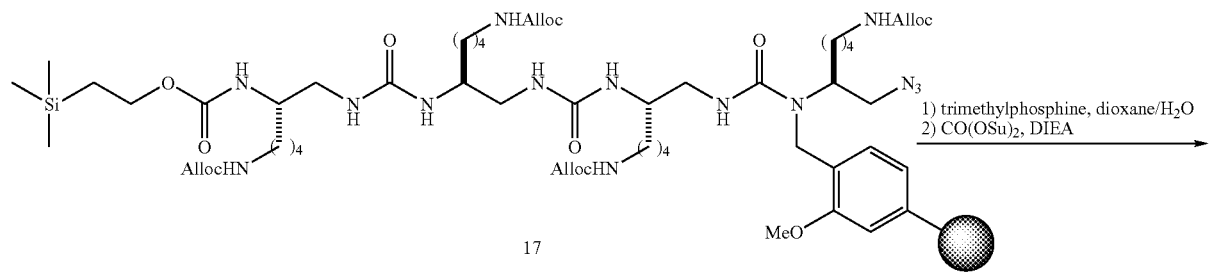
17
1) trimethylphosphine, dioxane/H₂O
2) CO(OSu)₂, DIEA
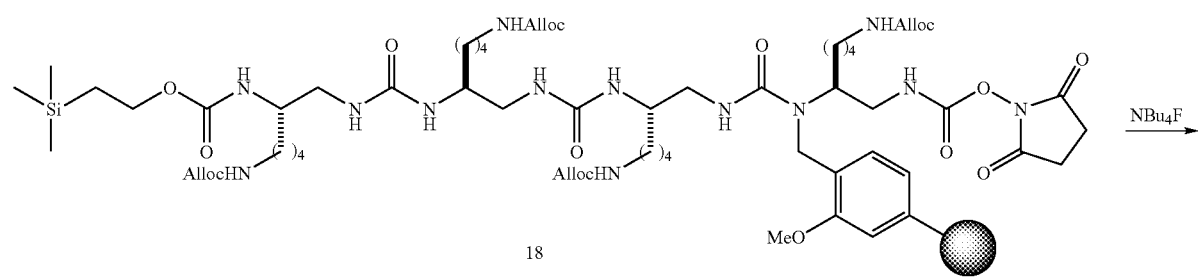
18
NBu₄F

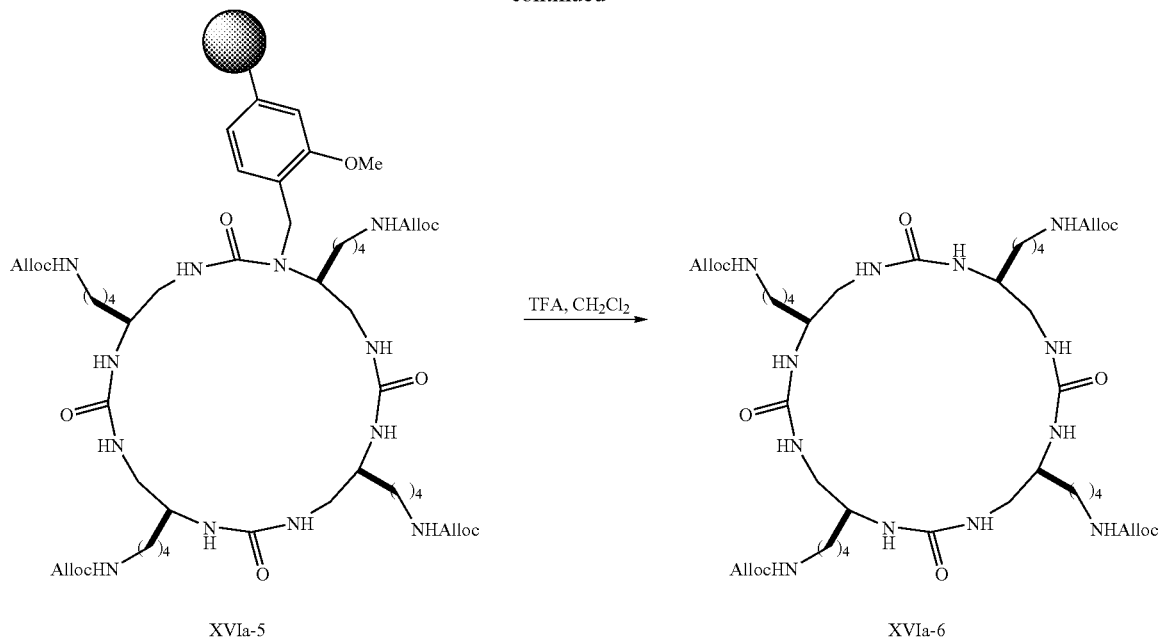
XVIa-5 → XVIa-6 (TFA, CH₂Cl₂)
Diagram 18
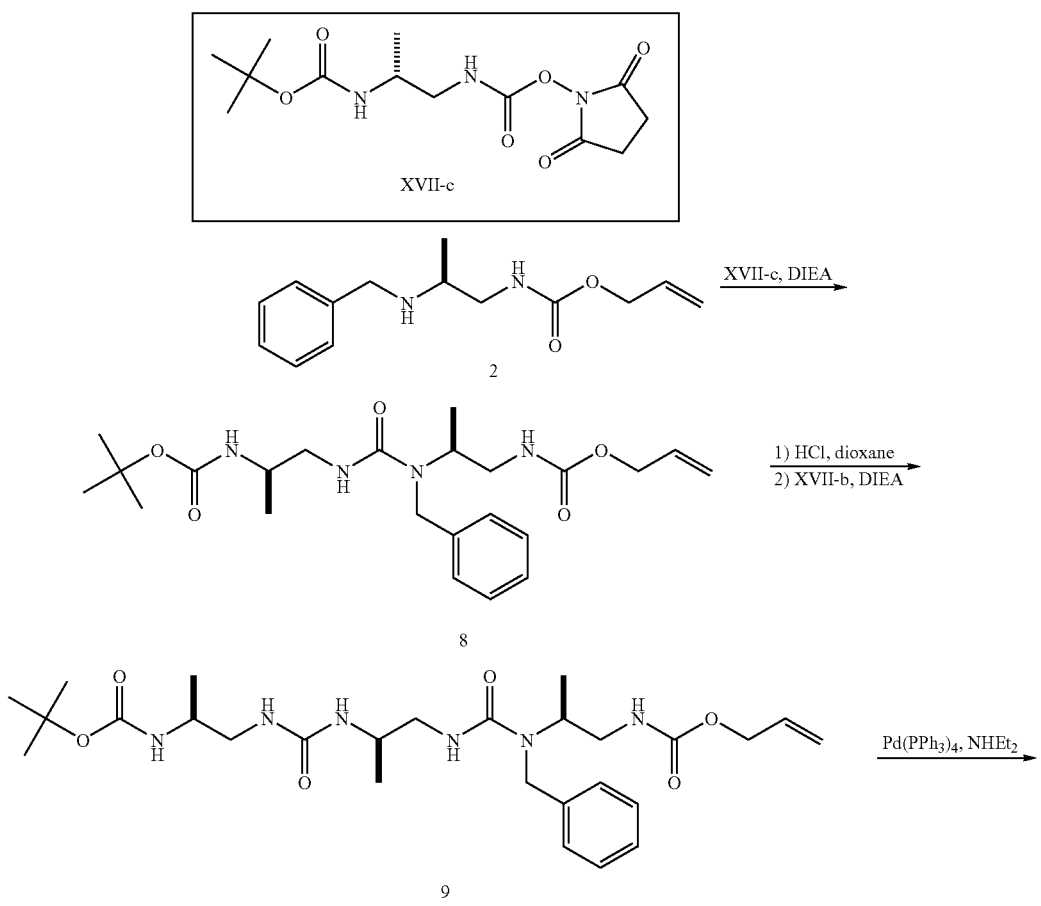

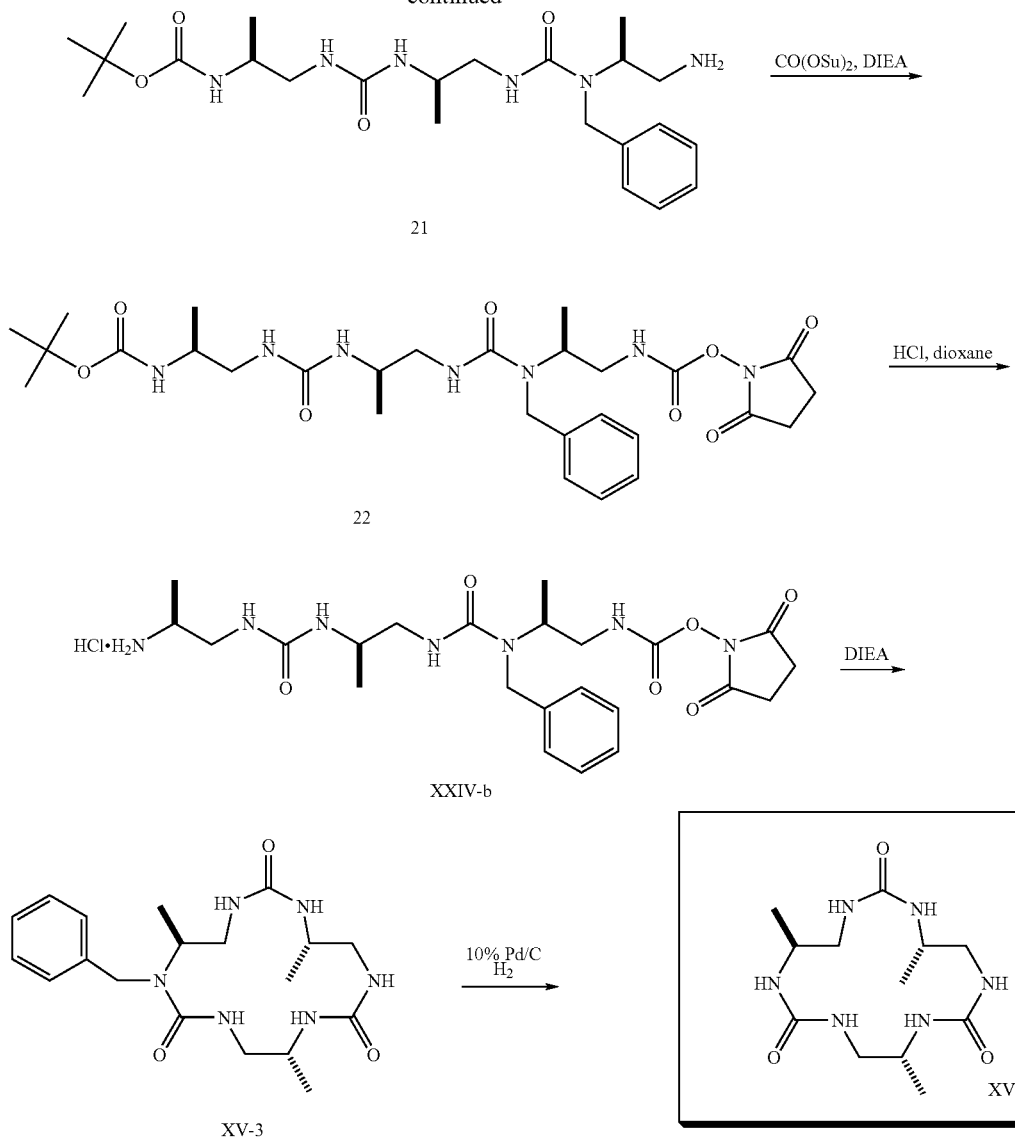
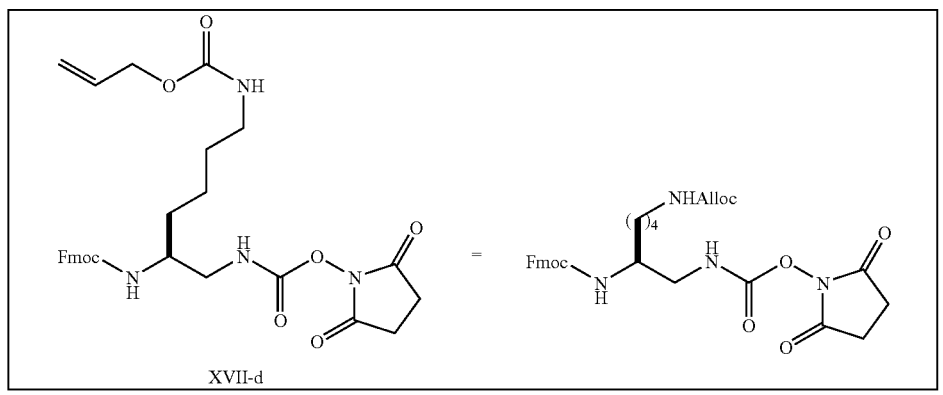
Diagram 19

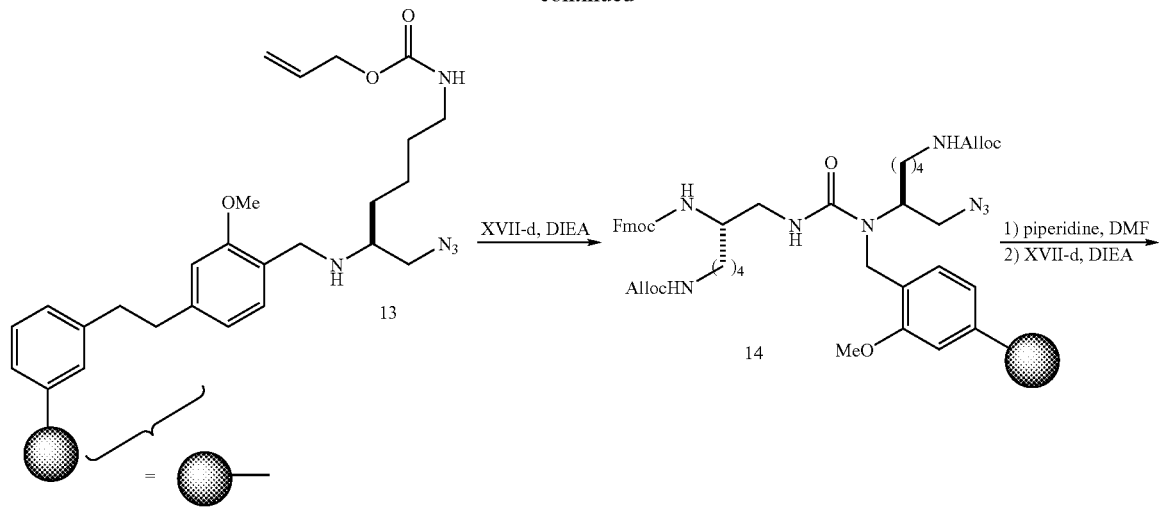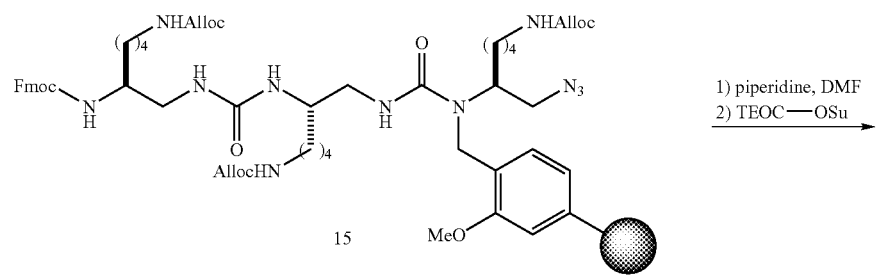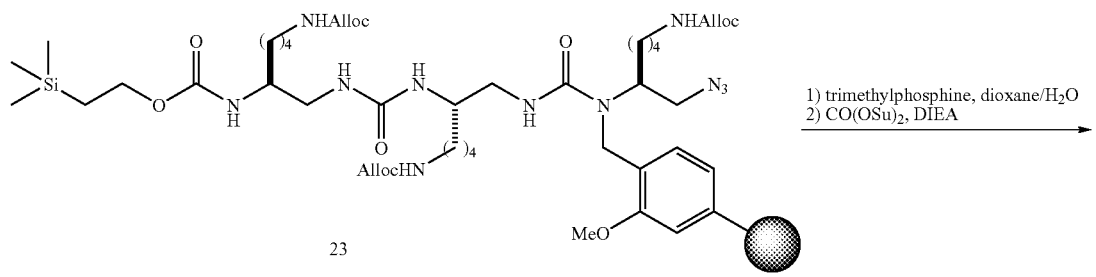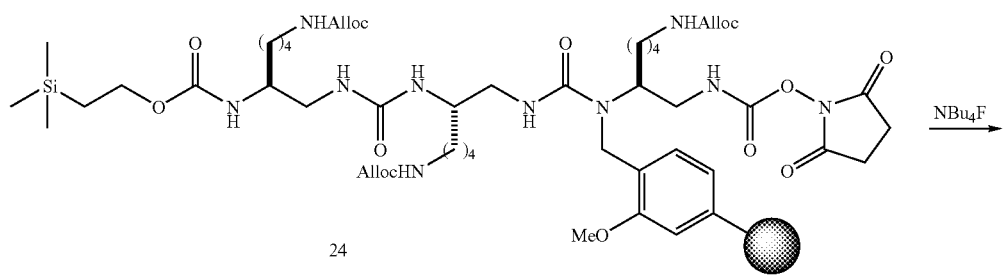

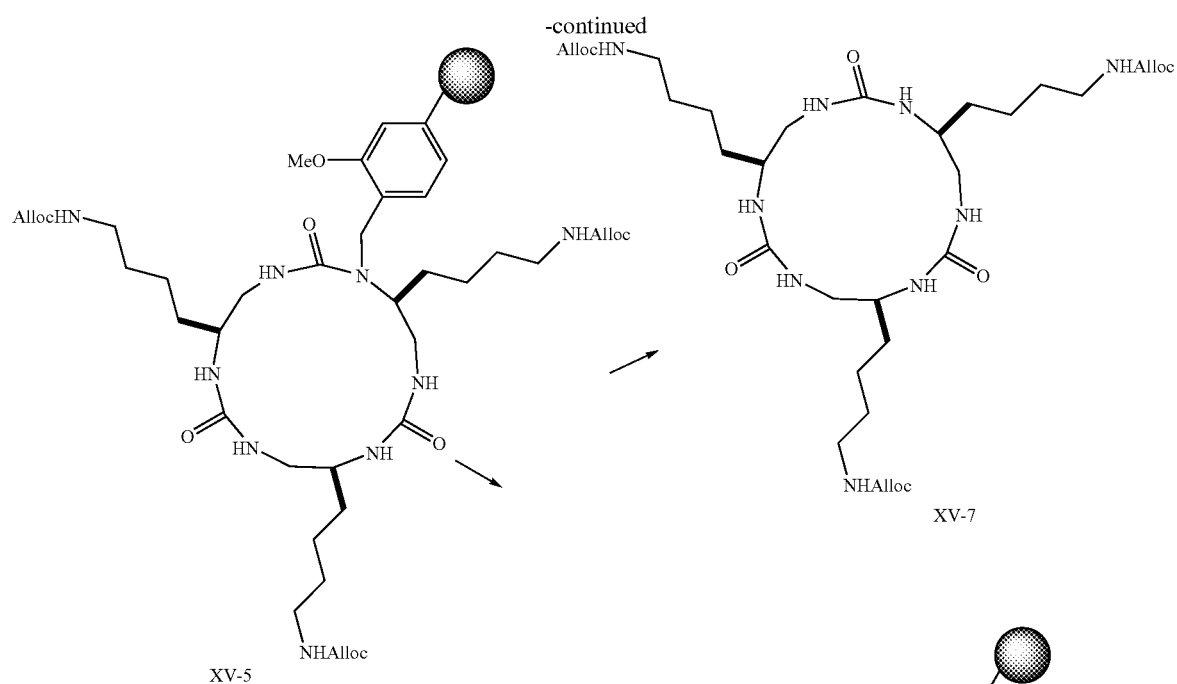
XV-5
Alloc = Allyloxycarbonyle
TEOC = trimethylsilylethoxycarbonyle
Diagram 20
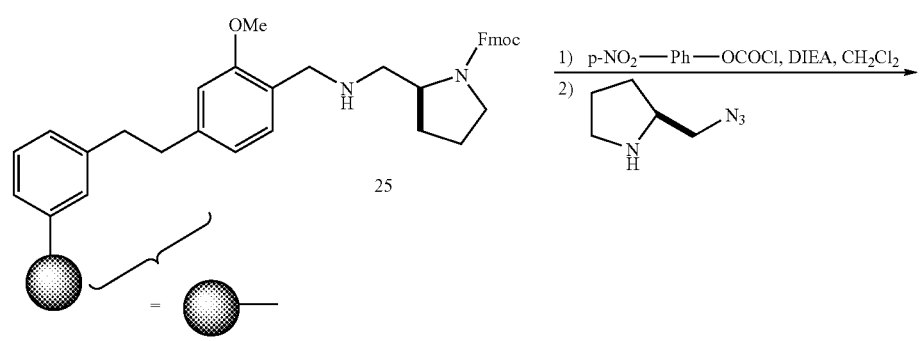

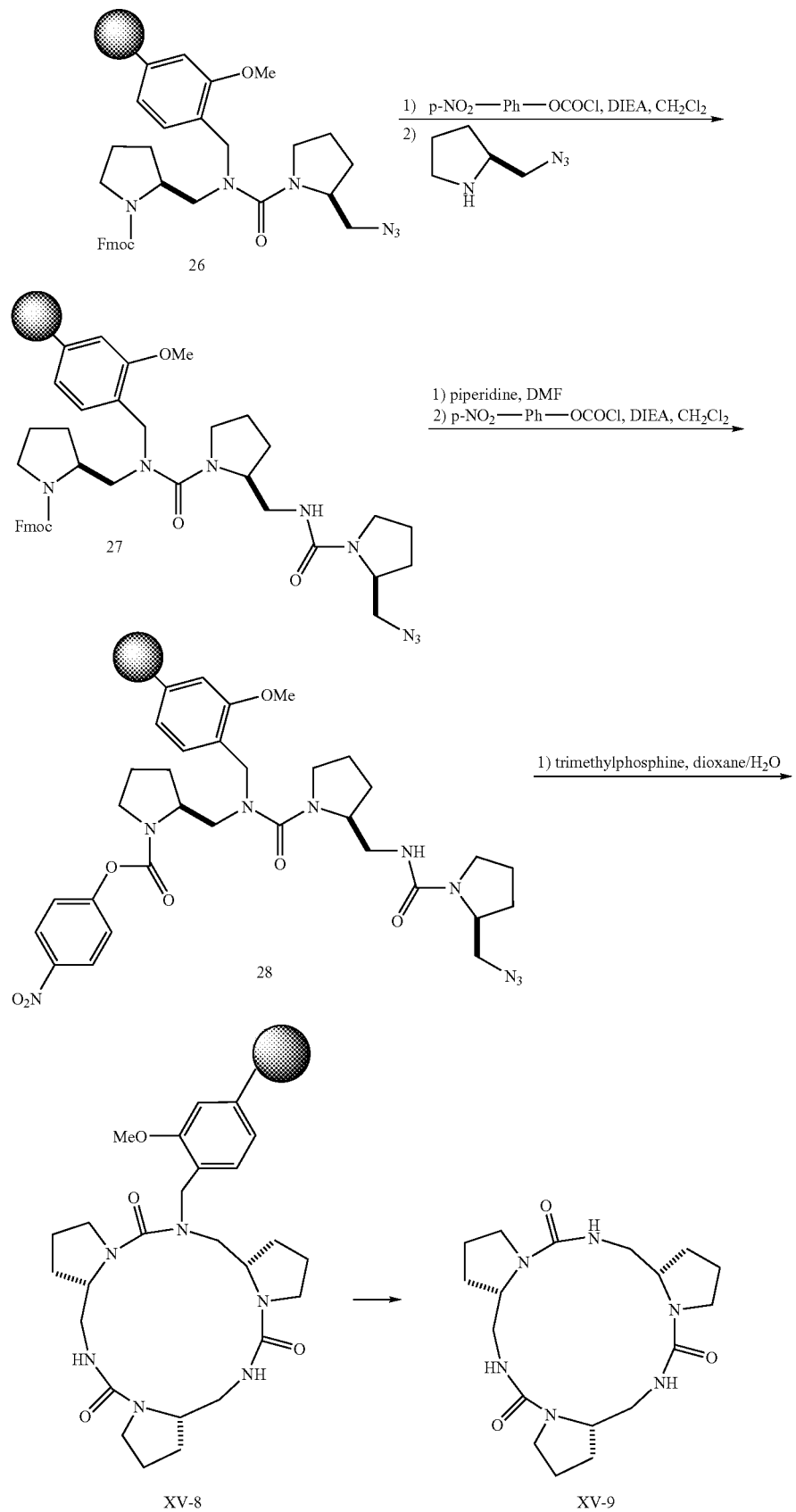

EXAMPLE 8

Intramolecular Cyclisation Reactions.

1. Importance of the Geometry of the Peptide Amide Bond in the Carbamic Acid Derivatives of Formula (VIc).

The cyclisation experiments carried out within the framework of the present invention using carbamic acid derivatives of type (VIc) (with X=succinimide) indicate that the geometry of the amide bond —CO—NR$^3$— (peptide bond) plays an important role in the nature of the products obtained, and more precisely in the size of the rings obtained. The peptide bond is characterised by its geometry which was established using crystallographic data and NMR. The peptide bond —CO—NR$^3$— can be either in trans configuration, or in cis configuration (cf. diagram 21). In general the equilibrium is shifted strongly towards the trans form. In the presence of proline or in the case of N-substitution, the cis form can become as important as the trans form.

Diagram 21:

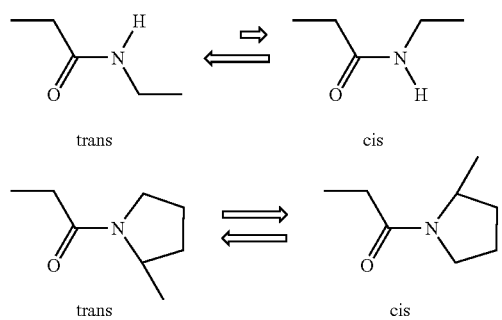

Compounds (VIc) for which R$^3$ is not a hydrogen, for example those for which R$^3$ is a methyl (cf. compound (VIc-6) of diagram 8) or those for which R$^3$ forms with R$^4$ a 5-atom proline ring (cf. compound (VIc-5) of diagram 7) preferably cyclise without intermolecular reaction before cyclisation, to give only the corresponding 7-atom ring (cyclic monomer) of type (Ia). This is certainly due to the cis preference of the amide bond in this type of compound. In effect, in very constrained rings, the amide bond is of cis geometry, and this geometry must be in the majority to allow the formation of the 7-atom ring.

Cyclisation of the compounds (VIc) for which R$^3$ is a hydrogen does not lead to the obtaining of the cyclic monomer. This is explained by the trans preference of the amide bond —CO—NR$^3$— in this type of precursor. The cyclisation occurs after one or more intramolecular coupling reactions, which leads to the obtaining of cyclic oligomers of variable size. Thus cyclisation of the compound (XIXa) (diagram 6) preferentially leads to the obtaining of the cyclic dimer (IIIf-4) (70%). However, study of the reaction raw material by mass spectrometry makes it possible to identify larger macrocycles (trimer, tetramer, pentamer) following a Gaussian distribution.

2. Preferred Cyclisation Conditions in the Case of Succinimidyl Carbamate Derivatives of Type (VIc).

The importance of a number of parameters (order of addition of the reagents, dilution, temperature) was evaluated during cyclisation of the derivatives (XIXa), (XIXb) and (XIXc) (cf. diagrams 6, 7 and 8).

Order of Addition of the Reagents

Generally the carbamic acid derivative containing a non-protected amine function ((VIc-4), (VIc-5) or (VIc-6)) rendered soluble in the reaction solvent (solvent used to carry out the cyclisation) (MeCN for example) is added dropwise to a solution containing a base and the reaction solvent (MeCN for example).

It is also possible to reverse this order by adding dropwise the solution containing a base and the reaction solvent to the solution containing the derivative to be cyclised ((VIc-4), (VIc-5) or (VIc-6)) and the reaction solvent.

Thus a reaction mixture is obtained containing the cyclic urea compounds (IIIf-4), (Ii) and (Ij) respectively.

Dilution Conditions

As regards the dilution, the concentration of the carbamic acid derivative containing a non-protected amine function ((VIc4), (VIc5) or (VIc-6)) in the reaction solvent (solvent used for the cyclisation) has no influence on the cyclisation of the derivatives (XIXb) and (XIXc). In these examples, the concentrations used vary from approximately 1 M to approximately $10^{-3}$ M.

In contrast, in the case of cyclisation of compound (XIXa), the dilution has an effect on the nature of the cyclic compounds obtained. When the reaction is carried out in a dilute solution (containing a carbamic acid derivative containing a non-protected amine function (VIc4), (VIc5) or (VIc-6) in the reaction solvent) whose concentration varies from approximately $10^{-5}$ M to $10^{-3}$ M, the main product obtained is the cyclic dimer (IIIf-4) (70%). The cyclic trimer represents less than 15%, and the cyclic tetramer less than 5%. In contrast, when the reaction is carried out at a higher concentration (above $10^{-3}$ M), the intermolecular reactions are clearly encouraged and rings of larger size (up to cyclic pentamer) are obtained, in higher proportions, to the detriment of the cyclic dimer.

Temperature Conditions

Temperature has only a slight influence on the cyclisation of products (XIXb) and (XIXc). Thus, the cyclisation reaction of derivatives (XIXb) and (XIXc) leads to derivatives (Ii) and (Ij) respectively in similar yields, whether the reaction takes place at 20° C., 0° C. or −10° C.

In contrast, the yield from cyclisation of compound (XIXa), leading to compound (IIIf-4), seems more sensitive to temperature, the best yield being obtained when the reaction is carried out between 0° C. and 20° C. For temperatures above 40° C., the reaction leads to an appreciable increase in the formation of rings which are larger in size (increase in the oligomerisation reaction) whereas at a temperature of −20° C. the reactivity of (XIXa) is very low and does not lead to the obtaining of compound (IIIf-4).

The invention claimed is:

1. Cyclic urea compounds comprising a ring of at least 7 atoms, said cycle comprising at least one carboxylic amide function and at least one urea function, each amide and urea function being separated from the closest adjacent amide or urea function by at least one methylenic carbon atom.

2. The cyclic urea compounds of claim 1, of formula (Ia):

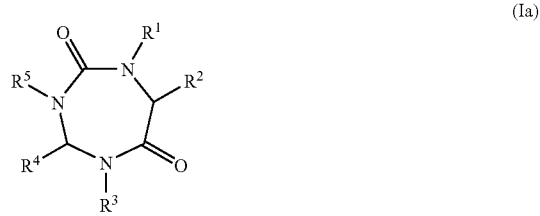

in which the R$^1$, R$^2$, R$^3$, R$^4$, and R$^5$ groups can each and independently from one another represent:
a) a hydrogen;
b) a halogen;
c) the protected or non-protected side chain of an amino acid chosen from the natural or non-natural amino acids;
d) a linear or branched alkyl (C1–C20) group, non-substituted or substituted by one or more substituents which include: —COOR$_a$, —CONHR$_a$, —OR$_a$, —NHR$_a$, —NH(CO)R$_a$, —NHCOOR$_a$, an aryl or heteroaryl group, whose cyclic structure contains from 5–20 carbon atoms, one halogen atom, and one R'''CO— group, the R''' group comprising from 1 to 10 carbon atoms, a nitrile, guanidino or nitro group;

e) one aryl group whose ring structure contains from 5 to 20 carbon atoms, substituted or non-substituted by the above-mentioned substituents, and by cyano or amidine groups;

f) an alkenyl or alkynyl group (C1–C6);

g) a sulfonyl group (R$_c$SO$_2$);

h) an acyl group (R$_c$CO);

i) an OR$_b$ group;

j) an NH$_2$ group;

k) —COOR$_b$;

l) —CONHR$_b$;

m) —CH$_2$CONH$_2$;

R$_a$ and R$_b$ representing, independently from one another, a hydrogen, an allyl, benzyl, t-butyl, fluorenylmethyl, benzyloxymethyl, tert-butyldimethylsilyl, 2-ethoxyethyl, methoxymethyl, 2-methoxyethoxymethyl, tetrahydropyran-2-yl, trimethylsilyl, triethylsilyl, 2-(trimethylsilyl)ethyl, trityl, 2,2,2-trichloroethyl, tosyl, ortho-(or para)-nitrophenylsulfonyl, alkyl group having from 1 to 20 carbon atoms, or an aryl group whose ring structure contains from 5–20 carbon atoms;

R$_c$ representing an alkyl group having from 1 to 20 carbon atoms, or an aryl group whose ring structure contains from 5–20 carbon atoms, or a heteroaryl, arylalkyl or heteroarylalkyl group;

the R$^1$, R$^2$, R$^3$ and R$^4$ groups also being able to form the following intramolecular cyclizations:

1/cyclization between R$^1$ and R$^2$ and/or;

2/cyclization between R$^3$ and R$^4$;

said cyclic urea compounds able to be, when one or more asymmetric carbons are present in formula (Ia), independently, either of R configuration (rectus) or of S configuration (sinister).

3. The cyclic urea compounds of claim 2, corresponding to formulae (Ib), (Ic), (Id), (Ie), (If), (Ig), (Ih):

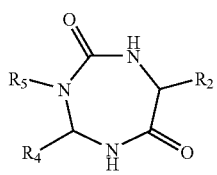
(Ih)

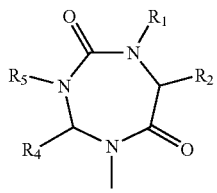
(Ib)

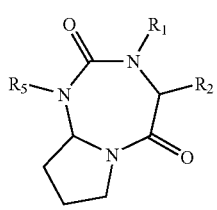
(Ic)

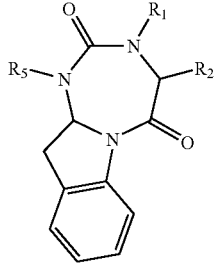
(Id)

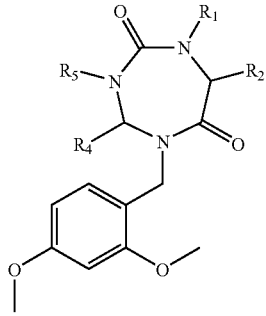
(Ie)

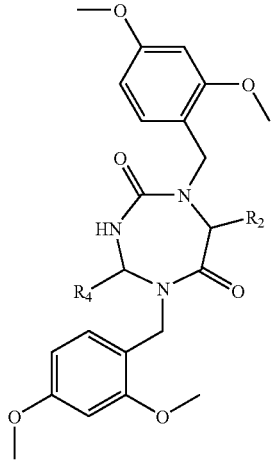
(If)

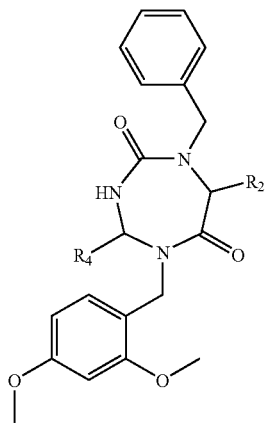
(Ig)

wherein the R1 and R2 groups also being capable of forming an intramolecular cyclization, said cyclic urea compounds able to be, when one or more asymmetric carbons are present in formulae (Ib) to (Ih), independently, either of R configuration (rectus) or of S configuration (sinister).

* * * * *